United States Patent
Kim et al.

(10) Patent No.: US 11,136,364 B2
(45) Date of Patent: *Oct. 5, 2021

(54) DUAL FUNCTION PROTEINS COMPRISING FGF21 MUTANT PROTEIN AND PHARMACEUTICAL COMPOSITION COMPRISING SAME

(71) Applicant: YUHAN CORPORATION, Seoul (KR)

(72) Inventors: Jun Hwan Kim, Seoul (KR); Seyoung Lim, Yongin-si (KR); Minji Seo, Seoul (KR); Hyun Ho Choi, Suwon-si (KR); Dohoon Kim, Yongin-si (KR); Mi Kyeong Ju, Suwon-si (KR); Ju-Young Park, Seoul (KR); Seul Gi Kim, Suwon-si (KR); Sangmyoun Lim, Seoul (KR); Jong Gyun Kim, Anyang-si (KR); Su Youn Nam, Seoul (KR)

(73) Assignee: YUHAN CORPORATION, Seoul (KR)

( * ) Notice: Subject to any disclaimer, the term of this patent is extended or adjusted under 35 U.S.C. 154(b) by 147 days.

This patent is subject to a terminal disclaimer.

(21) Appl. No.: 15/768,865

(22) PCT Filed: Oct. 28, 2016

(86) PCT No.: PCT/KR2016/012300
§ 371 (c)(1),
(2) Date: Apr. 17, 2018

(87) PCT Pub. No.: WO2017/074123
PCT Pub. Date: May 4, 2017

(65) Prior Publication Data
US 2020/0024318 A1    Jan. 23, 2020

(30) Foreign Application Priority Data
Oct. 28, 2015   (KR) .................. 10-2015-0150576

(51) Int. Cl.
*A61K 38/18*    (2006.01)
*C07K 14/50*    (2006.01)
*C07K 14/575*   (2006.01)
*C07K 14/605*   (2006.01)

(52) U.S. Cl.
CPC ............ *C07K 14/50* (2013.01); *C07K 14/575* (2013.01); *C07K 14/605* (2013.01); *C07K 2319/30* (2013.01)

(58) Field of Classification Search
None
See application file for complete search history.

(56) References Cited

U.S. PATENT DOCUMENTS

| | | |
|---|---|---|
| 5,851,800 A | 12/1998 | Adamson et al. |
| 9,023,791 B2 | 5/2015 | Boettcher et al. |
| 9,434,778 B2 | 9/2016 | Morin et al. |
| 9,441,030 B2 | 9/2016 | Song et al. |
| 2012/0172298 A1 | 7/2012 | Andersen et al. |
| 2012/0238496 A1 | 9/2012 | Fan et al. |
| 2013/0129724 A1 | 5/2013 | Boettcher et al. |
| 2014/0213512 A1 | 7/2014 | Ellison et al. |
| 2014/0243503 A1 | 8/2014 | Belouski et al. |

FOREIGN PATENT DOCUMENTS

| | | |
|---|---|---|
| CN | 102558358 A | 7/2012 |
| CN | 105288592 A | 2/2016 |
| EA | 020843 B1 | 2/2015 |
| EP | 0 306 968 A2 | 3/1989 |
| EP | 2 548 570 A1 | 1/2013 |
| WO | 90/02175 A1 | 3/1990 |
| WO | 03/011213 A2 | 2/2003 |
| WO | 2003/011213 A2 | 2/2003 |
| WO | 03/059934 A2 | 7/2003 |
| WO | 2005/000892 A2 | 1/2005 |
| WO | 2005/091944 A2 | 10/2005 |
| WO | 2009/020802 A2 | 2/2009 |
| WO | 2010/065439 A1 | 6/2010 |
| WO | 2010091122 A1 | 8/2010 |
| WO | 2010/129503 A1 | 11/2010 |
| WO | 2010/129600 A2 | 11/2010 |
| WO | 2010/142665 A1 | 12/2010 |
| WO | 2011/020319 A1 | 2/2011 |

(Continued)

OTHER PUBLICATIONS

Alexei Kharitonenkov et al., "FGF-21 as a novel metabolic regulator," The Journal of Clinical Investigation, Jun. 2005, pp. 1627-1635, vol. 115, No. 6.
Bernard Thorens et al., "Cloning and Functional Expression of the Human Islet GLP-1 Receptor," Diabetes, Nov. 1993, pp. 1678-1682, vol. 42.
H. Kahal et al., "Glucagon-like peptide-1 analogue, liraglutide, improves liver fibrosis markers in obese women with polycystic ovary syndrome and nonalcoholic fatty liver disease", Clinical Endocrinology, 2014, pp. 523-528, vol. 81.

(Continued)

*Primary Examiner* — Christine J Saoud
(74) *Attorney, Agent, or Firm* — Sughrue Mion, PLLC

(57) ABSTRACT

The present invention provides a dual function protein prepared by linking a biologically active protein and an FGF mutant protein to an Fc region of an immunoglobulin, which has improved pharmacological efficacy, in vivo duration and protein stability. A dual function protein according to the present invention exhibits improved pharmacological efficacy, in vivo duration and protein stability, and a pharmaceutical composition containing the dual function protein as an active ingredient may be effectively used as a therapeutic agent for diabetes, obesity, dyslipidemia, metabolic syndrome, non-alcoholic fatty liver diseases, non-alcoholic steatohepatitis or cardiovascular diseases.

25 Claims, 24 Drawing Sheets

Specification includes a Sequence Listing.

(56) References Cited

FOREIGN PATENT DOCUMENTS

| WO | 2011/089170 A1 | 7/2011 |
|---|---|---|
| WO | 2012/010553 A1 | 1/2012 |
| WO | 2012/066075 A1 | 5/2012 |
| WO | 2012/170438 A2 | 12/2012 |
| WO | 2013/033452 A2 | 3/2013 |
| WO | 2013131091 A1 | 9/2013 |
| WO | 2013/188181 A1 | 12/2013 |
| WO | 2014/130659 A1 | 8/2014 |
| WO | 2015038938 A1 | 3/2015 |
| WO | 2017/074117 A1 | 5/2017 |
| WO | 2017/074123 A1 | 5/2017 |
| WO | 2018/166461 A1 | 9/2018 |
| WO | 2018/194413 A1 | 10/2018 |

OTHER PUBLICATIONS

Hecht et al., "Rationale-Based Engineering of a Potent Long-Acting FGF21 Analog for the Treatment of Type 2 Diabetes", PLOS One, Nov. 2012, vol. 7, Issue 11, e49345, pp. 1-14 (total 14 pages).

Jie Huang et al., "Development of a Novel Long-Acting Antidiabetic FGF21 Mimetic by Targeted Conjugation to a Scaffold Antibody", the Journal of Pharmacology and Experimental Therapeutics, Aug. 2013, pp. 270-280, vol. 346.

Justin D. Schumacher et al., "Regulation of Hepatic Stellate Cells and Fibrogenesis by Fibroblast Growth Factors", BioMed Research International, Jan. 2016 (Posted on ResearchGate), 21 pages.

Mashkovsky M.D. Medicines, 16th ed., Revised, revised. Novaya Volna, 2012, p. 8 (2 pages total).

Yakubke H.-D et al., Amino acids, peptides, proteins. Mir, 1985, p. 92-94 (5 pages total).

English Translation of Office Action dated Jan. 28, 2021 in Russian Application No. 2019117767.

| Test | DFD23 | DFD24 | DFD25 | DFD26 | DFD27 | DFD28 | DFD29 |
|---|---|---|---|---|---|---|---|
| $EC_{50}$ (pM) | 272.8 | 107.4 | 88.6 | 104.9 | 99.0 | 69.7 | 78.6 |

| Test | DFD69 | DFD112 | DFD114 | DFD59 |
|---|---|---|---|---|
| $EC_{50}$ (pM) | 187.5 | 129.5 | 168.8 | 72.1 |

| Test | DFD69 | DFD112 | DFD114 |
|---|---|---|---|
| $EC_{50}$ (nM) | 16.84 | 12.16 | 15.52 |

DUAL FUNCTION PROTEINS COMPRISING FGF21 MUTANT PROTEIN AND PHARMACEUTICAL COMPOSITION COMPRISING SAME

CROSS REFERENCE TO RELATED APPLICATIONS

This application is a National Stage of International Application No. PCT/KR2016/012300 filed Oct. 28, 2016, claiming priority based on Korean Patent Application No. 10-2015-0150576 filed Oct. 28, 2015.

TECHNICAL FIELD

The present invention relates to a dual function protein including a biologically active protein and a fibroblast growth factor 21 (FGF21) mutant protein, and a pharmaceutical composition containing same.

BACKGROUND ART

Glucagon-like peptide-1 (GLP-1) is an incretin hormone consisting of 31 amino acids, which is secreted by L cells in the intestinal tract when stimulated by food, etc. Its biological effects arise via intracellular signaling through the GLP-1 receptor, a G protein-coupled receptor which is expressed in target tissues such as β-cells in the pancreas, brain, etc. GLP-1 secreted in the blood has a very short half-life of less than 2 minutes, which is caused by a loss of activity due to the cleavage of amino acids at the N-terminus by the enzyme dipeptidyl peptidase-4 (DPP-4). Since GLP-1 stimulates the secretion of insulin in β-cells in the pancreas based on blood glucose level, it has a strong effect on lowering blood glucose without inducing hypoglycemia. Further, the administration of GLP-1 results in loss of body weight in various animal models and humans, which is known to be caused by reduced food intake due to its effect on appetite suppression. GLP-1 induces proliferation of β-cells and enhances the viability of β-cells by inhibiting cell death caused by glycolipid toxicity through GLP-1 receptor expressed in β-cells in the pancreas. Excessive secretion of glucagon increases blood glucose, which is known to be one of the causes of hyperglycemia in diabetics. In addition, it is known that GLP-1 acts on α-cells in the pancreas to inhibit fasting blood glucose elevation by inhibiting secretion of protein kinase A (PKA) protein-specific glucagon.

Exendin-4 is a clinically important GLP-1 receptor agonist. Exendin-4 is a polypeptide with 39 amino acid residues, and is normally produced in the salivary glands of the Gila Monster lizard. It is known that exendin-4 an amino acid sequence homology of 52% with GLP-1, and interacts with the GLP-1 receptor in mammals (Thorens et al. (1993) *Diabetes* 42:1678-1682). Exendin-4 has been shown to stimulate the secretion of insulin by insulin-producing cells in vitro, and the induction of insulin release by insulin-producing cells is stronger than GLP-1 under equimolar conditions. While exendin-4 strongly stimulates the secretion of insulin to decrease blood glucose levels in both rodents and humans with a duration of action longer than that of GLP-1, exendin-4 has exhibits antigenicity in mammals devoid of GLP-1 as it has unfamiliar epitopes in such animals.

The ability of GLP-1 and exendin-4 analogs (e.g., liraglutide and byetta) to improve glucose control in humans has been clinically confirmed. It has been reported that GLP-1 increases β-cell mass through the inhibition of apoptosis and induced proliferation. Furthermore, it has been also reported that GLP-1 acts as an intestinal hormone inhibiting gastric acid secretion and gastric emptying while enhancing satiety signals, thereby reducing appetite. Such effects of GLP-1 can explain the weight loss observed when GLP-1 analogs are administered to patients with type 2 diabetes. In addition, GLP-1 exhibits cardioprotective effects following ischemia in rodents.

Various attempts have been made to develop long-acting GLP-1 analogs. Clinically confirmed long-acting GLP-1 analogs include dulaglutide (WO 2005/000892) and albiglutide (WO 2003/059934). Dulaglutide is an Fc-fused GLP-1 analog, and albiglutide is an albumin-fused GLP-1 analog, both of which have pharmacokinetic profiles allowing for once weekly administration. Both drugs have excellent effects on lowering blood glucose and reducing body weight with once weekly administration, and also provide greatly improved convenience in terms of treatment when compared to byetta and liraglutide.

Meanwhile, fibroblast growth factor 21 (FGF21), synthesized in the liver, is a hormone known to play an important role in glucose and lipid homeostasis. FGF21 exhibits pharmacological actions in the liver, adipocytes, β cells of the pancreas, hypothalamus in the brain, and muscle tissues, where both an FGF21-specific receptor, i.e., FGF receptor, and β-klotho complex are expressed. It has been reported that in non-human primate and murine models of various diabetic and metabolic diseases, FGF21 can lower blood glucose levels in an insulin-independent manner, reduce body weight, and lower triglyceride and low-density lipoprotein (LDL) concentrations in the blood. Additionally, due to its effect of improving insulin sensitivity, FGF21 has potential for development as a novel therapeutic agent for diabetes and obesity (see WO2003/011213).

Accordingly, in order to develop a novel anti-diabetic drug based on FGF21, attempts have been made to improve its biological activity and in vivo stability by constructing FGF21 mutants based on the wild-type FGF21 sequence via substitution, insertion, and deletion of some amino acids (see WO2010/065439). However, as FGF21 has a very short half-life, it has proven problematic if used directly as a biotherapeutic agent (Kharitonenkov, A. et al. (2005) *Journal of Clinical Investigation* 115:1627-1635). The in vivo half-life of FGF21 is 1 to 2 hours in mice, and 2.5 to 3 hours in monkeys. Therefore, for FGF21 to be used in its current form as a therapeutic agent for diabetes, daily administration is required.

Various approaches have been reported in attempting to increase the in vivo half-life of FGF21 recombinant proteins. One such example is to link polyethylene glycol (PEG), i.e., a polymer material, to FGF21 to increase its molecular weight, thereby inhibiting renal excretion and increasing in vivo retention time (see WO2012/066075). Another approach attempts to improve the half-life by fusing it with a fatty acid, which binds to human albumin (see WO2012/010553). An additional example attempts to increase the half-life while maintaining pharmacological activity equivalent to that of wild-type FGF21 through the generation of an agonist antibody, which specifically binds to the human FGF receptor alone or as a complex with β-klotho (see WO2012/170438). In another example, the half-life was improved by preparing long-acting fusion proteins, in which an Fc region of IgG binds to an FGF21 molecule (see WO2013/188181).

Among the various technologies available to create long-acting drugs, Fc fusion technology is widely used because it has less of the disadvantages seen with other approaches, such as inducing an immune response or toxicity while increasing in vivo half-life. For the development of an Fc-fused FGF21 protein as a long-acting therapeutic drug, the following conditions should be satisfied.

First, the decrease of in vitro activity caused by fusion should be minimized. Both the N-terminus and C-terminus of FGF21 are involved in FGF21's activity. In this regard, it is known that the activities of FGF21 fusion proteins greatly vary depending on the location of the fusion. Accordingly, the activities of Fc-fused FGF21 fusion proteins, in which mutations are introduced into FGF21, may be altered depending on the presence/absence or location of the fusion. Second, a pharmacokinetic profile enabling administration at an interval of once per week in humans should be realized by the increase of in vivo half-life by the fusion. Third, considering that immunogenicity may be expected in most patients after administration of biopharmaceuticals, the immunogenicity risk due to a fusion linker or mutation should be minimized. Fourth, there should be no stability issues arising from the position of the fusion or the introduction of the mutation. Fifth, since undesired immune responses may occur depending on the isotypes of fused immunoglobulin, a solution to prevent such responses is necessary.

An attempt to develop a long-acting fusion protein by linking the Fc region of an immunoglobulin G (IgG) to an FGF21 molecule has already been reported (see WO 2013/188181). In the case of one Fc-FGF21 structure, where the Fc is fused to the N-terminus of the wild-type FGF21, while there is no distinct difference in in vitro activity as compared to that of the wild-type FGF21, the half-life is known to be very short due to in vivo degradation of the protein. To address this issue, there has been an attempt to improve the in vivo half-life by introducing several mutations at specific site locations of FGF21 to resist protein degradation. However, immunogenicity risk may increase with the introduction of multiple mutations. In contrast, in the case of an FGF21-Fc structure, where the Fc is fused to the C-terminus of the FGF21 molecule, it is known that there is a significant decrease in activity caused by fusion at this site when compared to the Fc-FGF21 structure.

Combined administration of GLP-1 and FGF21 may have a synergistic effect as compared with single administration depending on the action mechanisms and target tissues in the body, and potentially outstanding anti-diabetic efficacy and additional advantages are expected. The effects of combined administration of GLP-1 and FGF21 or a GLP-1/FGF21 dual function protein have been already investigated and reported (see WO 2010/142665 and WO 2011/020319).

Various problems must be solved in order to develop a dual function protein comprising GLP-1 and FGF21. Since wild-type GLP-1 and wild-type FGF21 have a very short in vivo half-life, they are required to be administered at least once daily, even if developed as therapeutic agents. Accordingly, long-acting technologies such as an Fc fusion are required in order to develop a long-acting dual function protein to improve convenience for patients. In a dual function drug for the two targets of GLP-1 and FGF21, the introduction of mutation(s) is essential to maintain the activity and in vivo stability of each drug, and problems associated with changes in activity, structure or stability caused by each mutation should be addressed. Medicinal effects for the two targets of GLP-1 and FGF21 should be well-balanced, and drug designs considering in vitro activities, pharmacokinetic profiles, pharmacological efficacy in animal models as well as clinical evaluation of efficacy in humans are required for this purpose. A dual function protein has a structure that cannot exist in a human body, and is structurally complex as compared with a fusion protein for a single target. In addition, since mutation or linker engineering is required to balance the two targets, the possibility of forming aggregate complexes may increase, and further protein engineering to prevent this may be required. Furthermore, potential immunogenicity may increase due to novel mutation sequences or complex structures, which should be addressed or avoided.

The present inventors have endeavored to improve the stability, pharmacokinetic profiles and pharmacological efficacy of dual function proteins including GLP-1 mutant proteins and FGF21 mutant proteins, and discovered that the stability, pharmacokinetic profiles and pharmacological efficacy of dual function proteins may be improved when a GLP-1 mutant protein is fused to an Fc region of an immunoglobulin and a novel FGF21 mutant protein is fused thereto, thereby accomplishing the present invention.

DISCLOSURE OF INVENTION

Technical Problem

An object of the present invention is to provide a dual function protein including a biologically active protein and an FGF21 mutant protein with improved pharmacokinetic parameters, high stability, low possibility of forming aggregation complexes, and reduced potential immunogenicity.

Another object of the present invention is to provide a pharmaceutical composition including the dual function protein for preventing or treating FGF21-associated disorders.

A further object of the present invention is to provide an isolated nucleic acid molecule encoding the dual function protein, an expression vector including the nucleic acid molecule, and a host cell including the expression vector.

Solution to Problem

The present invention provides a dual function protein comprising an FGF21 mutant protein; a biologically active protein, or a mutant or fragment thereof; and an Fc region of an immunoglobulin, wherein the FGF21 mutant protein comprises at least one mutation selected from the group consisting of the following mutations (1) to (7):

(1) a substitution of amino acids at positions 98 to 101 from the N-terminus of a wild-type FGF21 protein with an amino acid sequence of EIRP (SEQ ID NO: 68);

(2) a substitution of amino acids at positions 170 to 174 from the N-terminus of a wild-type FGF21 protein with an amino acid sequence of TGLEAV (SEQ ID NO: 69);

(3) a substitution of amino acids at positions 170 to 174 from the N-terminus of a wild-type FGF21 protein with an amino acid sequence of TGLEAN (SEQ ID NO: 70);

(4) a substitution of an amino acid at position 170 from the N-terminus of a wild-type FGF21 protein with an amino acid N;

(5) a substitution of an amino acid at position 174 from the N-terminus of a wild-type FGF21 protein with an amino acid N;

(6) a substitution of an amino acid at position 180 from the N-terminus of a wild-type FGF21 protein with an amino acid E, along with one or more mutations (1) to (5) above; and (7) a mutation of 1 to 10 amino acids for reducing immunogenicity of a wild-type FGF21 protein.

In addition, the present invention provides a pharmaceutical composition comprising the dual function protein for treating diabetes, obesity, dyslipidemia, metabolic syndrome, non-alcoholic fatty liver disease, non-alcoholic steatohepatitis or cardiovascular diseases.

Further, the present invention provides an isolated nucleic acid molecule encoding the dual function protein, an expression vector comprising the nucleic acid molecule, and a host cell comprising the expression vector.

Advantageous Effects of Invention

A dual function protein of the present invention, prepared by linking a biologically active protein and an FGF mutant protein to an Fc region of an immunoglobulin, has improved pharmacological efficacy, in vivo duration and protein stability. In addition, a pharmaceutical composition including the dual function protein as an active ingredient can be used as a therapeutic agent for diabetes, obesity, dyslipidemia, metabolic syndrome, non-alcoholic fatty liver diseases, non-alcoholic steatohepatitis or cardiovascular diseases.

BEST MODE FOR CARRYING OUT THE INVENTION

Figure 1A:
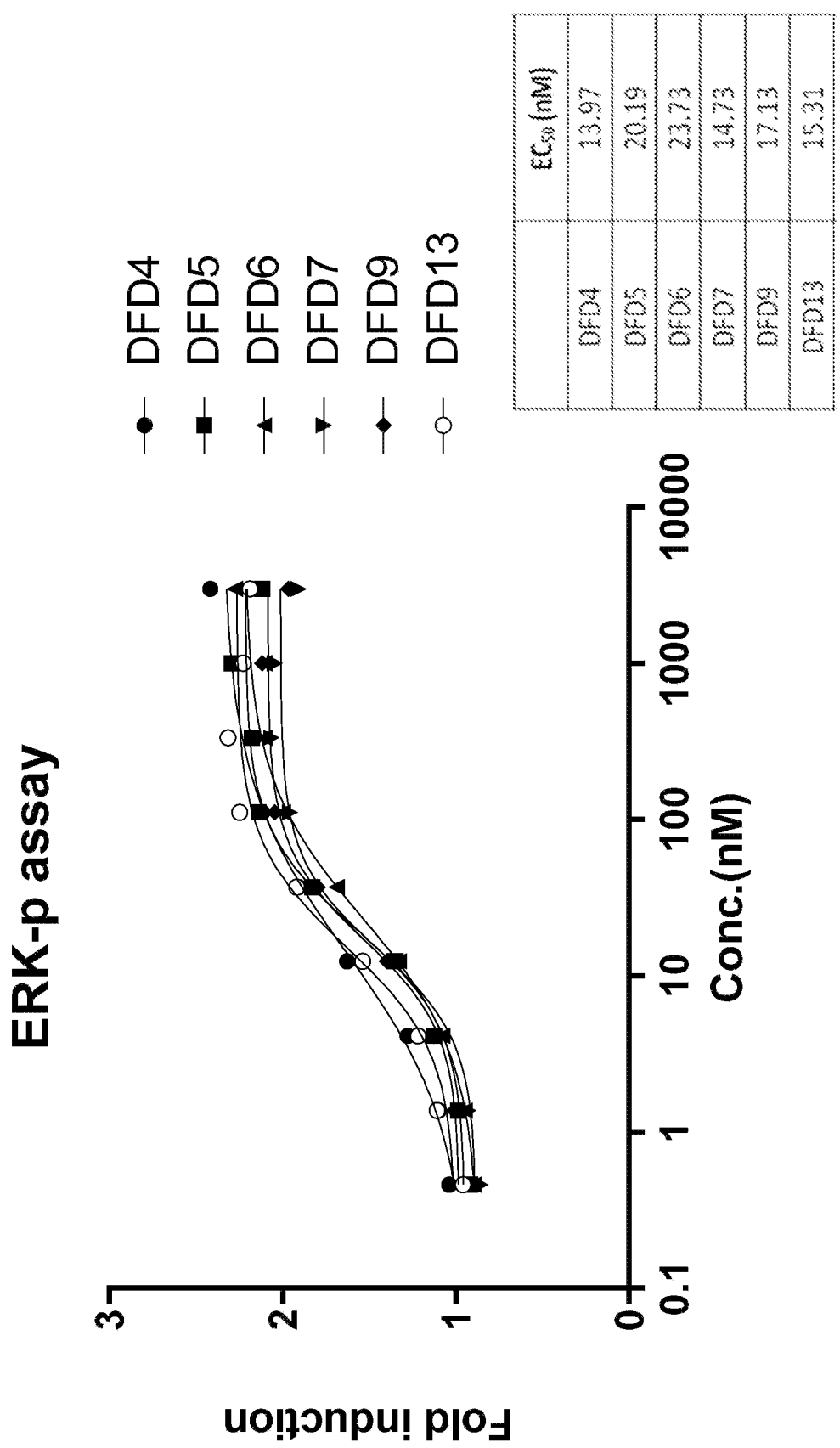
FIGS. 1A to 1C are graphs showing the in vitro activities of fusion proteins including FGF21 mutant proteins (hereinafter, "FGF21 mutant fusion protein") using a HEK293 cell line in which human β-klotho is overexpressed. No FGF21 mutant fusion proteins exhibited a significant decrease in activity due to the introduction of a mutation.

Hereinafter, the present invention will be described in more detail.

In an aspect, the present invention provides a dual function protein comprising a fibroblast growth factor 21 (FGF21) mutant protein; a biologically active protein, or a mutant or fragment thereof; and an Fc region of an immunoglobulin, wherein the FGF21 mutant protein comprises at least one mutation selected from the group consisting of the following mutations (1) to (7):

(1) a substitution of amino acids at positions 98 to 101 from the N-terminus of a wild-type FGF21 protein with an amino acid sequence of EIRP (SEQ ID NO: 68) (hereinafter, "EIRP");

(2) a substitution of amino acids at positions 170 to 174 from the N-terminus of a wild-type FGF21 protein with an amino acid sequence of TGLEAV (SEQ ID NO: 69) (hereinafter, "TGLEAV");

(3) a substitution of amino acids at positions 170 to 174 from the N-terminus of a wild-type FGF21 protein with an amino acid sequence of TGLEAN (SEQ ID NO: 70) (hereinafter, "TGLEAN");

(4) a substitution of an amino acid at position 170 from the N-terminus of a wild-type FGF21 protein with an amino acid N;

(5) a substitution of an amino acid at position 174 from the N-terminus of a wild-type FGF21 protein with an amino acid N;

(6) a substitution of an amino acid at position 180 from the N-terminus of a wild-type FGF21 protein with an amino acid E, along with one or more mutations (1) to (5) above; and (7) a mutation of 1 to 10 amino acids for reducing immunogenicity of a wild-type FGF21 protein.

The wild-type FGF21 protein, a hormone known to play an important role in glucose and lipid homeostasis, may be one derived from mammals such as humans, mice, pigs, monkeys, etc., preferably from humans. More preferably, the wild-type FGF21 protein may be the wild-type human FGF21 protein having an amino acid sequence represented by SEQ ID NO: 1.

The mutation included in the FGF21 mutant proteins may be, preferably, any one of the mutations of EIRP (SEQ ID NO: 68), TGLEAV (SEQ ID NO: 69), TGLEAN (SEQ ID NO: 70), G170N and G174N; a combination of any one of the mutations of TGLEAV (SEQ ID NO: 69), TGLEAN (SEQ ID NO: 70), G170N and G174N and the mutation of EIRP (SEQ ID NO: 68); a combination of any one of the mutations of EIRP (SEQ ID NO: 68), TGLEAV (SEQ ID NO: 69), TGLEAN (SEQ ID NO: 70), G170N and G174N and the mutation of A180E; or a combination of any one of the mutations of TGLEAV (SEQ ID NO: 69), TGLEAN (SEQ ID NO: 70), G170N and G174N, the mutation of EIRP (SEQ ID NO: 68) and the mutation of A180E. Furthermore, the FGF21 mutant proteins may have a conformation, in which 1 to 10 amino acids at the N-terminus or C-terminus is (are) deleted as compared to the wild-type FGF21 protein. More preferably, the FGF21 mutant proteins may include an amino acid sequence represented by any one of SEQ ID NO: 6 to 23. Still more preferably, the FGF21 mutant proteins may include an amino acid sequence represented by any one of SEQ ID NO: 6 to 23 and further have a conformation, in which 1 to 10 amino acids at the N-terminus or C-terminus is (are) deleted as compared to the wild-type FGF21 protein.

In the dual function protein, an amino acid residue N of FGF21 mutant protein introduced by a mutation may be glycosylated.

The biologically active protein may be one selected from the group consisting of insulin, C-peptide, leptin, glucagon, gastrin, gastric inhibitory polypeptide (GIP), amylin, calcitonin, cholecystokinin, peptide YY, neuropeptide Y, bone morphogenetic protein-6 (BMP-6), bone morphogenetic protein-9 (BMP-9), oxyntomodulin, oxytocin, glucagon-like peptide-1 (GLP-1), glucagon-like peptide-2 (GLP-2), irisin, fibronectin type III domain-containing protein 5 (FNDC5), apelin, adiponectin, C1q and tumor necrosis factor related protein (CTRP family), resistin, visfatin, omentin, retinol binding protein-4 (RBP-4), glicentin, angiopoietin, interleukin-22 (IL-22), exendin-4 and growth hormone. Preferably, the biologically active protein may be one selected from GLP-1, a mutant thereof and exendin-4.

The GLP-1 protein is an incretin hormone consisting of 31 amino acids, which is secreted by L cells in the intestinal tract stimulated by food, etc. For example, the GLP-1 protein may be represented by the amino acid sequence of SEQ ID NO: 42.

A mutant of GLP-1 may be represented, for example, by the amino acid sequence of any one of SEQ ID NO: 43 to 46.

As used herein, the term "Fc region," "Fc fragment," or "Fc" refers to a protein, which includes a heavy chain constant region 1 (CH1), a heavy chain constant region 2 (CH2) and a heavy chain constant region 3 (CH3) of an immunoglobulin, but does not include variable regions of the heavy and light chains and a light chain constant region 1 (CL1) of an immunoglobulin. Additionally, as used herein, the term "Fc region mutant" refers to one prepared by substituting part of amino acid(s) of an Fc region or by combining Fc regions of different types.

The Fc region of immunoglobulin may be an entire Fc region constituting an antibody, a fragment thereof, or an Fc region mutant. Additionally, the Fc region includes a molecule in the form of a monomer or multimer, and may further include a hinge region of the heavy chain constant region. The Fc region mutant may be modified to prevent cleavage at the hinge region. Furthermore, the hinge sequence of the Fc may have a substitution in some amino acid sequences to reduce antibody-dependent cell-mediated cytotoxicity (ADCC) or complement-dependent cytotoxicity (CDC). In addition, part of the amino acid sequence of the Fc hinge sequence may be substituted to inhibit the rearrangement of the Fab region. A lysine residue at the C-terminus of the Fc may be removed.

Preferably, the Fc region of immunoglobulin may be any one of IgG1, IgG2, IgG3, IgG4 and IgD Fc regions; or a hybrid Fc, which is a combination thereof. Further, the hybrid Fc may include an IgG4 region and an IgD region. Further, the hybrid Fc region may include part of the hinge sequence and CH2 of an IgD Fc, and CH2 and CH3 sequences of IgG4 Fc.

In addition, the Fc fragment of the present invention may be in the form of wild-type glycosylated chain, more glycosylated chain than the wild-type, less glycosylated chain than the wild-type, or deglycosylated chain. The increase, decrease, or removal of glycosylated chain may be performed by a conventional method known in the art, such as a chemical method, an enzymatic method, and a genetic engineering method using microorganisms.

Preferably, the immunoglobulin Fc region may be represented by an amino acid sequence selected from SEQ ID NO. 24 to 26, 47 and 48.

The dual function protein may include a biologically active protein, an Fc region of an immunoglobulin and an FGF21 mutant protein, linked in this order from the N-terminus to the C-terminus. Further, the dual function protein may include an FGF21 mutant protein, an Fc region of an immunoglobulin and a biologically active protein, linked in this order from the N-terminus to the C-terminus. Preferably, the dual function protein may include a biologically active protein, an Fc region of an immunoglobulin and an FGF21 mutant protein, linked in this order from the N-terminus to the C-terminus.

Furthermore, the dual function protein may include a GLP-1 mutant protein, an Fc region of an immunoglobulin and an FGF21 mutant protein, linked in this order from the N-terminus to the C-terminus. Further, the dual function protein may include an FGF21 mutant protein, an Fc region of an immunoglobulin and a GLP-1 mutant protein, linked in this order from the N-terminus to the C-terminus. Preferably, the dual function protein may include a GLP-1 mutant protein, an Fc region of an immunoglobulin and an FGF21 mutant protein, linked in this order from the N-terminus to the C-terminus.

Additionally, the dual function protein may further include a linker.

The dual function protein may be in the form, in which the FGF21 mutant protein is directly connected to the N-terminus or C-terminus of the immunoglobulin Fc region, or the FGF21 mutant protein is connected to the immunoglobulin Fc region via a linker.

In such case, the linker may be connected to the N-terminus, C-terminus, or a free radical of the Fc fragment, and also, may be connected to the N-terminus, C-terminus, or a free radical of the FGF21 mutant protein. When the linker is a peptide linker, the connection may occur in any region. For example, the linker may be connected to the C-terminus of the immunoglobulin Fc region and the N-terminus of the FGF21 mutant protein to form a fusion protein of the immunoglobulin Fc region and the FGF21 mutant protein.

Furthermore, the dual function protein of the present invention may be in the form, in which a biologically active protein is linked to the N-terminus of the Fc region of immunoglobulin of the fusion protein.

When the linker and Fc are separately expressed and then connected, the linker may be a crosslinking agent known in the art. Examples of the crosslinking agent may include 1,1-bis(diazoacetyl)-2-phenylethane, glutaraldehyde, imidoesters including N-hydroxysuccinimide ester such as 4-azidosalicylic acid and disuccinimidyl esters such as 3,3'-dithiobis(succinimidylpropionate), and bifunctional maleimides such as bis-N-maleimido-1,8-octane, but are not limited thereto.

Further, the linker may be a peptide. Preferably, the linker may be a peptide consisting of 10 to 30 amino acid residues.

Furthermore, alanine may additionally be attached to the end of linker. Preferably, the linker may be a peptide having an amino acid sequence represented by any one of SEQ ID NO: 2 to 5.

The dual function protein may be in a form in which a dimer or multimer of FGF21 mutant proteins, in which one or more FGF21 mutant proteins linked together, is connected to an immunoglobulin Fc region. Additionally, the dual function protein may be in a form of a dimer or multimer in which two or more immunoglobulin Fc regions are linked, wherein the immunoglobulin Fc regions have the FGF21 mutant protein connected thereto.

Additionally, the dual function protein may be a peptide which preferably has an amino acid sequence represented by any one of SEQ ID NO: 58 to 67. More preferably, the dual function protein may be a peptide which has an amino acid sequence represented by SEQ ID NO: 65, 66 or 67.

The FGF21 mutant protein may further include a mutation of 1 to 10 amino acids for reducing immunogenicity of the wild-type FGF21 protein. The immunogenicity may be predicted by a conventional method known in the art. For example, the potential immunogenicity of a protein may be screened by using, e.g., ITOPE™ and TCED™ methods.

Further, the mutation for minimizing the immunogenicity may be designed by a conventional method known in the art. For example, when immunogenicity is observed by performing an EPISCREEN™ analysis to evaluate potential immunogenicity, the amino acid sequences inducing the immunogenicity may be identified through T-cell epitope mapping, and the mutants with minimized immunogenicity may be designed via in silico prediction.

In another aspect, the present invention provides a pharmaceutical composition containing the dual function protein for treating FGF21-associated disorders.

As used herein, the term "FGF21-associated disorder" may include obesity, type I- and type II diabetes, pancreatitis, dyslipidemia, non-alcoholic fatty liver disease (NAFLD), non-alcoholic steatohepatitis (NASH), insulin resistance, hyperinsulinemia, glucose intolerance, hyperglycemia, metabolic syndrome, acute myocardial infarction, hypertension, cardiovascular diseases, atherosclerosis, peripheral arterial disease, apoplexy, heart failure, coronary artery heart disease, renal disease, diabetic complications, neuropathy, gastroparesis, disorder associated with a serious inactivation mutation in insulin receptor, and other metabolic disorders. Preferably, the FGF21-associated disorder may be diabetes, obesity, dyslipidemia, metabolic syndrome, non-alcoholic fatty liver disease, non-alcoholic steatohepatitis or cardiovascular diseases.

Further, the pharmaceutical composition may further include a pharmaceutical carrier. The pharmaceutical carrier may be any carrier as long as it is a non-toxic material suitable for delivering antibodies to patients. For example, distilled water, alcohol, fats, waxes and inactive solids may be included as a carrier. Pharmaceutically acceptable adjuvants (buffering agents, dispersants) may also be included in the pharmaceutical composition. In these formulations, the concentration of the dual function protein may vary greatly.

Specifically, the pharmaceutical composition may contain a formulation material for altering, maintaining, or conserving the pH, osmolarity, viscosity, transparency, color, isotonicity, odor, sterility, stability, dissolution or release rate, adsorption, or permeability of the composition. Examples of the suitable formulating material may include amino acids (e.g., glycine, glutamine, asparagine, arginine or lysine), anti-microorganism agents, anti-oxidants (e.g., ascorbic acid, sodium sulfite or sodium bisulfite), buffering agents (e.g., borate, bicarbonates, Tris-HCl, citrate, phosphate or other organic acids), bulking agents (e.g., mannitol or glycine), chelating agents (e.g., ethyelenediaminetetraacetic acid (EDTA)), complexing agents (e.g., caffeine, polyvinylpyrrolidione, β-cyclodextrin or hydroxypropyl-β-cyclodextrin), fillers, monosaccharides, disaccharides and other carbohydrates (e.g., glucose, mannose or dextrin), proteins (e.g., serum albumin, gelatin or immunoglobulin), coloring agents, flavoring agents, diluents, emulsifiers, hydrophilic polymers (e.g., polyvinylpyrrolidione), low molecular weight polypeptides, salt-forming counterions (e.g., sodium), preservatives (e.g., benzalkonium chloride, benzoic acid, salicylic acid, thimerosal, phenethyl alcohol, methylparaben, propylparaben, chlorhexidine, sorbic acid or hydrogen peroxide), solvents (e.g., glycerin, propylene glycol or polyethylene glycol), sugar alcohols (e.g., mannitol or sorbitol), suspending agents, surfactants or humectants (e.g., pluronics; PEG; sorbitan ester; polysorbate, e.g., polysorbate 20 or polysorbate 80; triton; tromethamine; lecithin; cholesterol or tyloxapol), stability improvers (e.g., sucrose or sorbitol), growth improvers (e.g., alkali metal halides, preferably, sodium chloride or potassium chloride; or mannitol, sorbitol), delivery vehicles, diluents, excipients and/or pharmaceutical adjuvants, but are not limited thereto.

In another aspect, the present invention provides a method for preventing or treating FGF21-associated disorders including administering the dual function protein to a subject in need of such prevention or treatment. This method includes, in particular, administering an effective amount of the dual function protein of the present invention to a mammal having a symptom of diabetes, obesity, dyslipidemia, metabolic syndrome, non-alcoholic fatty liver disease, non-alcoholic steatohepatitis or cardiovascular diseases which are FGF21-associated disorders.

The pharmaceutical composition of the present invention may be administered via any route. The composition of the present invention may be provided to an animal directly (e.g., topically, by administering into tissue areas by injection, transplantation, or by topical administration) or systemically (e.g., by oral- or parenteral administration) via any appropriate means. When the composition of the present invention is parenterally provided via intravenous-, subcutaneous-, ophthalmic-, intraperitoneal-, intramuscular-, oral-, rectal-, intraorbital-, intracerebral-, intracranial-, intraspinal-, intraventricular-, intrathecal-, intracisternal-, intracapsular-, intranasal-, or aerosol administration, the composition is preferably aqueous or may include a portion of a physiologically applicable body liquid suspension or solution. Accordingly, the carrier or vehicle may be added to the composition and be delivered to a patient since it is physiologically applicable. Therefore, a physiologically-appropriate saline solution may generally be included as a carrier like a body fluid for formulations.

Further, the administration frequency may vary depending on the pharmacokinetic parameters of the dual function protein in the formulations to be used. Typically, physicians would administer the composition until an administration dose to achieve a desired effect is reached. Accordingly, the composition may be administered as a unit dose, at least two doses with time intervals (may or may not contain the same amount of a target dual function protein) or administered by a continuous injection via a transplantation device or catheter. The precision of addition of an appropriate administration dose may be routinely performed by those skilled in the art, and corresponds to the scope of work being routinely performed by them.

Additionally, the preferable unit dose of the dual function protein in humans may be in a range from 0.01 μg/kg to 100 mg/kg of body weight, and more preferably from 1 μg/kg to 10 mg/kg of body weight. Although this is the optimal amount, the unit dose may vary depending on the disease to be treated or the presence/absence of adverse effects. Nevertheless, the optimal administration dose may be determined by performing a conventional experiment. The administration of the dual function protein may be performed by a periodic bolus injection, an external reservoir (e.g., an intravenous bag), or a continuous intravenous-, subcutaneous-, or intraperitoneal administration from the internal source (e.g., a bioerodable implant).

In addition, the dual function protein of the present invention may be administered to a subject recipient along with other biologically active molecules. The optimal combination of the dual function protein and other molecule(s), dosage forms, and optimal doses may be determined by a conventional experiment well known in the art.

In still another aspect, the present invention provides an isolated nucleic acid molecule encoding the dual function protein.

As used herein, the term "isolated nucleic acid molecule" refers to a nucleic acid molecule of the present invention, which is isolated from about at least 50% of proteins, lipids, carbohydrates, or other materials, discovered in nature when total nucleic acids are isolated from a source cell; which is operatively linked to a polynucleotide which is not linked in nature; or which is a part of a larger polynucleotide sequence and does not occur in nature. Preferably, in the isolated nucleic acid molecules of the present invention, there are not substantially present any other contaminated nucleic acids, or other contaminants which are discovered in the natural environment and inhibit uses of the nucleic acids in the production of polypeptides, or treatment, diagnosis, prevention, or research.

In such case, the isolated nucleic acid molecules encoding the dual function protein may have different sequences with each other due to codon redundancy. Furthermore, as long as the isolated nucleic acid can produce the dual function protein, the isolated nucleic acid may be appropriately modified, or a nucleotide may be added to the N-terminus or C-terminus of the isolated nucleic acid according to desired purposes.

The isolated nucleic acid may include, for example, a nucleotide sequence represented by any one of SEQ ID NO: 71 to 80.

In still another aspect, the present invention provides an expression vector comprising the isolated nucleic acid molecule.

As used herein, the term "expression vector" refers to a vector containing a nucleic acid sequence, which is suitable for the transformation of a host cell and directs or controls the expression of an inserted heterogenous nucleic acid sequence. The expression vector includes a linear nucleic acid, a plasmid, a phagemid, a cosmid, an RNA vector, a viral vector, and analogs thereof. Examples of the viral vector include a retrovirus, an adenovirus and an adeno-associated virus, but are not limited thereto.

As used herein, the term "expression of a heterogeneous nucleic acid sequence" or "expression" of a target protein refers to transcription of an inserted DNA sequence, translation of an mRNA transcript, and production of an Fc fusion protein product, an antibody or an antibody fragment.

A useful expression vector may be RcCMV (Invitrogen, Carlsbad) or a mutant thereof. The useful expression vector may include a human cytomegalovirus (CMV) promoter for promoting a continuous transcription of a target gene in a mammalian cell, and a bovine growth hormone polyadenylation signal sequence for enhancing the level of post-transcriptional RNA stability. In an exemplary embodiment of the present invention, the expression vector is pAD15, which is a modified vector of RcCMV.

In still another aspect, the present invention provides a host cell comprising the expression vector.

As used herein, the term "host cell" refers to a prokaryotic cell or eukaryotic cell into which a recombinant expression vector may be introduced. As used herein, the term "transformed" or "transfected" refers to introduction of a nucleic acid (e.g., a vector) into a cell by various technologies known in the art.

An appropriate host cell may be transformed or transfected with a DNA sequence of the present invention and may be used for the expression and/or secretion of the target protein. Examples of the appropriate host cell that may be used in the present invention include immortal hybridoma cells, NS/0 myeloma cells, 293 cells, Chinese hamster ovary (CHO) cells, HeLa cells, CAP cells (human amniotic fluid-derived cells), and COS cells.

Hereinafter, exemplary embodiments of the present invention will be described in detail with reference to the examples. However, these examples according to the present invention can be modified in many different forms and the scope of the present invention should not be construed as limited to the examples set forth herein.

MODE FOR THE INVENTION

Preparation Example 1. Preparation and Purification of Fusion Protein Containing FGF21 Mutant Protein Preparation Example 1-1. Preparation of Expression Vectors for Expression of FGF21 Mutant Proteins In order to improve the stability, activity and pharmacokinetic profiles of the FGF21 in an Fc-FGF21 structure, mutation studies of FGF21 were performed.

Specifically, mutant proteins were designed for the LLLE (SEQ ID NO: 81) region (the amino acids at positions 98 to 101 from the N-terminus of the FGF21 protein) and GPSQG (SEQ ID NO: 82) region (the amino acids at positions 170 to 174 from the N-terminus of the FGF21 protein), and A180 site, which were expected to significantly affect protein activities based on 3-dimensional structure analysis of the FGF21 proteins.

The position, sequence information, target and expected effect of each mutation introduced into the FGF21 protein are listed in Table 1 below (in Table 1, N refers to glycosylated asparagine (N)). Further, FGF21 mutant proteins including the mutations described in Table 1 are listed in Table 2 below.

TABLE 1

| Sequence | Position | Original sequence | Mutated sequence | Target | Expected effect |
|---|---|---|---|---|---|
| EIRP (SEQ ID NO: 68) | 98-101 | LLLE (SEQ ID NO: 81) | EIRP (SEQ ID NO: 68) | Substitution with FGF19 sequence | Improvement of stability and pharmacokinetics |
| TGLEAV (SEQ ID NO: 69) | 170-174 | GPSQG (SEQ ID NO: 82) | TGLEAV (SEQ ID NO: 69) | Substitution with FGF19 sequence | Improvement of pharmacokinetics |
| TGLEAN (SEQ ID NO: 70) | 170-174 | GPSQG (SEQ ID NO: 82) | TGLEA<u>N</u> (SEQ ID NO: 70) | Substitution with FGF19 sequence, and addition of N-glycosylation | Improvement of pharmacokinetics |
| G170N | 170 | G | <u>N</u> | Point mutation, and addition of N-glycosylation | Improvement of pharmacokinetics |

TABLE 1-continued

| Sequence | Position | Original sequence | Mutated sequence | Target | Expected effect |
|---|---|---|---|---|---|
| G174N | 174 | G | N | Point mutation, and addition of N-glycosylation | Improvement of pharmacokinetics |
| A180E | 180 | A | E | Point mutation | Improvement of pharmacokinetics |

TABLE 2

| SEQ ID NO | Sequence of FGF21 mutant protein |
|---|---|
| 6 | FGF21 (EIRP) |
| 7 | FGF21 (TGLEAV) |
| 8 | FGF21 (TGLEAN) |
| 9 | FGF21 (G170N) |
| 10 | FGF21 (G174N) |
| 11 | FGF21 (EIRP, TGLEAV) |
| 12 | FGF21 (EIRP, TGLEAN) |
| 13 | FGF21 (EIRP, G170N) |
| 14 | FGF21 (EIRP, G174N) |
| 15 | FGF21 (EIRP, A180E) |
| 16 | FGF21 (TGLEAV, A180E) |
| 17 | FGF21 (TGLEAN, A180E) |
| 18 | FGF21 (G170N, A180E) |
| 19 | FGF21 (G174N, A180E) |
| 20 | FGF21 (EIRP, TGLEAV, A180E) |
| 21 | FGF21 (EIRP, TGLEAN, A180E) |
| 22 | FGF21 (EIRP, G170N, A180E) |
| 23 | FGF21 (EIRP, G174N, A180E) |

Expression vectors were prepared to express the amino acids of the three components: fusion carrier, linker and FGF21 mutant in this order from the N-terminus to C-terminus. The material code of each FGF21 mutant fusion protein, sequence of mutation introduced into FGF21, sequence of fusion carrier and linker sequence are listed in Table 3 below (in Table 3, N refers to glycosylated asparagine (N)).

TABLE 3

| SEQ ID NO | Material code | Sequence of FGF21 mutation | Fusion carrier | Linker sequence |
|---|---|---|---|---|
| 27 | DFD1 | EIRP, TGLEAV | hyFc (SEQ ID NO: 26) | C (SEQ ID NO: 2) |
| 28 | DFD3 | TGLEAV | hyFc (SEQ ID NO: 26) | AKA (SEQ ID NO: 3) |
| 29 | DFD4 | TGLEAV | hyFc (SEQ ID NO: 26) | GS3 (SEQ ID NO: 4) |
| 30 | DFD5 | TGLEAN | hyFc (SEQ ID NO: 26) | GS3 (SEQ ID NO: 4) |
| 31 | DFD6 | G170N | hyFc (SEQ ID NO: 26) | GS3 (SEQ ID NO: 4) |
| 32 | DFD6 (E. coli) | G170N | hyFc (SEQ ID NO: 26) | GS3 (SEQ ID NO: 4) |
| 33 | DFD7 | G174N | hyFc (SEQ ID NO: 26) | GS3 (SEQ ID NO: 4) |
| 34 | DFD9 | none | hyFc (SEQ ID NO: 26) | GS3 (SEQ ID NO: 4) |
| 35 | DFD13 | EIRP, TGLEAV | hyFc (SEQ ID NO: 26) | GS3 (SEQ ID NO: 4) |
| 36 | DFD18 | EIRP, TGLEAV, A180E | hyFc (SEQ ID NO: 26) | GS3 (SEQ ID NO: 4) |
| 37 | DFD72 | EIRP, TGLEAN, A180E | hyFc (SEQ ID NO: 26) | GS3 (SEQ ID NO: 4) |
| 38 | DFD73 | EIRP, G170N | hyFc (SEQ ID NO: 26) | GS3 (SEQ ID NO: 4) |
| 39 | DFD74 | EIRP, G170N, A180E | hyFc (SEQ ID NO: 26) | GS3 (SEQ ID NO: 4) |
| 40 | RGE (Amgen) | L98R, P171G, A180E | IgG1Fc mutant | GS3 (SEQ ID NO: 4) |
| 41 | Fc-FGF21 (Lilly) | X | IgG4Fc mutant (SEQ ID NO: 25) | GS3A (SEQ ID NO: 5) | added to the 5' terminus and 3' terminus of the nucleotide sequences encoding each of the FGF21 mutant proteins and an initiation codon for protein translation and a leader sequence (MDAMLRGLCCVLLLCGAVFVSPSHA) (SEQ ID NO: 83) capable of secreting the expressed protein to the outside of a cell were inserted next to the restriction enzyme sequence at the 5' terminus. A termination codon was inserted next to the nucleotide sequence, which encodes each of the FGF21 mutant fusion proteins. The nucleotide sequence encoding each of the FGF21 mutant fusion proteins was cloned into a pTrans-empty expression vector by using the two restriction enzymes of NheI and NotI. The pTrans-empty expression vector, which has a simple structure including a CMV promoter, a pUC-derived replication origin, an SV40-derived replication origin and an ampicillin-resistant gene, was purchased from CEVEC Pharmaceuticals (Germany).

In the case of the fusion proteins of DFD6 (*E. coli*) and RGE (Amgen), the nucleotide sequence encoding each fusion protein was inserted into a pET30a expression vector for expression in *E. coli*.

Preparation Example 1-2. Construction of Plasmid DNA for Expression of FGF21 Mutant Fusion Proteins

*E. coli* was transformed with each of the expression vectors constructed in Preparation Example 1-1 to obtain a In order to produce the FGF21 mutant fusion proteins, the nucleotide sequences encoding each of the FGF21 mutant proteins were synthesized by consulting with Bioneer Corporation (Korea) based on the amino acid sequence of each protein. NheI and NotI restriction enzyme sequences were large amount of plasmid DNA to be used for expression. *E. coli* cells, whose cell walls were weakened, were transformed with each expression vector through heat shock, and the transformants were plated out on LB plates to obtain colonies. The colonies thus obtained were inoculated into LB media, cultured at 37° C. for 16 hours, and each *E. coli* culture containing each expression vector was obtained in a volume of 100 mL. The *E. coli* thus obtained was centrifuged to remove the culture medium, and then P1, P2, P3 solutions (QIAGEN, Cat No.: 12963) were added to break the cell walls, thereby obtaining a DNA suspension in which proteins and DNAs were separated. Plasmid DNA was purified from the DNA suspension thus obtained by using a Qiagen DNA purification column. The eluted plasmid DNA was identified through an agarose gel electrophoresis, and concentrations and purities were measured by using a NANODROPT™ device (Thermo scientific, NANO-DROP™ Lite). The DNA thus obtained was used for expression.

Preparation Example 1-3. Expression of Fusion Proteins in CAP-T Cells

Human cell lines were transfected with each plasmid DNA type obtained in Preparation Example 1-2. Each plasmid DNA type was transduced into CAP-T cells (CEVEC), which had been cultured in PEM medium (Life technologies), by using PEI solution (Polyplus, Cat. No.: 101-10N). The mixed solution of DNA and the PEI solution was mixed with the cell suspension by using a FREESTYLE™ 293 expression medium (Invitrogen), cultured at 37° C. for 5 hours, and PEM medium was added. After culturing at 37° C. for 5-7 days, the culture was centrifuged to remove cells and a supernatant including FGF21 mutant fusion proteins was obtained.

Preparation Example 1-4. Expression and Purification of FGF21 Mutant Fusion Proteins in *E. coli*

*E. coli* strain BL21 (DE3) was transformed with each plasmid DNA expressing DFD6 (*E. coli*) and RGE (Amgen) fusion proteins. The transformed *E. coli* expressing each fusion protein was inoculated into 20 mL of LB media, cultured at 37° C. for 15 hours with shaking, and then a portion of the culture media was inoculated into 100 mL of LB media, and cultured at 37° C. for 16 hours with shaking. Upon completion of culturing, the culture was centrifuged to obtain *E. coli* pellets, and then cells were disrupted using a high pressure cell disruptor to obtain inclusion bodies.

The obtained inclusion bodies were purified by washing and elution, followed by a protein refolding process. Specifically, the obtained inclusion bodies were washed 2-3 times with a buffer solution (pH 8.0) containing 0.5% Triton X-100, 50 mM Tris, 1 mM EDTA and 0.1 M NaCl to remove bacterial protein, and then resuspended in 8 M urea buffer containing 8 M urea, 50 mM Tris and 1 mM DTT. Since the proteins in 8 M urea buffer were completely denatured, a protein refolding process was performed as follows.

To begin, 8 M urea buffer was gradually diluted with 20 mM glycine buffer solution (pH 9.0) to remove urea, and from the concentration of 2 M, $CuSO_4$ was added to the concentration of 80 µM to induce stable protein folding. The protein completing the refolding process was suspended in PBS buffer solution (pH 7.4), and the suspension was filtered with a 0.22 µm filter to remove impurities, and then loaded into a Protein A affinity chromatography column. The column was washed with 1×PBS buffer solution (pH 7.4) and then the proteins were eluted using 100 mM glycine buffer solution (pH 3.0) to prepare DFD6 (*E. coli*) fusion protein.

In the case of RGE (Amgen) fusion protein, the protein completing the refolding process was suspended in 50 mM Tris buffer solution (pH 8.0), the suspension was filtered with a 0.22 µm filter to remove impurities, and then loaded into an anion exchange resin column (POROS® HQ 50 µm, Thermo Fisher Scientific). The column was washed with 50 mM Tris buffer solution (pH 8.0), and then 50 mM Tris buffer solution (pH 8.0) was administered along the concentration gradient to elute RGE (Amgen) fusion protein. The RGE (Amgen) fusion protein obtained by the anion exchange resin was mixed with ammonium sulfate to the concentration of 1 M, and then purified using a hydrophobic interaction chromatography column (Phenyl sepharose FF, GE Healthcare). Specifically, the column was washed with 50 mM Tris buffer solution (pH 8.0) containing 1 M ammonium sulfate, 50 mM Tris buffer solution (pH 8.0) was administered along the concentration gradient, and the eluted fractions were analyzed through 10% Tris-glycine gel electrophoresis. The gel was dyed with coomassie brilliant blue R with mild shaking, and the fractions containing FGF21 mutant fusion protein with high purity were collected and then dialyzed overnight at 4° C. using a final buffer solution (1×PBS, 1 mM EDTA, pH 7.4). Upon completion of the dialysis, the obtained protein stock solution was concentrated at 3,000 rpm by using a 30,000 MW cut-off centrifugation filter at 4° C. The concentration of FGF21 mutant fusion protein was measured via BCA quantitative analysis.

Preparation Example 1-5. Purification of FGF21 Mutant Fusion Proteins

Protein A affinity chromatography column (GE Healthcare) was equilibrated with 1×PBS buffer solution (pH 7.4). The culture supernatant including each FGF21 mutant fusion protein obtained in Preparation Example 1-3 was filtered with a 0.2 µm filter, and then loaded into a Protein A affinity chromatography column. The column was washed with 1×PBS buffer solution (pH 7.4) and then proteins were eluted using 100 mM glycine buffer solution (pH 3.0). The fusion proteins obtained by affinity chromatography were purified using an anion exchange resin column (POROS® HQ 50 µm, Thermo Fisher Scientific). The anion exchange resin column was equilibrated with 50 mM Tris buffer solution (pH 8.0), before the FGF21 mutant fusion proteins were eluted from the column. Specifically, after washing the column with 50 mM Tris buffer solution (pH 8.0), 50 mM Tris buffer solution (pH 8.0) was dispensed along the concentration gradient and the eluted fractions were analyzed. Each eluted fraction was analyzed using size exclusion chromatography (SEC-HPLC), and the fractions including FGF21 mutant fusion proteins with high purity were collected. The concentration and quantitative analysis were performed in accordance with the methods described in Preparation Example 1-4.

Experimental Example 1. In Vitro Activities of Fusion Proteins

Experimental Example 1-1. Effect of FGF21 Mutations on Protein Activity

The in vitro activities of fusion proteins DFD4, DFD5, DFD6, DFD6 (*E. coli*), DFD7, DFD9, DFD13, DFD18, DFD72, DFD73 and DFD74 prepared in Preparation Example 1 were measured.

Specifically, the in vitro FGF21 activities of the fusion proteins were evaluated using a HEK293 cell line (Yuhan Corporation, Korea) which was modified to overexpress human β-klotho, a coreceptor of FGF21. For the evaluation of activity, the concentrates containing the fusion proteins prepared in Preparation Examples 1-4 and 1-5 were subjected to a 3-fold serial dilution at a concentration of 3 μM. After having been cultured in a serum-deficient state for 5 hours, the cell line overexpressing human β-klotho was treated with the diluted fusion proteins for 20 minutes, and then was lysed by adding cytolysis buffer (Cisbio/Cat #64ERKPEG) with stirring at 60 rpm for 30 minutes at room temperature. The cell lysate solution was mixed with antibodies (Cisbio/Cat #64ERKPEG), which can detect extracellular signal-regulated kinase (ERK) and phosphorylated ERK, and the mixture was maintained at room temperature for 2 hours. Fluorescence was detected using a fluorometric detector (TECAN/GENiosPro). The activities of the fusion proteins were measured by comparing their $EC_{50}$ values.

Figure 1B:
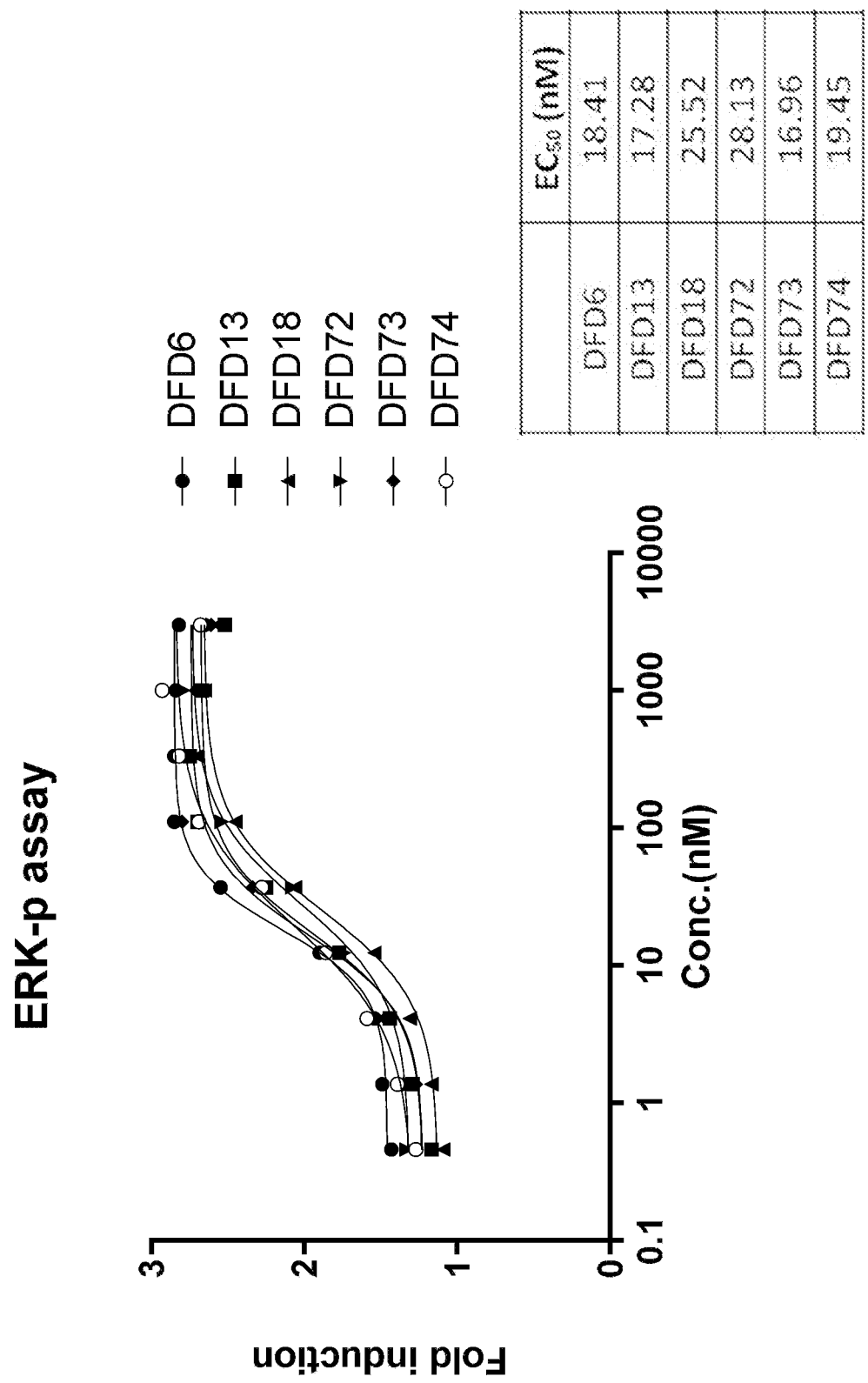
Figure 1C:
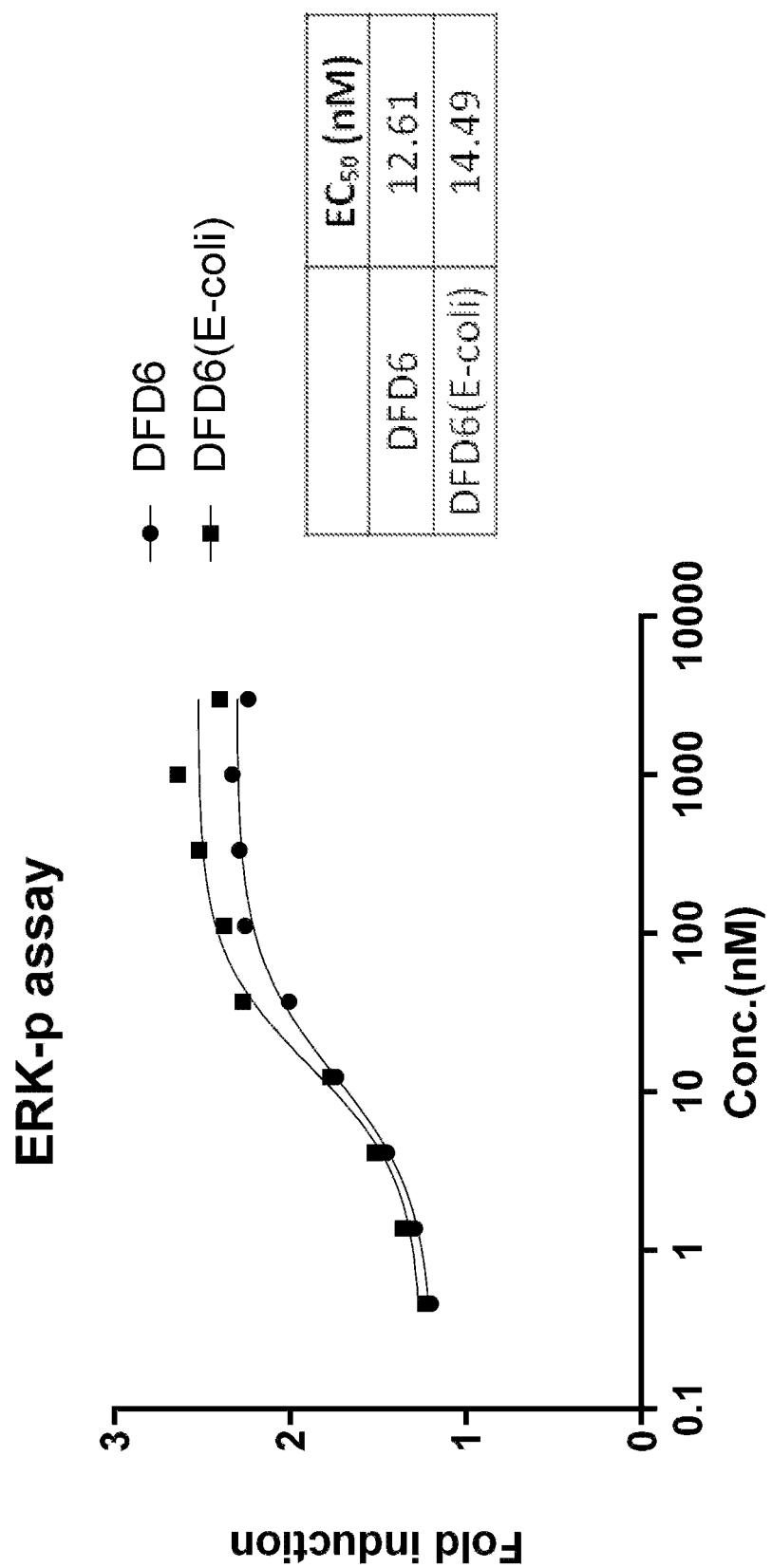

As shown in FIGS. 1A to 1C, it was confirmed that the in vitro activities of the fusion proteins prepared by introducing mutation sequences into the wild-type FGF21 protein were not inhibited, and the activities of each fusion protein were similar to each other. It was also confirmed that through the DFD6 (*E. coli*) sample expressed in *E. coli* and the DFD6 sample expressed in animal cells, the in vitro activities of the fusion proteins prepared by introducing N-glycosylation mutation into the wild-type FGF21 protein were not inhibited.

Experimental Example 1-2. Effect of Linker Sequence on Protein Activity

The in vitro activities of fusion proteins DFD1, DFD3, DFD4 and DFD13 prepared in Preparation Example 1 were measured.

Specifically, the FGF21 activities of the fusion proteins were measured by using the concentrates containing the fusion proteins prepared in Preparation Example 1-5 in accordance with the methods described in Experimental Example 1-1. The results are shown in FIGS. 2A and 2B.

Figure 2A:
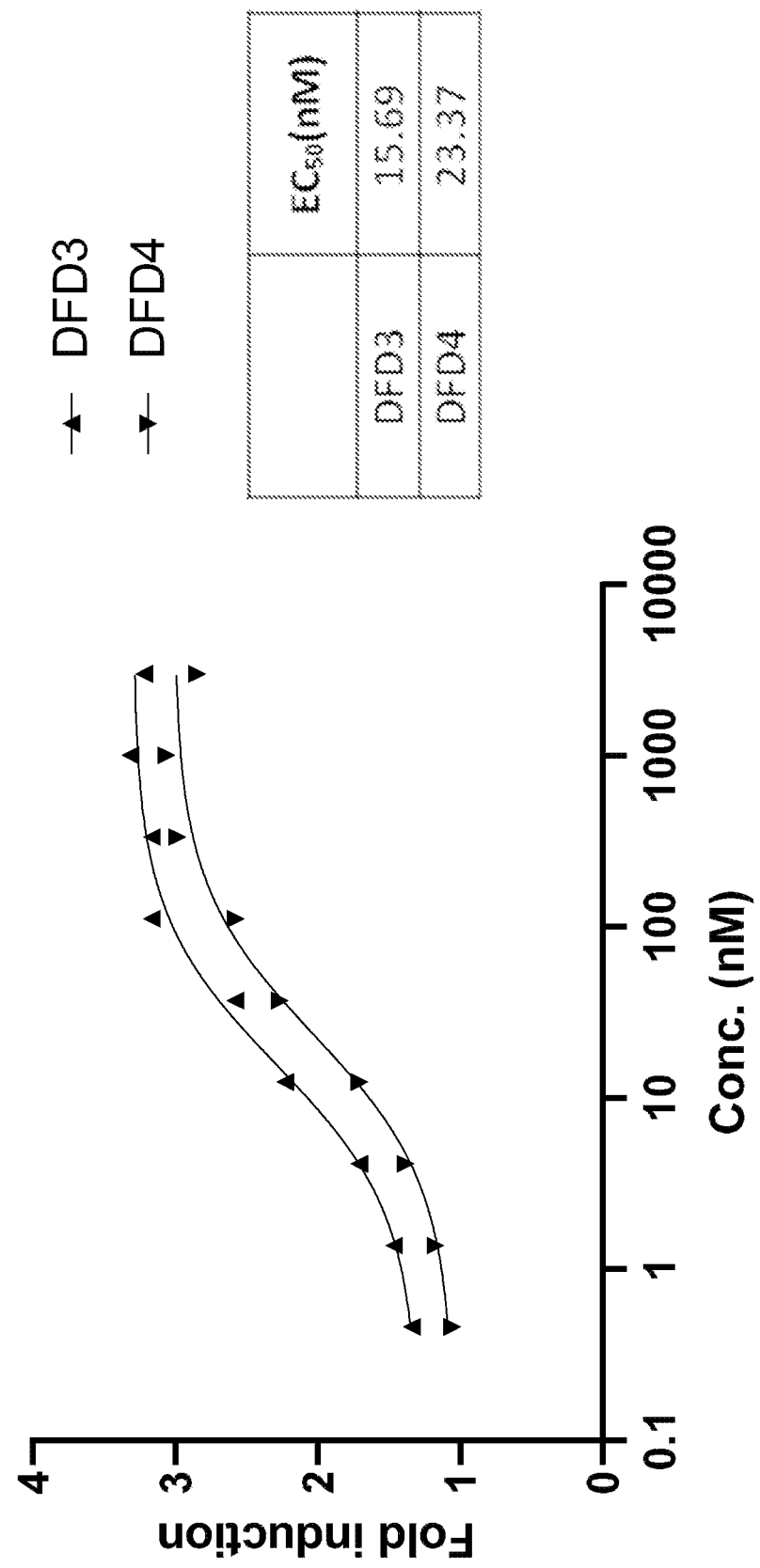
FIGS. 2A and 2B are graphs showing the in vitro activities of FGF21 mutant fusion proteins with various linkers connecting the N-terminus of FGF21 to an Fc region, using a HEK293 cell line in which human β-klotho is overexpressed. No FGF21 mutant fusion protein exhibited a significant decrease in activity, although a slight difference was shown in activity depending on the linker sequence.
Figure 2B:
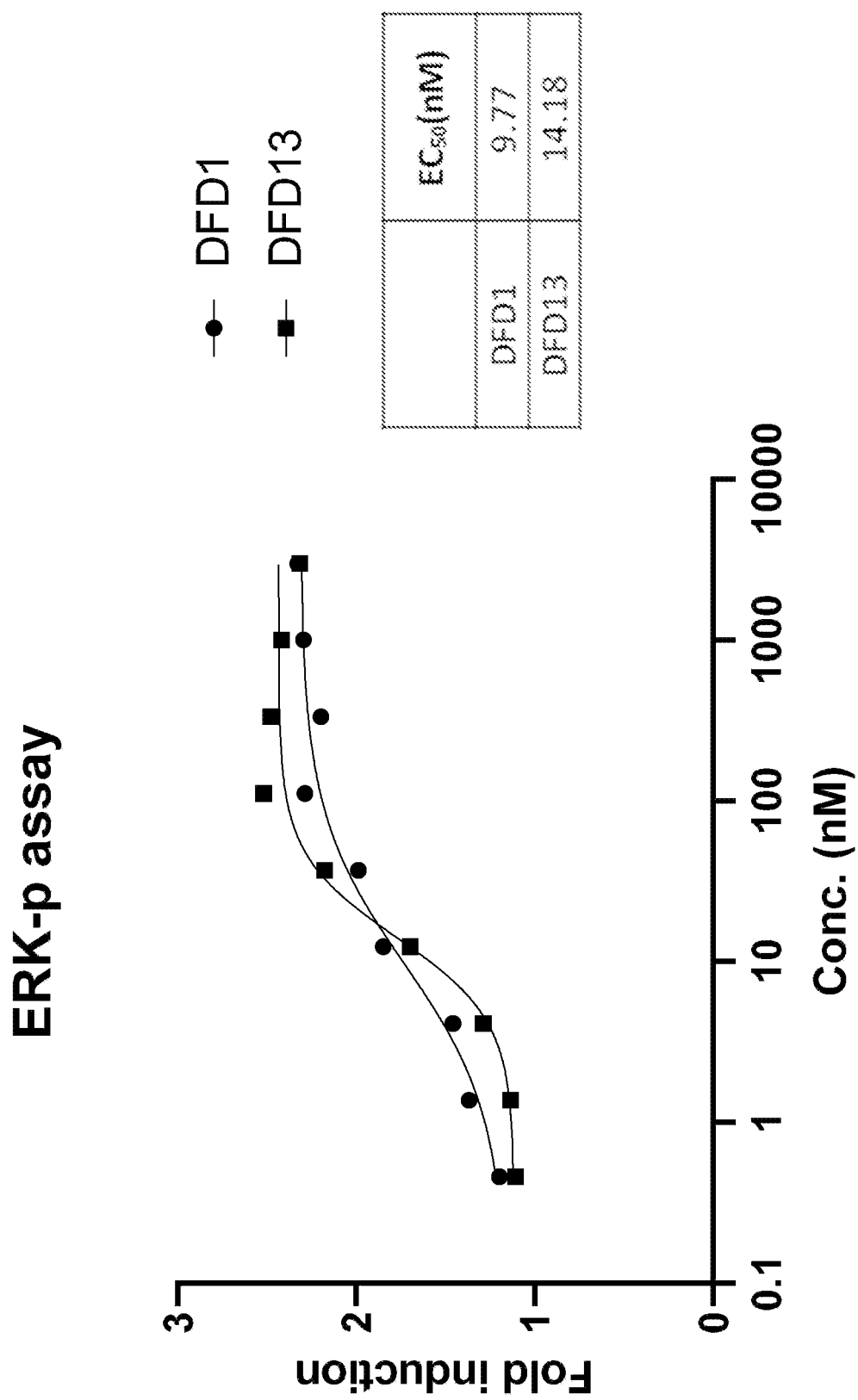

It was confirmed that no FGF21 mutant fusion protein showed a significant decrease in the activity, although a slight difference was shown in the activity depending on the linker sequence, as shown in FIGS. 2A and 2B.

Experimental Example 1-3. Experimental Results for DFD1, RGE (Amgen) and Fc-FGF21 (Lilly)

The in vitro activities of fusion protein DFD1 prepared in Preparation Example 1 and control proteins RGE (Amgen) and Fc-FGF21 (Lilly) were measured.

Specifically, the FGF21 activities of the fusion proteins were measured by using the concentrates containing the fusion proteins prepared in Preparation Example 1-5 and the control proteins in accordance with the methods described in Experimental Example 1-1. The results are shown in FIG. 3.

Figure 3:
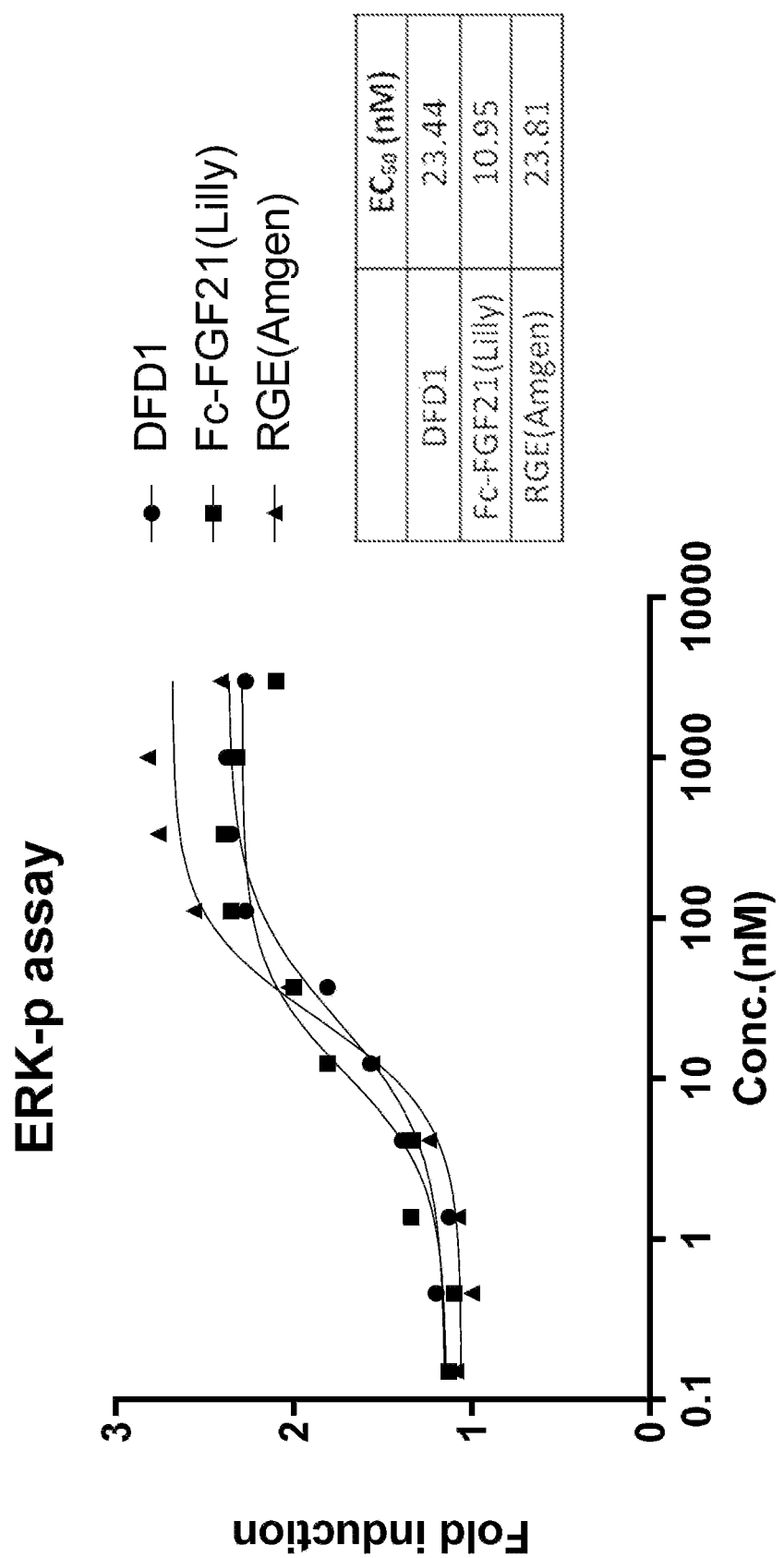
FIG. 3 is a graph showing the in vitro activities of RGE (Amgen), Fc-FGF21 (Lilly) and DFD1 using a HEK293 cell line in which human β-klotho is overexpressed. DFD1 and RGE (Amgen) had similar activities, while Fc-FGF21 (Lilly) had in vitro activity two times higher than the other proteins.

It was confirmed that DFD1 and RGE (Amgen) had similar in vitro activity, while Fc-FGF21 (Lilly) had in vitro activity two times higher than those of the other proteins, as shown in FIG. 3.

Experimental Example 2. Evaluation of Stability of Fusion Proteins

Experimental Example 2-1. Experimental Method for Evaluating Stability

In order to measure the quantity of protein aggregates at the initial stage of the sample preparation, high molecular weight aggregates (% HMW) were quantified using a size-exclusion chromatography (SEC-HPLC) method. The results are shown in FIG. 4.

Specifically, a TOSOHAAS™ model TSK-GEL® $G3000SW_{XL}$ column was used for the SEC-HPLC method. The column was equilibrated by flowing a buffer solution (1×PBS, 1 mM EDTA, pH 7.4) at a flow rate of 1 mL/min. The DFD4 and DFD13 protein stock solutions prepared in Preparation Examples 1-5 were concentrated to a target concentration of 20 mg/mL or higher at 3,000 rpm using a 30,000 MW cut-off centrifugation filter at 4° C. After the measurement of the concentration of each sample by BCA quantitative analysis, the samples were diluted with a buffer solution (IX PBS, 1 mM EDTA, pH 7.4) to a final concentration of 20 mg/mL. In order to measure the initial % HMW of DFD4 and DFD13, 20 mg/mL of the samples were diluted with the buffer solution (1×PBS, 1 mM EDTA, pH 7.4) to a final concentration of 1 mg/mL, and each sample in a volume of 100 μL was analyzed by SEC-HPLC column.

For the stability evaluation of each sample, % HMW of the samples was measured using the SEC-HPLC method on the $4^{th}$, the $8^{th}$ and the $14^{th}$ days while storing them at 5° C., 25° C. and 37° C. for two weeks.

Figure 4:
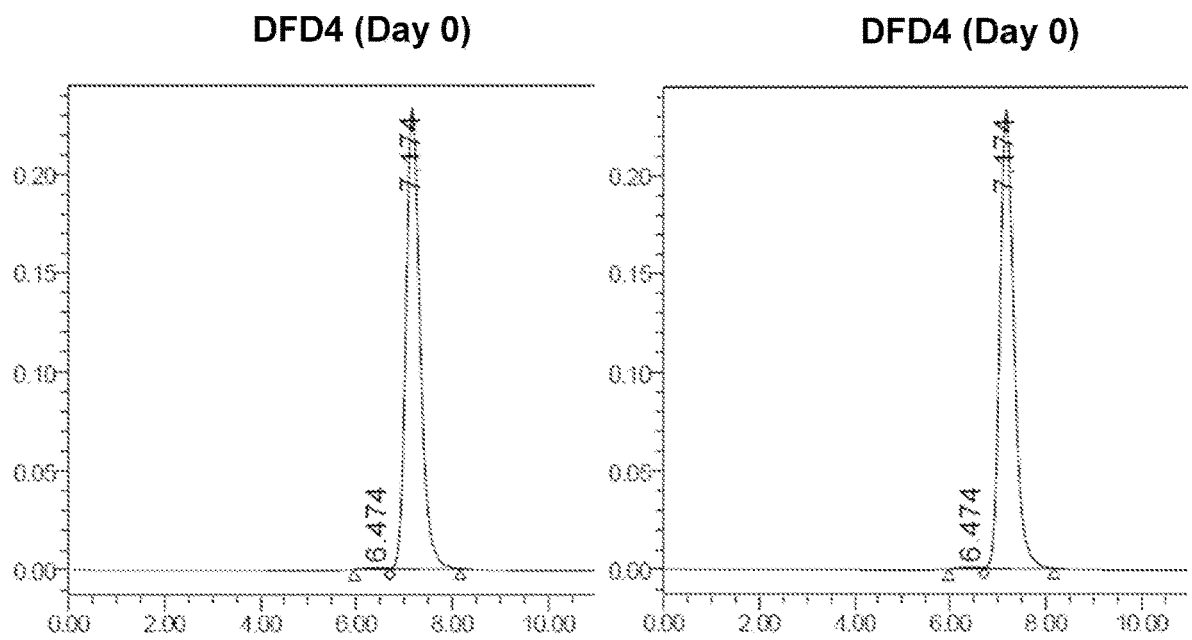
FIG. 4 shows the stability of DFD4 and that of DFD13 in order to confirm the effect of the EIRP (SEQ ID NO: 68) mutation of FGF21 on the stability of fusion protein. It was confirmed that DFD13 was associated with a lower rate of high molecular weight aggregates (HMW %) at the initial stage and at a time-point of more than 2 weeks later as compared with DFD4, indicating that the introduction of the EIRP (SEQ ID NO: 68) mutation improves the stability of the FGF21 mutant fusion protein, thereby reducing HMW % significantly.
Figure 4:
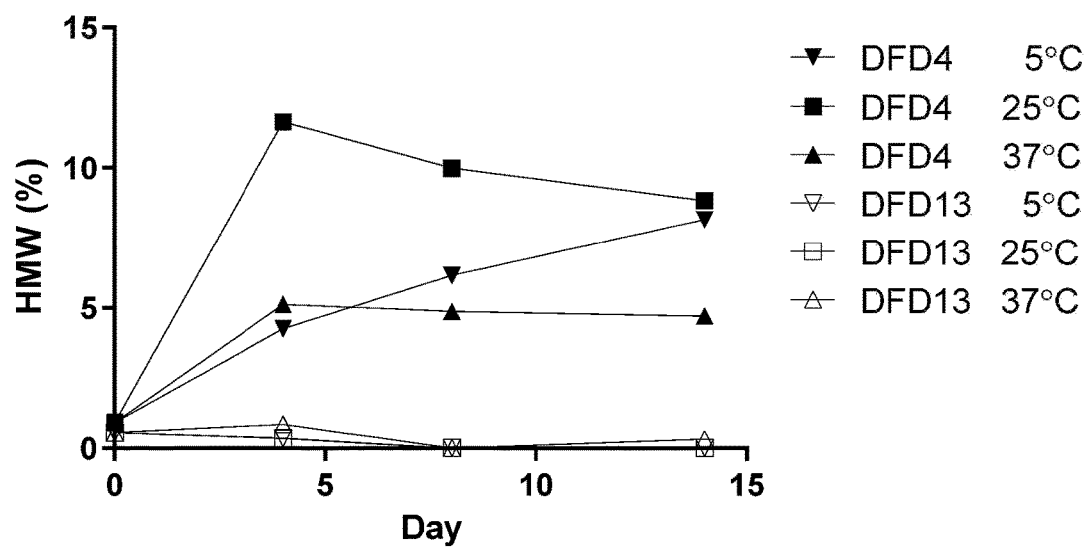

As shown in FIG. 4, it was confirmed that DFD13 had a lower quantity of high molecular weight aggregates (HMW %) at the initial stage and up to the point of 2 weeks as compared with DFD4, indicating that the introduction of the EIRP (SEQ ID NO: 68) mutation improves the stability of the FGF21 mutant fusion protein, thereby reducing HMW % significantly.

Experimental Example 2-2. Stability Results

In order to investigate the effects of the EIRP (SEQ ID NO: 68) mutation introduced into the original sequence LLLE (SEQ ID NO: 81) (amino acid residues at 98-101 of SEQ ID NO: 1) of FGF21 on stability, the stability of DFD4 (SEQ ID NO: 29) and DFD13 (SEQ ID NO: 35) was measured in accordance with the methods described in Experimental Example 2-1. The analysis results for the zero-hour sample (initial stage; Day 0) and 4-, 8-, and 14 day-stored samples of DFD4 and DFD13 are summarized in Table 4 below (in Table 4, N.D. means "not detected").

TABLE 4

Stability of DFD4 and DFD13 for 2 weeks at a concentration of 20 mg/mL (% HMW)

| | DFD4 | | | DFD13 | | |
|---|---|---|---|---|---|---|
| Day | 5° C. | 25° C. | 37° C. | 5° C. | 25° C. | 37° C. |
| 0 | | 0.91 | | | 0.56 | |
| 4 | 4.25 | 11.64 | 5.12 | 0.36 | 0.34 | 0.84 |
| 8 | 6.16 | 9.99 | 4.87 | N.D. | N.D. | N.D. |
| 14 | 8.15 | 8.83 | 4.71 | N.D. | N.D. | 0.32 |

As shown in Table 4, the quantity of % HMW at the initial stage (Day 0) was 0.91% for DFD4, and 0.56% for DFD13. After 2 weeks, the amount of % HMW increased to 8.83% for DFD4, but it was not observed in DFD13, under the condition of storage at 25° C. DFD13 was shown to have a lower % HMW rate at the initial stage and 2 weeks, as compared with DFD4, which indicates that the % HMW rate of FGF21 mutant fusion protein decreased significantly due to the introduction of the EIRP (SEQ ID NO: 68) mutation.

Experimental Example 3. Pharmacokinetic Assessment of Fusion Proteins

Experimental Example 3-1. Experimental Method for Pharmacokinetic Assessment Six-week old male ICR mice purchased from Orient BIO (Korea) were partitioned into groups (n=3/blood sampling time) in order to have similar mean values for body weight one day before drug treatment, and subcutaneously administered once with a respective sample at 1 mg/kg (2 mg/kg for RGE). Blood samples were then collected at 1, 4, 8, 12, 24, 48, 72, and 96 hours after the injection, respectively. The concentration of intact full length FGF21 protein in the blood was measured using a Intact human FGF21 ELISA Kit (F1231-K01, Eagle Biosciences, USA), which has immunoreactivity to the N-terminus and C-terminus of FGF21 protein. The concentrations of the samples in the blood collected until 96 hours after the subcutaneous injection of each fusion protein into the mice were measured, and pharmacokinetic parameters of each sample were calculated.

Experimental Example 3-2. Assessment of Pharmacokinetic Activity

Figure 5:
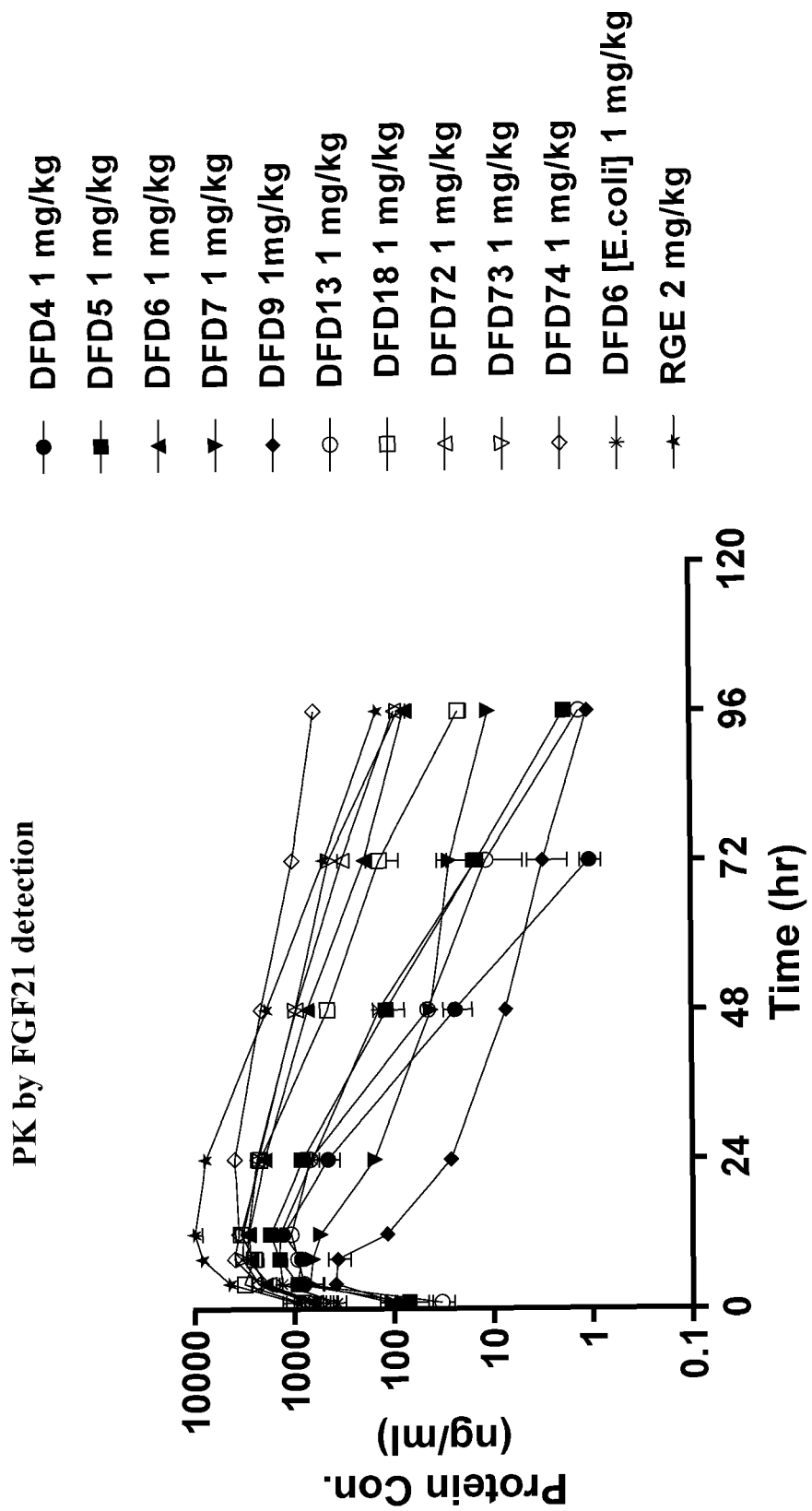
FIG. 5 shows the concentration of each protein in the blood over time for % hours after subcutaneous administration of FGF21 mutant fusion proteins. Data are indicated as mean values and standard deviation.

Based on the graph showing the concentrations of each protein in the blood versus time after the subcutaneous administration of fusion proteins in mice (FIG. 5), the pharmacokinetic parameters were calculated. The data are shown in Table 5 below.

TABLE 5

| Parameters | DFD4 | DFD5 | DFD6 | DFD7 | DFD9 | DFD13 | DFD18 | DFD72 | DFD73 | DFD74 | DFD6 (E. coli) | RGE* |
|---|---|---|---|---|---|---|---|---|---|---|---|---|
| $T_{max}$ (hour) | 12 | 12 | 12 | 4 | 4 | 12 | 12 | 8 | 8 | 8 | 8 | 12 |
| $C_{max}$ (ng/mL) | 1288 | 1732 | 2868 | 696 | 384 | 1070 | 3428 | 2962 | 3296 | 3996 | 1399 | 9921 |
| $AUC_{last}$ (ng · hr/mL) | 25856 | 40706 | 100107 | 14118 | 4656 | 28785 | 104230 | 115977 | 123511 | 206634 | 37269 | 325747 |
| Half-life (hour) | 5.5 | 8.0 | 14.9 | 19.7 | 17.4 | 7.1 | 11.0 | 14.4 | 16.6 | 26.0 | 9.1 | 12.9 |

The pharmacokinetic profile of each fusion protein was compared and evaluated based on the value of the area under the curve (AUC) indicating the degree of drug exposure.

As shown in Table 5, upon comparing DFD4 with DFD13, and DFD6 with DFD73, it was determined that the introduction of the EIRP (SEQ ID NO: 68) sequence resulted in an approximate 10 to 20% increase in AUC value. Comparing DFD9 with DFD4, the introduction of TGLEAV (SEQ ID NO: 69) resulted in an approximate 6-fold increase in AUC value.

Furthermore, the mutations of TGLEAN (SEQ ID NO: 70), G170N and G174N are designed to extend the half-life by introducing N-glycosylation into the C-terminus of FGF21, which is known to be proteolyzed in vivo. The increase in AUC due to the introduction of N-glycosylation was confirmed by comparing the mutants with each control material. In order to confirm the effect of improvement in AUC due to the introduction of N-glycosylation, the AUC value for DFD6 (E. coli) produced by E. coli which has no glycosylation was compared with that in DFD6 produced by a human cell line. DFD6 produced by the human cell line showed a 3-fold or higher increase in the AUC value as compared with DFD6 (E. coli) produced by E. coli, which demonstrated an improvement of pharmacokinetic profile due to glycosylation.

The A180E is a mutation disclosed in WO 2009/149171 owned by Amgen Inc. When the mutation of A180E was further introduced into the mutant DFD13 or DFD73 including the mutation of TGLEAV (SEQ ID NO: 69) or G170N, respectively, the resulting mutant DFD18 or DFD74, respectively, showed an approximate 2- to 3-fold additional increase in AUC value.

In summary, it was confirmed that the pharmacokinetic parameters were improved by the introduction of various mutations and combinations thereof, as compared with DFD9, the wild-type FGF21 fusion protein. The fusion protein showing the most improved AUC value was DFD74 containing the mutations of EIRP (SEQ ID NO: 68), G170N and A180E, which showed an approximate 45-fold improvement in AUC value as compared with DFD9. Furthermore, considering RGE (Amgen) at the dose of 2 mg/kg of body weight, DFD74 may have a higher degree of drug exposure as compared with RGE. The overall effects of improvement in pharmacokinetics due to the mutations are summarized in Table 6 below.

TABLE 6

| Mutation sequence | Position of mutation | Control material vs improved material | Assessment of pharmacokinetic parameters |
|---|---|---|---|
| EIRP | 98-101 | DFD4 vs DFD13 | Improvement of AUC |
| | | DFD6 vs DFD73 | |
| TGLEAV | 170-174 | DFD9 vs DFD4 | Improvement of AUC |
| TGLEA<u>N</u> | 170-174 | DFD9 vs DFD5 | Improvement of AUC |

TABLE 6-continued

| Mutation sequence | Position of mutation | Control material vs improved material | Assessment of pharmacokinetic parameters |
|---|---|---|---|
| G170<u>N</u> | 170 | DFD9 vs DFD6 | Improvement of AUC |
| | | DFD6 (E. coli) vs DFD6 | Improvement of AUC |
| G174<u>N</u> | 174 | DFD9 vs DFD7 | Improvement of AUC |
| A180E | 180 | DFD13 vs DFD18 | Improvement of AUC |
| | | DFD73 vs DFD74 | Improvement of AUC |

Experimental Example 4. Activity Evaluation of Fusion Proteins in Ob/Ob Mice

Experimental Example 4-1. Experimental Method for Evaluating Activity in Ob/Ob Mice The ob/ob mice, characterized as exhibiting hyperglycemia, insulin resistance, hyperphagia, fatty liver and obesity due to a genetic deficiency in leptin, are widely used for the study of type 2 diabetes. Male ob/ob mice (Harlan, USA) were purchased from Raonbio (Korea). These mice were 5 to 6 weeks old at the time of arrival, and 8 to 9 weeks old at the time of drug treatment after 3 weeks of adaptation. The mice were partitioned into groups (n=8/group) in order to have similar mean values for body weight and caudal blood glucose levels one day before the drug treatment (Day 0), and the samples were subcutaneously administered once according to each of their respective dosages. Dulbecco's phosphate buffered saline (DPBS, Gibco, USA) was administered as the vehicle treatment, and the glucose concentration in the blood was measured using a glucose meter, GLUCODR™ (All Medicus, Korea). The non-fasting glucose levels and body weights were measured every day until the $14^{th}$ day after administration. Glycated hemoglobin levels were also measured in each group before the administration and after the test. The glycated hemoglobin levels were calculated using a DCA™ 2000 HbA1c kit (Siemens, 5035C).

Experimental Example 4-2. Evaluation of Activity in Ob/Ob Mice

The changes in non-fasting blood glucose levels and body weights in male ob/ob mice were observed after single subcutaneous injection of 30 or 100 nmol/kg of DFD18 and DFD72, or 10, 30 or 100 nmol/kg of DFD74.

Figure 6:
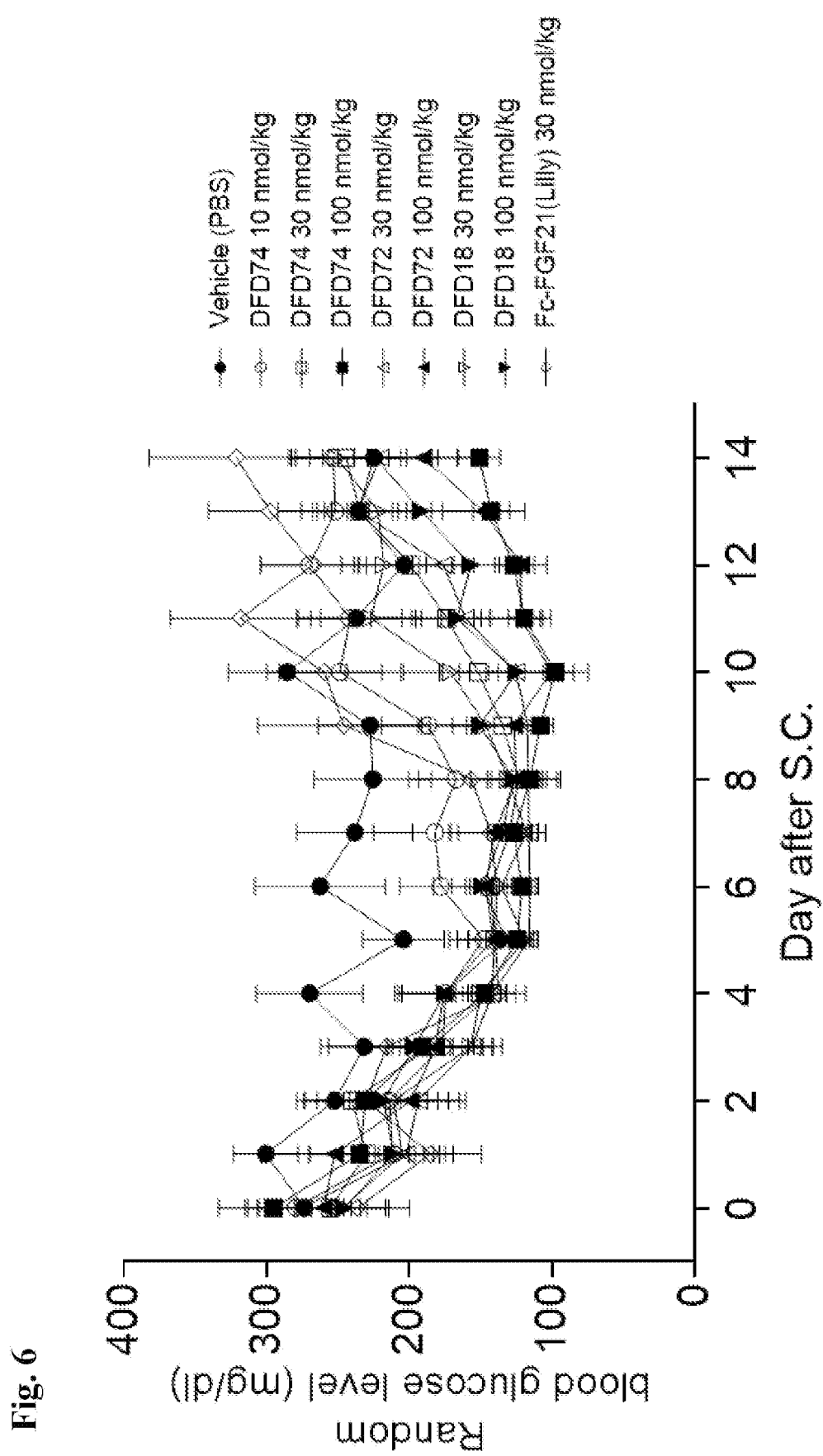
FIG. 6 shows blood glucose levels in an ob/ob mouse model after single subcutaneous injection of DFD18, DFD72, DFD74 or Fc-FGF21 (Lilly). DFD18, DFD72 and DFD74 all had an effect of lowering blood glucose level continuously. Data are indicated as mean values and standard error of the mean (S.E.M.).

It was confirmed that DFD18, DFD72 and DFD74 all had the effect of lowering blood glucose level in a dose-dependent manner. Comparing the three agents at the high dose of 100 nmol/kg, DFD72 and DFD74 showed an improved effect on lowering blood glucose level than DFD18 (FIG. 6). In addition, Fc-FGF21 (Lilly) which was used as a control material in the test, was less effective in lowering blood glucose level as compared with DFD18, DFD72 and DFD74 at the same dose level (30 nmol/kg).

Figure 7:
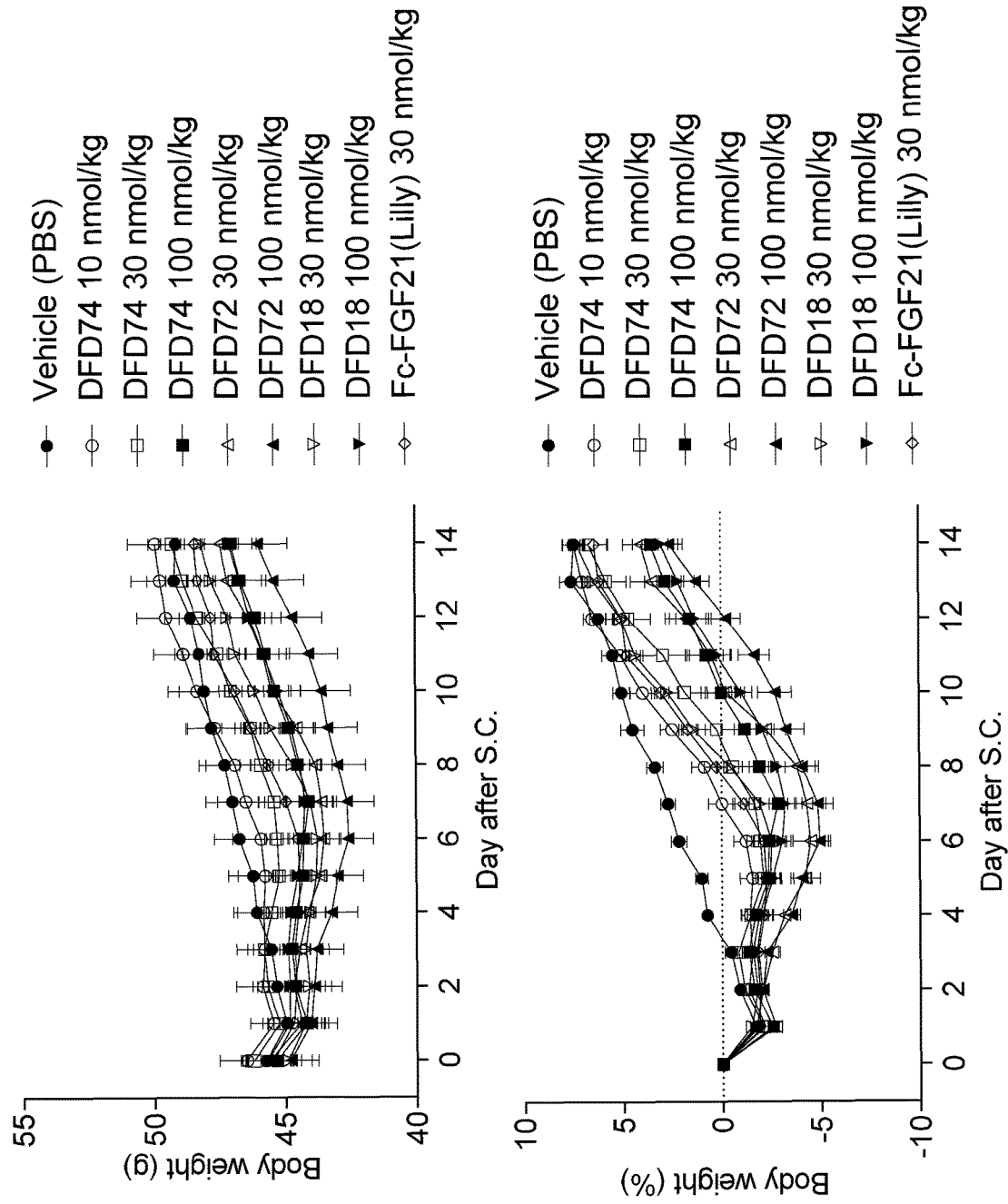
FIG. 7 shows graphs indicating the changes in body weights in the ob/ob mouse model from the day of administration to the 14$^{th}$ day after single subcutaneous injection of DFD18, DFD72, DFD74 or Fc-FGF21 (Lilly). DFD18, DFD72 and DFD74 all had an effect of reducing body weight as compared with the PBS-treated group. Data are indicated as mean values and standard error of the mean.

As for the effect on body weight reduction, comparing the three agents at the high dose of 100 nmol/kg, DFD72 was the most effective in ob/ob mice resulting in an approximate 6% reduction in body weight, and DFD18 was the next most effective, followed by DFD74 (FIG. 7).

Figure 8:
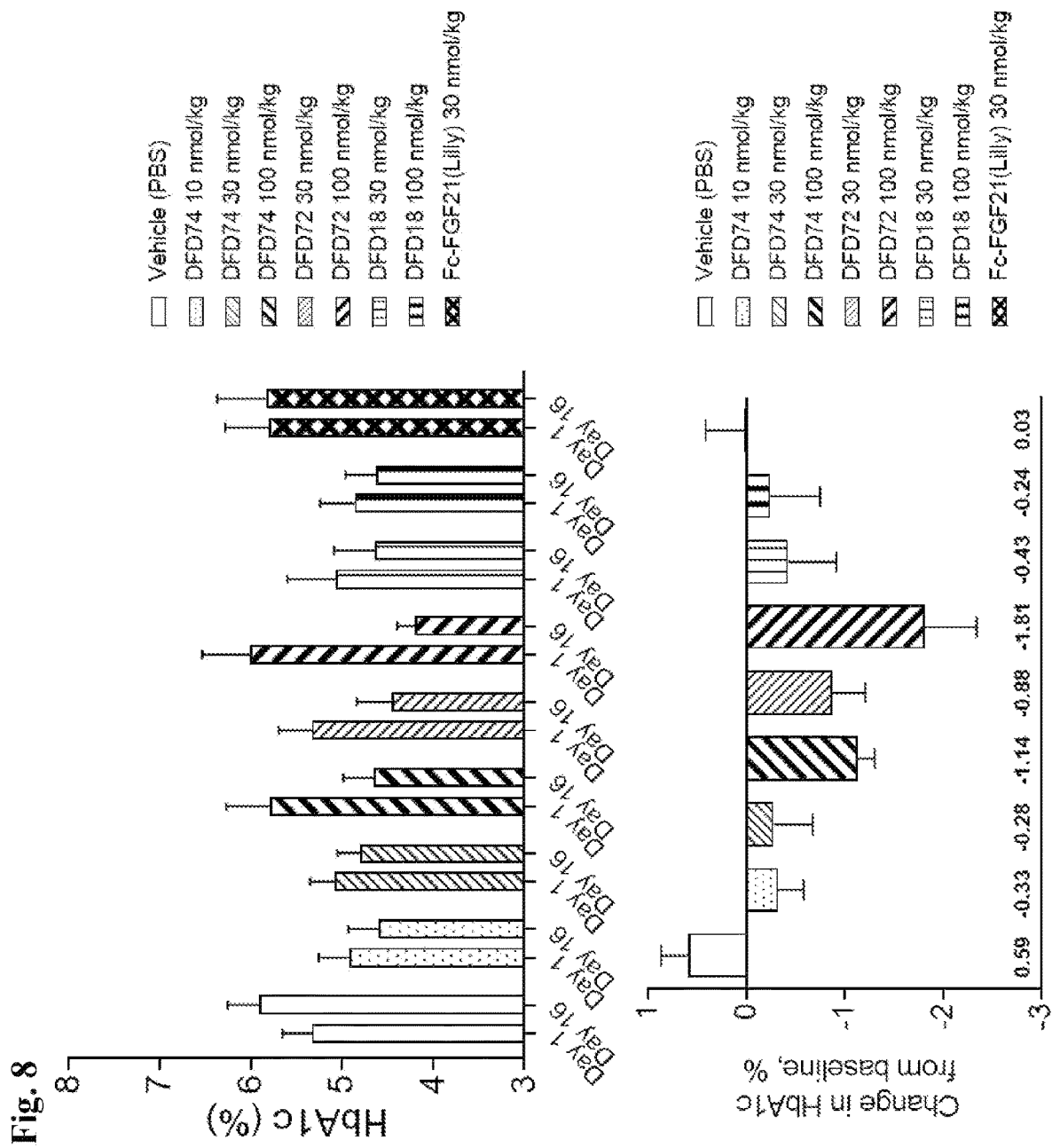
FIG. 8 shows graphs indicating the changes in glycated hemoglobin levels in the ob/ob mouse model at the day of administration (1$^{st}$ day) and the 16$^{th}$ day after single subcutaneous injection of DFD18, DFD72, DFD74 or Fc-FGF21 (Lilly). DFD18, DFD72 and DFD74 all reduced glycated hemoglobin levels at the 16$^{th}$ day as compared with those at the day of administration. Data are indicated as mean values and standard error of the mean.

After the termination of the test, the glycated hemoglobin levels indicative of the mean values of blood glucose were measured and the changes in mean blood glucose were analyzed in each test group. All of the treated groups except the control group treated with control protein Fc-FGF21 (Lilly) showed negative values in the differences between before administration and after the test, which confirmed the effectiveness of the test proteins as compared with the control material in lowering blood glucose (FIG. 8).

Experimental Example 5. Activity Evaluation of Fusion Proteins in HFD/STZ Mice

Experimental Example 5-1. Experimental Method for Evaluating Activity in HFD/STZ Mice The effects of the FGF21 mutant fusion proteins on lowering blood glucose and body weight were compared and evaluated in another diabetic model, the HFD/STZ mouse model. Conventional dietary-induced obesity mouse models (induced by feeding 60 kcal % high fat diet to C57BL/6 mice for eight weeks or longer) have weak hyperglycemic and diabetic features, although they invoke insulin resistance. The HFD/STZ mice, which may compensate for defects in the conventional dietary-induced obesity mouse models, are capable of producing dysfunctional β cells in the pancreas and decreased secretion of insulin as a result of a high fat diet (HFD) and administration of low level streptozotocin (STZ), and are therefore useful for pharmacological studies of type 2 diabetes.

Specifically, in order to induce the HFD/STZ mouse model, C57BL/6 mice (Japan SLC) were fed on a 60 kcal % high fat diet for four weeks, and then 50 mg/kg of STZ (Sigma, 85882) was administered intraperitoneally every day for 3 days to induce dysfunction in the β cells of the pancreas. After feeding on the high fat diet for an additional 2 weeks, the mice with non-fasting blood glucose levels of 200 mg/dL or higher were used for the test. The mice were partitioned into groups (n=6/group) in order to have similar mean values of body weight and caudal blood glucose levels one day before the drug treatment (Day 0), and the samples were subcutaneously administered once according to each of their respective dosages. Dulbecco's phosphate buffered saline (DPBS, Gibco, USA) was administered as the vehicle treatment, and the glucose concentration in the blood was measured using a glucose meter, GLUCODR™ (All Medicus, Korea). The non-fasting glucose levels and body weights were measured every day until the $14^{th}$ day after administration. Glycated hemoglobin levels were also measured in each group before the administration and after the test. The glycated hemoglobin levels were calculated using a DCA™ 2000 HbA1c kit (Siemens, 5035C).

Experimental Example 5-2. Activity Evaluation in HFD/STZ Mice

The changes in non-fasting blood glucose levels and body weights over time in male HFD/STZ mice were observed after single subcutaneous injection of 10 nmol/kg of DFD72 or DFD74.

Figure 9:
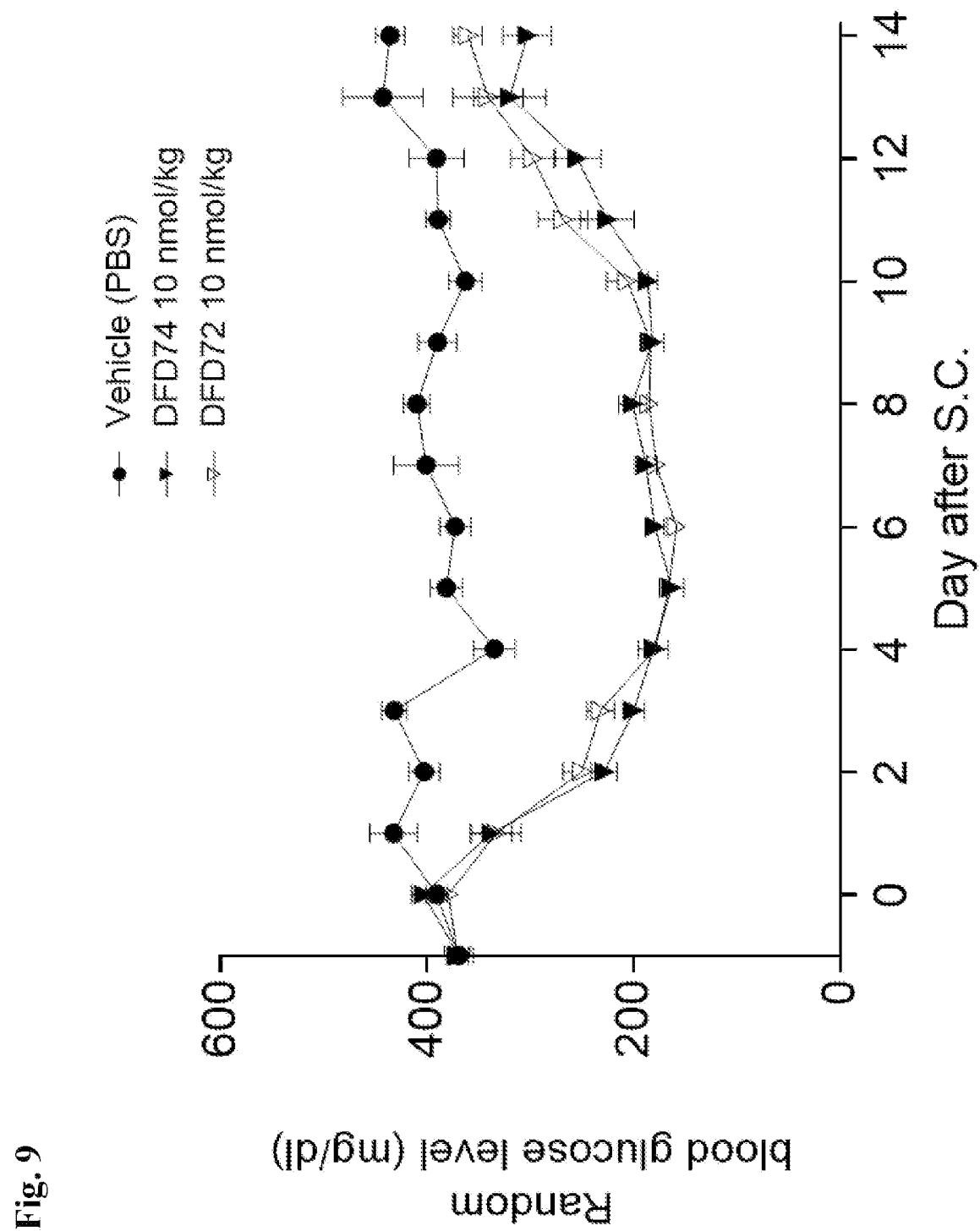
FIG. 9 shows blood glucose levels in an HFD/STZ mouse model after single subcutaneous injection of DFD72 or DFD74. Both DFD72 and DFD74 had the effect of lowering blood glucose level continuously. Data are indicated as mean values and standard error of the mean.

Regarding the changes in non-fasting blood glucose levels, it was confirmed that DFD72 and DFD74 had similar effects on lowering blood glucose levels, and the blood glucose lowering effect was maintained until the $10^{th}$ day after administration and then lost with metabolism of the drugs after the $10^{th}$ day (FIG. 9). DFD72 showed a more prolonged effect than DFD74 in terms of changes in non-fasting blood glucose levels after the $10^{th}$ day after administration.

Figure 10:
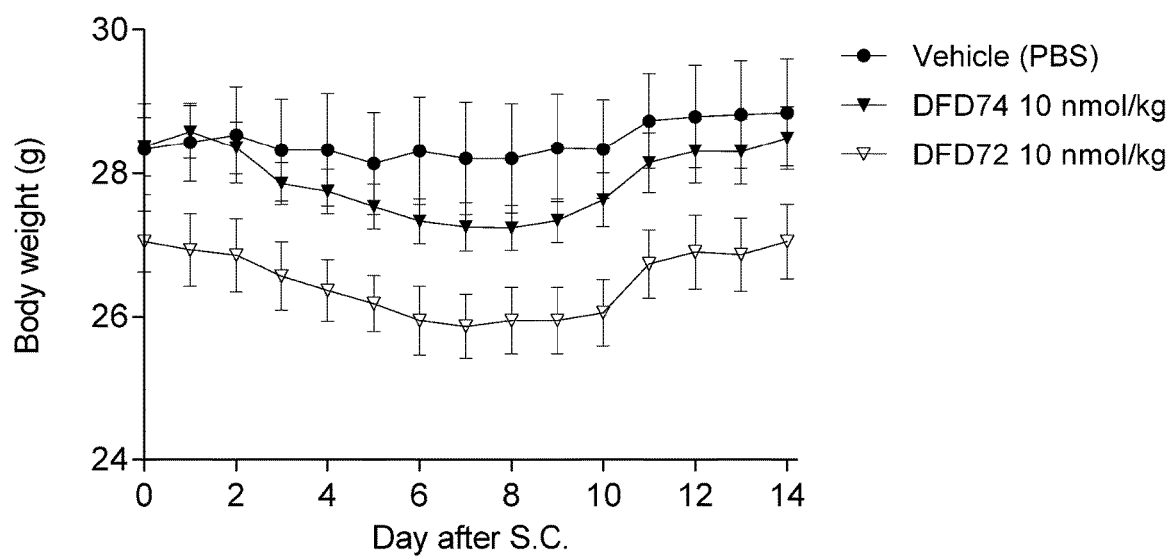
FIG. 10 shows the changes in animal body weights in the HFD/STZ mouse model from the day of administration to the 14$^{th}$ day after single subcutaneous injection of DFD72 or DFD74. Both DFD72 and DFD74 had the effect of reducing body weight as compared with the PBS-treated group. Data are indicated as mean values and standard error of the mean.
Figure 10:
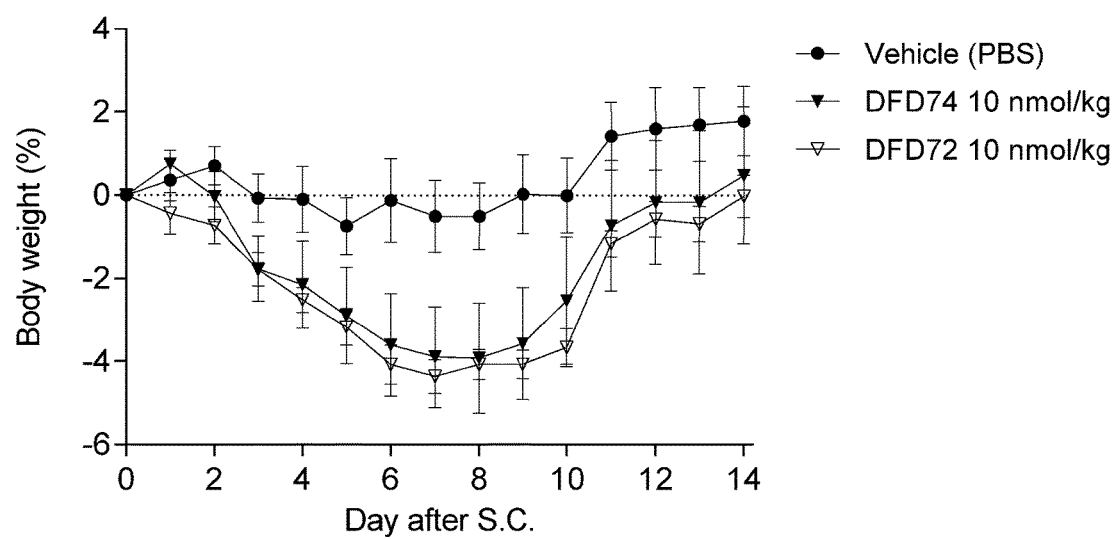

In terms of the effect on body weight reduction due to the administration of FGF21 mutant proteins, it was confirmed that both DFD72 and DFD74 had similar effects on reducing body weight by approximately 5%, and the effect disappeared after the $10^{th}$ day after administration (FIG. 10).

Figure 11:
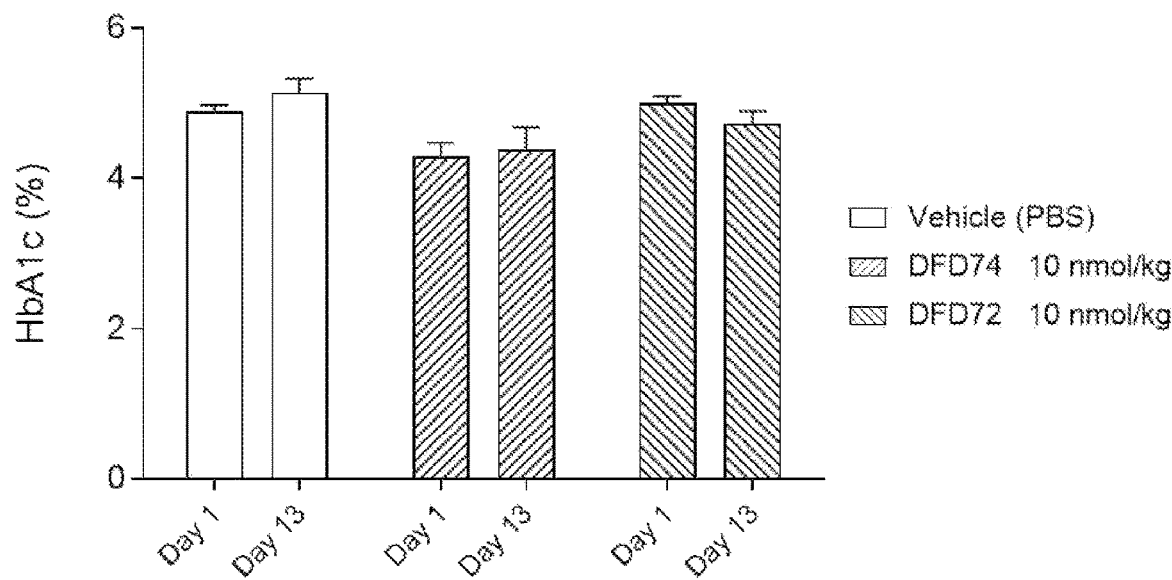
FIG. 11 shows graphs indicating the changes in glycated hemoglobin levels in the HFD/STZ mouse model at the 1$^{st}$ day and the 13$^{th}$ day after single subcutaneous injection of DFD72 or DFD74. It was observed that both DFD72 and DFD74 resulted in greater reduction of glycated hemoglobin levels as compared with the PBS-treated group. Data are indicated as mean values and standard error of the mean.
Figure 11:
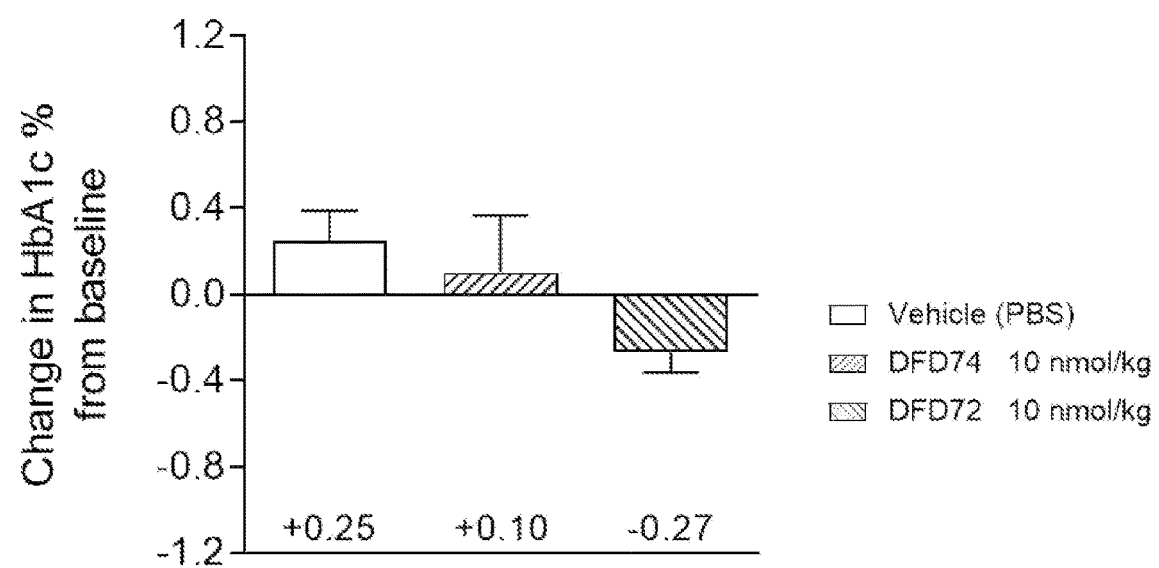

After the termination of the test, the glycated hemoglobin levels indicative of the mean value of blood glucose were measured and the changes in mean blood glucose were analyzed in each test group. While the vehicle group had an increase of 0.25 in glycated hemoglobin levels, the group treated with DFD74 had an increase of 0.1 and the group treated with DFD72 had a decrease of 0.27 (FIG. 11).

Experimental Example 6. Activity of Fusion Proteins in Diet-Induced Obese Mice

Experimental Example 6-1. Experimental Method for Evaluating Activities in Diet-Induced Obese Mice The body weight-reduction effect of DFD18, an FGF21 mutant fusion protein, was evaluated in diet-induced obese mice. For the diet-induced obesity model, C57BL/6J mice were purchased from Central Lab. Animal Inc. and fed on a high-fat diet containing 60 kcal % fat (Research diet) for 8 to 12 weeks. The mice were partitioned into groups (n=8/group) in order to have a similar mean value of body weight one day before the drug treatment (Day 0), and then 30 nmol/kg of samples were subcutaneously administered once. The changes in body weights were compared with the group treated with vehicle (PBS).

Experimental Example 6-2. Protein Activity in Diet-Induced Obese Mice

Figure 12:
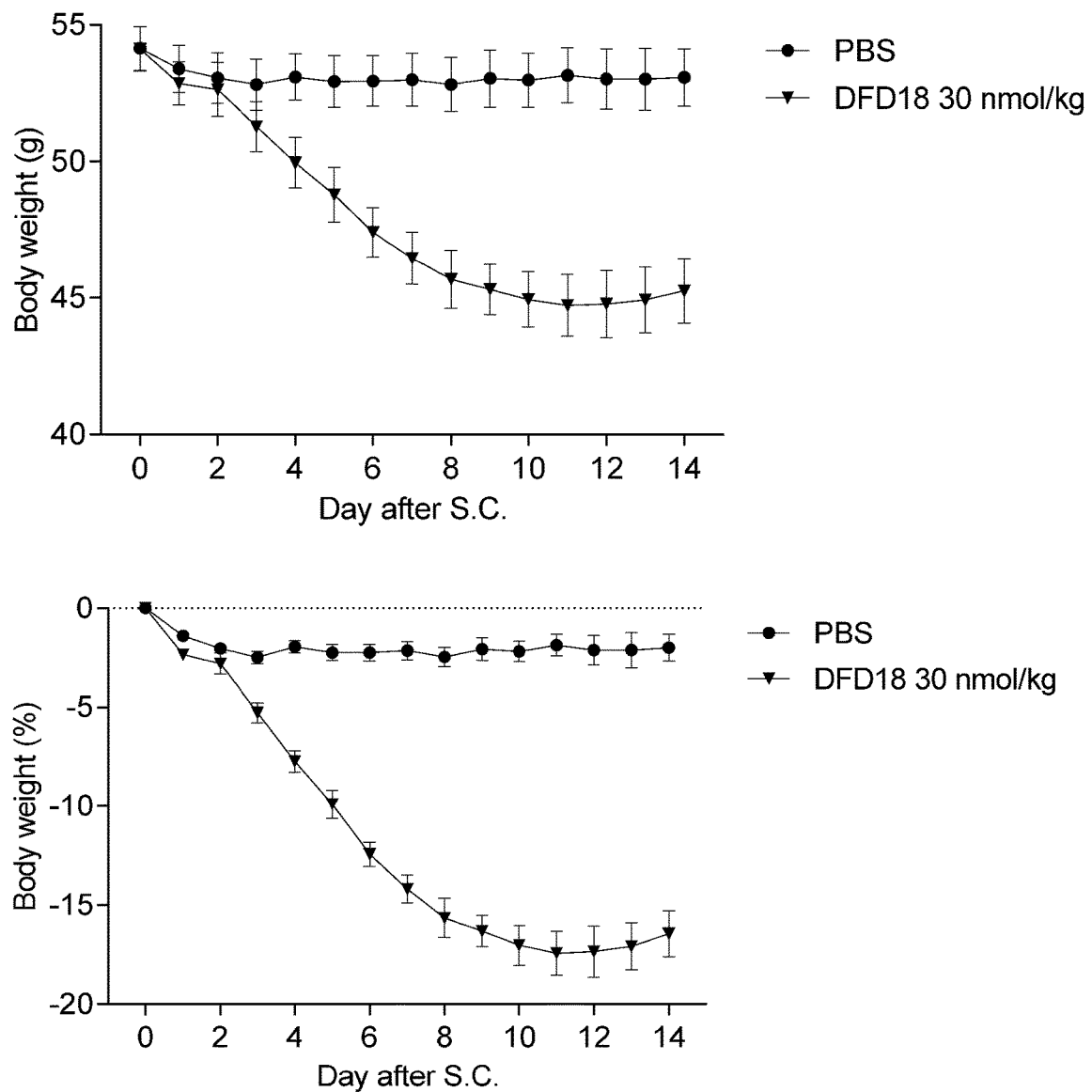
FIG. 12 shows the changes in body weights measured in the diet-induced obesity mouse model from the day of administration to the 14$^{th}$ day after single administration of DFD18. DFD18 had a significant effect on body weight reduction. Data are indicated as mean values and standard error of the mean.

For changes in body weight over time in the diet-induced obesity mouse model following single administration of 30 nmol/kg DFD18, it was confirmed that the weight-reducing effect was continuing by the 10$^{th}$ day after the administration, and the maximum weight reduction (about 18%) was at the 11$^{th}$ day after the administration, which was maintained by the 14 day (FIG. 12).

Preparation Example 2. Preparation and Purification of Dual Function Proteins

Preparation Example 2-1. Preparation of Expression Vectors for Expression of Dual Function Proteins In order to identify the effects of the sequence of the GLP-1 mutant protein and the sequence of the Fc hinge fused thereto on the in vitro activity, pharmacokinetic profiles and pharmacological efficacy, various sequences for the Fc-fused GLP-1 mutant proteins were designed. The sequences of the GLP-1 mutant proteins are listed in Table 7 below, and the sequences of Fc-fused GLP-1 mutants are listed in Table 8.

TABLE 8

| SEQ ID NO | Fc-fused GLP-1 mutant protein |
|---|---|
| 49 | DFD52: GLP1(A2G)-HyFc5 |
| 50 | DFD53: GLP1(A2G)-HyFc40 |
| 51 | DFD54: GLP1(GE)-HyFc5 |
| 52 | DFD55: GLP1(GE)-HyFc40 |
| 53 | DFD56: GLP1(GG)-HyFc5 |
| 54 | DFD57: GLP1(GG)-HyFc40 |
| 55 | DFD58: GLP1(GEG)-HyFc5 |
| 56 | DFD59: GLP1(GEG)-HyFc40 |

In Table 8, HyFc5 refers to SEQ ID NO: 47, and HyFc40 refers to SEQ ID NO: 48.

In order to investigate the effects of the sequences of the GLP-1 mutant proteins and FGF21 mutant proteins, the sequence of the Fc hinge fused to the GLP-1 mutants, the sequence of the linker connected between the FGF21 mutant proteins and Fc on the in vitro activity, pharmacokinetic profiles and pharmacological efficacy, various sequences for the dual function proteins were designed. The sequences of the dual function proteins including the GLP-1 mutant proteins and FGF21 mutant proteins are listed in Table 9 below. Each dual function protein contains a GLP-1 mutant protein, an Fc region of an immunoglobulin, a linker and an FGF21 mutant protein connected in this order from the N-terminus to C-terminus.

TABLE 9

| SEQ ID NO | Material code | Sequence of GLP-1 mutant protein | Fusion carrier | Linker sequence | Changes in FGF21 sequence |
|---|---|---|---|---|---|
| 58 | DFD23 | GLP-1(A2G) | hyFc40 (SEQ ID NO: 48) | GS3 (SEQ ID NO: 4) | FGF21 (EIRP, TGLEAV) |
| 59 | DFD24 | GLP-1(GE) | hyFc5 (SEQ ID NO: 47) | GS3 (SEQ ID NO: 4) | FGF21 (EIRP, TGLEAV) |
| 60 | DFD25 | GLP-1(GE) | hyFc40 (SEQ ID NO: 48) | GS3 (SEQ ID NO: 4) | FGF21 (EIRP, TGLEAV) |
| 61 | DFD26 | GLP-1(GG) | hyFc5 (SEQ ID NO: 47) | GS3 (SEQ ID NO: 4) | FGF21 (EIRP, TGLEAV) |
| 62 | DFD27 | GLP-1(GG) | hyFc40 (SEQ ID NO: 48) | GS3 (SEQ ID NO: 4) | FGF21 (EIRP, TGLEAV) |
| 63 | DFD28 | GLP-1(GEG) | hyFc5 (SEQ ID NO: 47) | GS3 (SEQ ID NO: 4) | FGF21 (EIRP, TGLEAV) |
| 64 | DFD29 | GLP-1(GEG) | hyFc40 (SEQ ID NO: 48) | GS3 (SEQ ID NO: 4) | FGF21 (EIRP, TGLEAV) |
| 65 | DFD69 | GLP-1(GEG) | hyFc40 (SEQ ID NO: 48) | GS3 (SEQ ID NO: 4) | FGF21(EIRP, TGLEAV, A180E) |
| 66 | DFD112 | GLP-1(GEG) | hyFc40 (SEQ ID NO: 48) | GS3 (SEQ ID NO: 4) | FGF21(EIRP, TGLEAN, A180E) |
| 67 | DFD114 | GLP-1(GEG) | hyFc40 (SEQ ID NO: 48) | GS3 (SEQ ID NO: 4) | FGF21(EIRP, G170N, A180E) |

TABLE 7

| SEQ ID NO | Sequence of GLP-1 mutant protein |
|---|---|
| 43 | GLP-1(A2G) |
| 44 | GLP-1(GE) |
| 45 | GLP-1(GG) |
| 46 | GLP-1(GEG) |

Specifically, the nucleotide sequences encoding each of the dual function proteins were synthesized after consulting with Bioneer Corporation (Korea) based on the amino acid sequence of each protein. NheI and NotI restriction enzyme sequences were added to the 5' terminus and 3' terminus of the nucleotide sequences encoding each of the dual function proteins and an initiation codon for protein translation and a leader sequence (MDAMLRGLCCVLLLCGAVFVSPSHA) (SEQ ID NO: 83) enabling secretion of the expressed protein to the outside of a cell were inserted next to the restriction enzyme sequence at the 5' terminus. A termination codon was inserted next to the nucleotide sequence, which encodes each of the dual function proteins. The nucleotide sequence encoding each of the dual function proteins was cloned into a pTrans-empty expression vector by using the two restriction enzymes NheI and NotI. The pTrans-empty expression vector, which has a simple structure including a CMV promoter, a pUC-derived replication origin, an SV40-derived replication origin and an ampicillin-resistance gene, was purchased from CEVEC Pharmaceuticals (Germany).

Preparation Example 2-2. Construction of Plasmid DNA for Expression of Fc-Fused GLP-1 Mutant and Dual Function Proteins

*E. coli* was transformed with each of the expression vectors constructed in Preparation Example 2-1 to obtain a large quantity of plasmid DNA to be used for expression. *E. coli* cells, with cell walls weakened through heat shock, were transformed with each expression vector, and the transformants were plated out on an LB plate to obtain colonies. The colonies thus obtained were inoculated into LB media, cultured at 37° C. for 16 hours, and each *E. coli* culture containing each expression vector was obtained in a volume of 100 mL. The *E. coli* thereafter obtained was centrifuged to remove the culture medium, and then P1, P2, P3 solutions (QIAGEN, Cat No.: 12963) were added to break the cell walls, thereby obtaining a DNA suspension in which proteins and DNA were separated. Plasmid DNA was purified from the DNA suspension thus obtained by using a QIAGEN™ DNA purification column. The eluted plasmid DNA was identified by agarose gel electrophoresis, and the concentrations and purities were measured using a NANO-DROP™ device (Thermo Scientific, NANODROP™ Lite). The DNA thus obtained was used for expression.

Preparation Example 2-3. Expression of Fc-Fused GLP-1 Mutants and Dual Function Proteins in CAP-T Cells Human cell lines were transformed with each plasmid DNA obtained in Preparation Example 2-2. Each plasmid DNA type was transduced into CAP-T cells (CEVEC), which had been cultured in PEM medium (Life Technologies), by using a PEI solution (Polyplus, Cat. No.: 101-10N). The mixed solution of DNA and the PEI solution was mixed with the cell suspension using FREESTYLE™ 293 expression medium (Invitrogen), cultured at 37° C. for 5 hours, and PEM medium was added. After culturing at 37° C. for 5-7 days, the culture was centrifuged to remove cells and supernatant containing each protein was obtained.

Preparation Example 2-4. Purification of Fc-Fused GLP-1 Mutants and Dual Function Proteins Protein A affinity chromatography column (GE Healthcare) was equilibrated with 1×PBS buffer solution (pH 7.4). The culture supernatant including each of the Fc-fused GLP-1 mutants and dual function proteins obtained in Preparation Example 2-3 was filtered with a 0.2 μm filter, and then loaded into a Protein A affinity chromatography column. The column was washed with 1×PBS buffer solution (pH 7.4) and then the proteins were eluted using 100 mM glycine buffer solution (pH 3.0). The proteins obtained by affinity chromatography were purified using an anion exchange resin column (POROS® HQ 50 μm, Thermo Fisher Scientific). The anion exchange resin column was equilibrated with 50 mM Tris buffer solution (pH 8.0), before the proteins eluted from the affinity chromatography were loaded thereto.

After washing the column with 50 mM Tris buffer solution (pH 8.0), 50 mM Tris buffer solution (pH 8.0) was dispensed along the concentration gradient and the eluted fractions were analyzed. Each eluted fraction was analyzed by using size exclusion chromatography (SEC-HPLC), and the fractions including the Fc-fused GLP-1 mutants and dual function proteins with high purity were collected and dialyzed overnight at 4° C. using a final buffer solution (1×PBS, 1 mM EDTA, pH 7.4). Upon completion of the dialysis, the obtained protein stock solution was concentrated at 3,000 rpm using a 30,000 MW cut-off centrifugation filter at 4° C. The concentration of each protein was measured via BCA quantitative analysis.

Experimental Example 7. In Vitro Activity of Dual Function Proteins

Experimental Example 7-1. Activity of DFD23, DFD24, DFD25, DFD26, DFD27, DFD28 and DFD29

The in vitro GLP-1 activities of the dual function proteins DFD23, DFD24, DFD25, DFD26, DFD27, DFD28 and DFD29 were measured. Specifically, a CHO cell line (Eurofins, HTS163C2), overexpressing the human GLP-1 receptor was purchased and used to evaluate the GLP-1 activities of the dual function proteins. For the evaluation of activity, samples containing the fusion proteins (protein stock solutions prepared in Preparation Example 2-4; hereinafter, "sample") were subjected to a 4-fold serial dilution at a concentration of 25 nM. After the human GLP-1 receptor-overexpressing CHO cell line was treated for 30 minutes, the intracellular cAMP produced was measured (Cisbio, 62AM4PEB). The activity of each protein was evaluated by comparing the $EC_{50}$ values.

Figure 13:
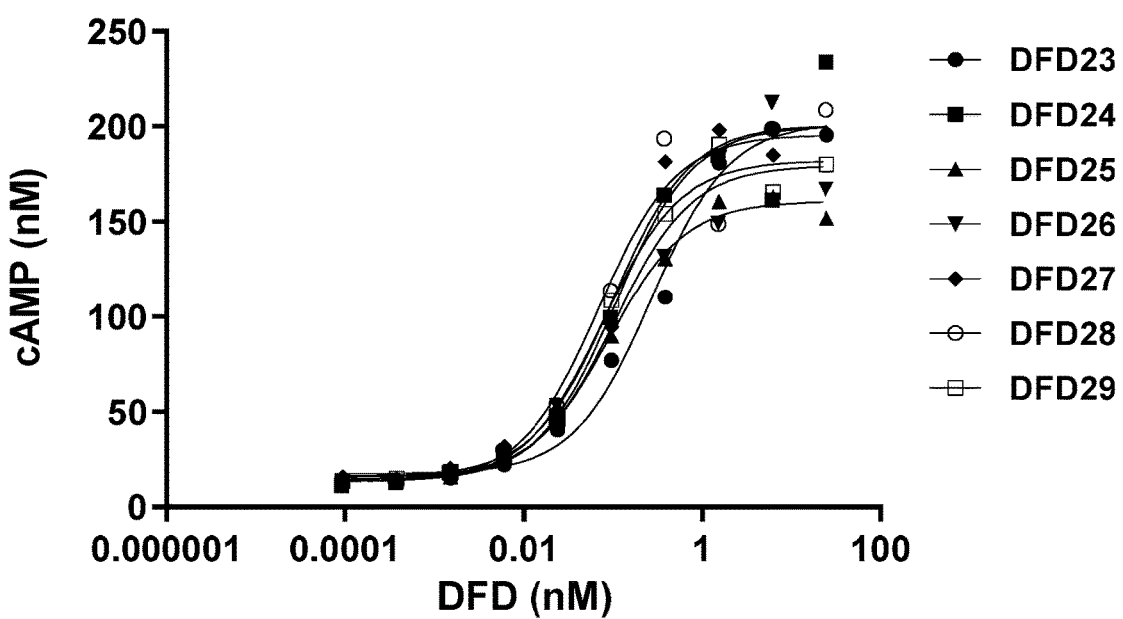
FIG. 13 is a graph showing the in vitro GLP-1 activities of dual function proteins depending on the hinges which link the C-terminus of GLP-1 mutants and GLP-1 to the Fc region using a CHO cell line in which human GLP-1 receptor is overexpressed. Generally, the dual function protein including a GLP-1 (A2G) sequence (DFD23) exhibited 2 to 3 times lower activity than those of other dual function proteins including other GLP-1 mutant sequences. No significant difference in GLP-1 activities was shown between the dual function proteins including mutant sequences except the GLP-1 (A2G) sequence.

As shown in FIG. 13, the dual function protein containing the GLP-1 (A2G) sequence showed activity approximately 2-3 times lower than that for the dual function proteins containing other GLP-1 mutant sequences. No significant difference in GLP-1 activities was observed between the dual function proteins containing the mutation sequences except the GLP-1 (A2G) sequence.

Experimental Example 7-2. Activities of DFD59, DFD69, DFD112 and DFD114

The in vitro GLP-1 activities of the dual function proteins DFD69, DFD112 and DFD114 prepared in Preparation Example 2 and DFD59 (an Fc-fused GLP-1 mutant) were measured. Specifically, a CHO cell line (Eurofins, HTS163C2) overexpressing the human GLP-1 receptor was purchased and used to evaluate the GLP-1 activities of the dual function proteins. For the evaluation of activity, the sample containing each of the fusion proteins was subjected to a 4-fold serial dilution at a concentration of 25 nM. After the human GLP-1 receptor-overexpressing CHO cell line was treated for 30 minutes, the intracellular cAMP produced was measured (Cisbio, 62AM4PEB).

Figure 14:
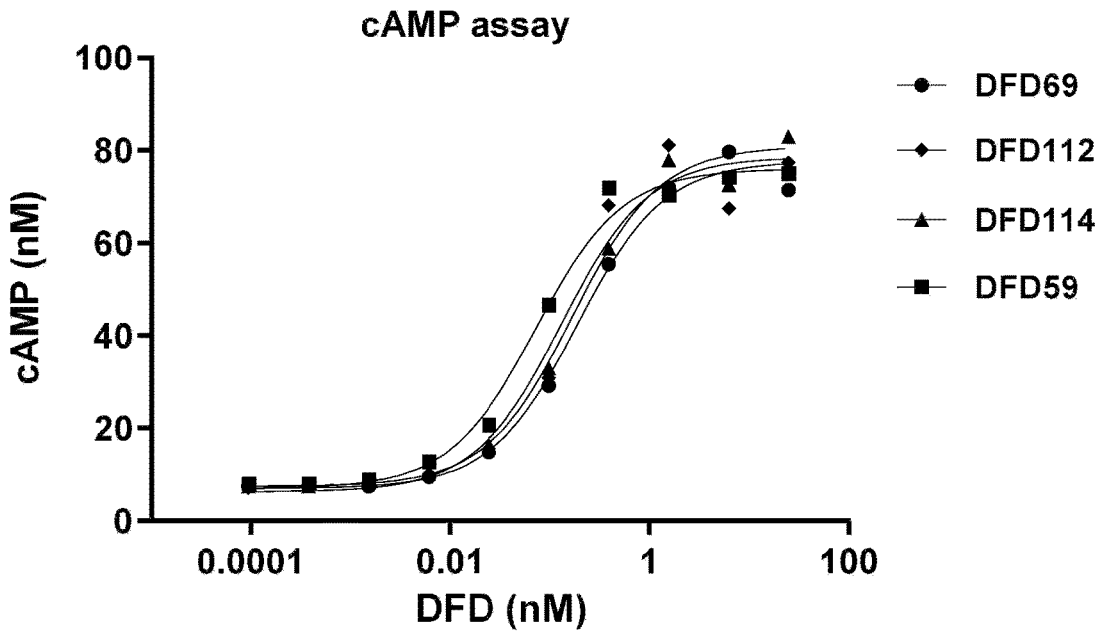
FIG. 14 shows graphs indicating the GLP-1 activities of DFD59, DFD69, DFD112 and DFD114 and the FGF21 activities of DFD69, DFD112 and DFD114. In vitro GLP-1 activities of three dual function proteins (DFD69, DFD112 and DFD114) and Fc-fused GLP-1 mutant including no FGF21 (DFD59) were measured using a CHO cell line in which human GLP-1 receptor is overexpressed. The three dual function proteins showed similar $EC_{50}$ values, and the Fc-fused GLP-1 mutant (DFD59) showed about 2 times higher activity than those of dual function proteins. In vitro activities of dual function proteins depending on FGF21 mutants were measured using a HEK293 cell line in which human β-klotho is overexpressed. It was confirmed that the in vitro activities of the FGF21 portion were similar in the three dual function proteins.
Figure 14:
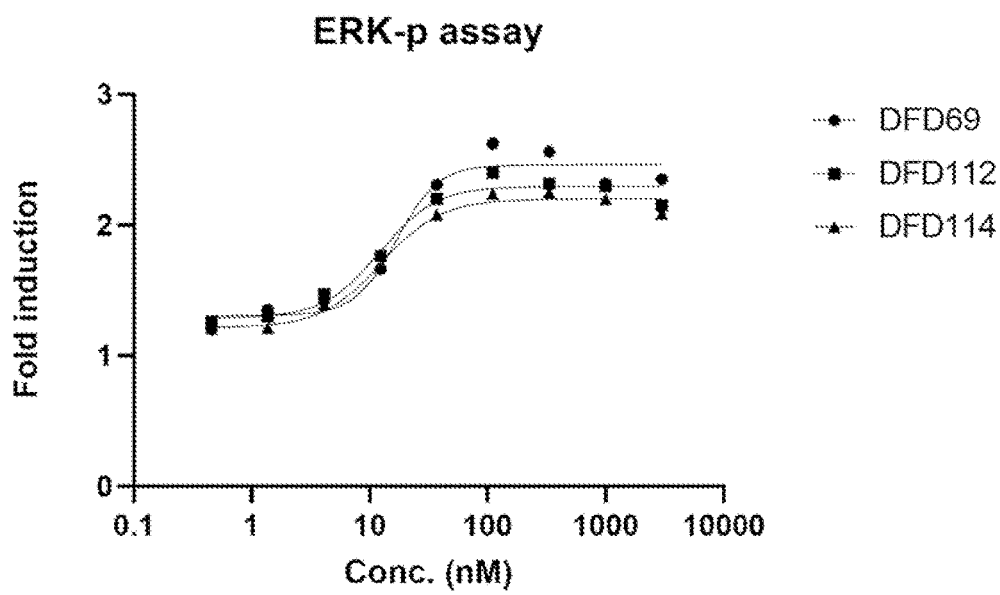

As shown in FIG. 14, the activity of each protein was evaluated by comparing the $EC_{50}$ value. The three dual function proteins showed similar $EC_{50}$ values, and DFD59 (containing no FGF21 mutant) showed activity approximately 2 times higher than that of the dual function proteins.

Next, the in vitro activities of the FGF21 portion in DFD69, DFD112 and DFD114 were measured. Specifically, the in vitro activities of the FGF21 portion in the dual function proteins were evaluated using a HEK293 cell line overexpressing human β-klotho (a co-receptor of FGF21). For the evaluation of activity, samples containing each of the dual function proteins were subjected to a 3-fold serial dilution at a concentration of 3 μM. After having been cultured in a serum-deficient state for 5 hours, the human β-klotho-overexpressing HEK293 cell line was treated for 20 minutes, before the cells were lysed by adding cytolysis buffer (Cisbio/Cat #64ERKPEG) with stirring at 60 rpm for 30 minutes at room temperature. The cell lysate solution was mixed with antibodies which can detect ERK and phosphorylated ERK, and the mixture was maintained at room temperature for 2 hours. Fluorescence was detected using a fluorometric detector (TECAN/GENiosPro). The activities were measured by comparing their $EC_{50}$ values.

It was confirmed that the in vitro activities of the FGF21 portion of the dual function proteins DFD69, DFD112 and DFD114 were similar, as shown in FIG. 14.

Experimental Example 8. Pharmacokinetic Assessment of Dual Function Proteins

Experimental Example 8-1. Experimental Method for Pharmacokinetic Assessment Six-week old male ICR mice purchased from Orient BIO (Korea) were partitioned into groups (n=3/blood sampling time) in order to have a similar mean value of body weight one day before drug treatment, and subcutaneously administered once with a respective sample in a volume of 1 mg/kg. The blood samples were collected at 1, 4, 8, 12, 24, 48, 72, 96, 144, 192 and 240 hours after the injection, respectively. The concentration of each dual function protein in the blood was measured based on the FGF21 portion and the GLP-1-Fc portion separately. The concentration of the intact full length FGF21 portion of the dual function protein in the blood was measured using an Intact human FGF21 ELISA Kit (F1231-K01, Eagle Biosciences, USA), which has immunoreactivity to the N-terminus and C-terminus of FGF21 protein. Further, the concentration of the active GLP-1-Fc portion of the dual function protein in the blood was measured using an antibody, which has immunoreactivity to the N-terminus of GLP-1 and Fc, as determined through ELISA analysis. The concentrations of the FGF21 and GLP-1-Fc portions of each protein in the blood samples collected until 240 hours after single subcutaneous injection of each protein into the mice were measured, and the pharmacokinetic parameters of each protein was calculated.

Experimental Example 8-2. Pharmacokinetic Activity Results

Figure 15:
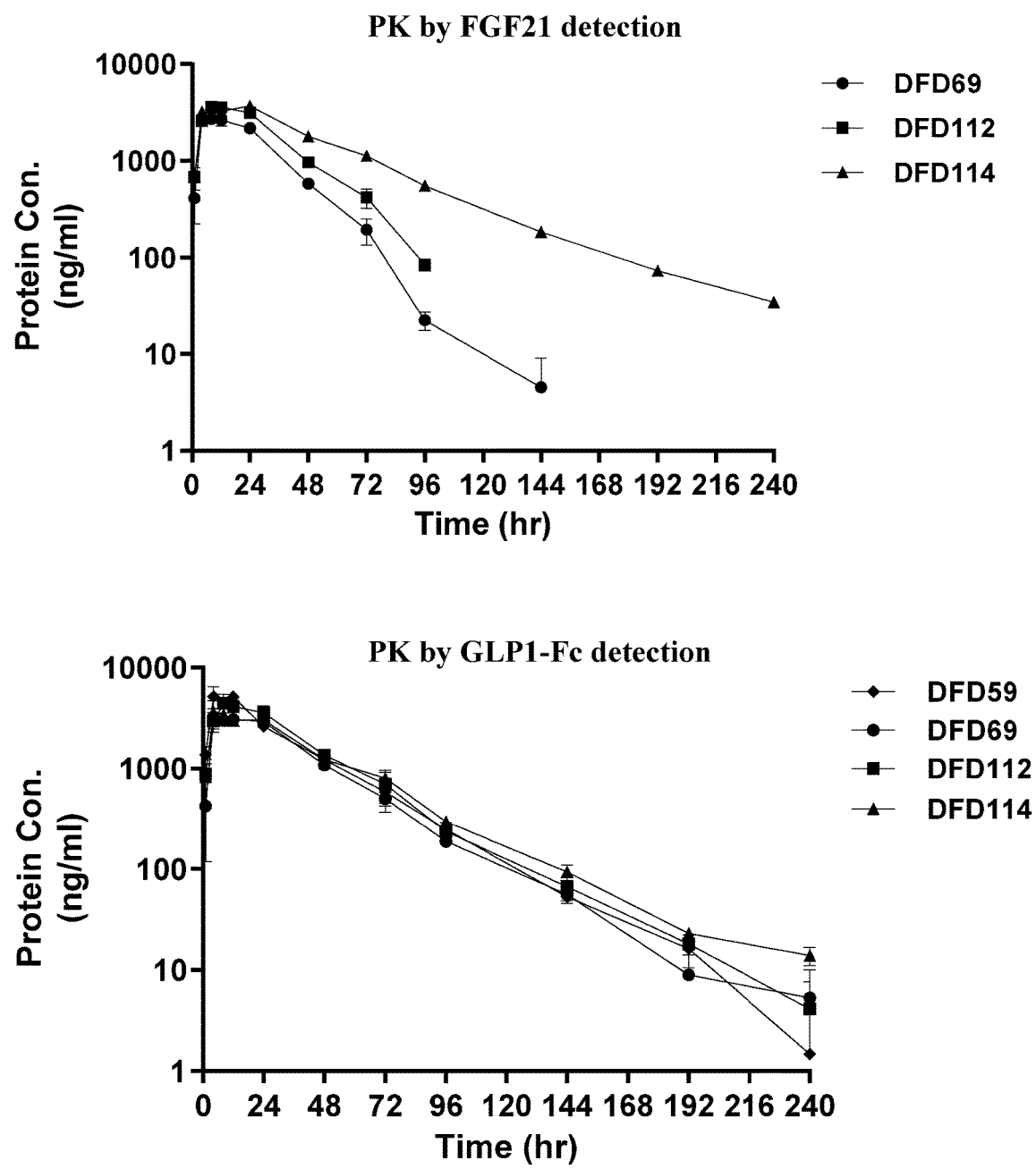
FIG. 15 shows the concentrations of proteins in the blood versus time for 240 hours after subcutaneous administration of dual function proteins. Data are indicated as mean values and standard deviation.

Based on the concentration of each active substance in the blood over time after single subcutaneous administration of each protein in mice (FIG. 15), pharmacokinetic parameters for the FGF21 and GLP-1-Fc portions of the dual function proteins were calculated. The data are shown in Table 10 below.

TABLE 10

| Parameter | FGF21 detection | | | GLP-1-Fc detection | | | |
|---|---|---|---|---|---|---|---|
| | DFD69 | DFD112 | DFD114 | DFD59 | DFD69 | DFD112 | DFD114 |
| $T_{max}$ (hour) | 8 | 8 | 24 | 4 | 4 | 8 | 4 |
| $C_{max}$ (ng/mL) | 2715 | 3619 | 3711 | 5202.1 | 3234 | 4454 | 3616 |
| $AUC_{last}$ (ng · hr/mL) | 100907 | 144395 | 222504 | 182852 | 149083 | 189338 | 171687 |
| Half-life (hour) | 13.4 | 14.2 | 39.9 | 20.7 | 23.3 | 24.7 | 27.2 |

The pharmacokinetic profiles of each dual function protein were compared and evaluated based on the value of the area under the curve (AUC), indicating the degree of drug exposure.

As shown in Table 10, for the pharmacokinetic parameters of the FGF21 portion, DFD114 showed the highest degree of drug exposure (AUC) and half-life, and DFD112 showed the next highest AUC value, followed by DFD69. DFD114 exhibited an approximate 2-fold or higher increase in AUC value as compared with DFD69. For the pharmacokinetics of the GLP-1-Fc portion, the four proteins (DFD59, DFD69, DFD112 and DFD114) containing the same GLP-1 mutant sequence showed similar AUC values.

Experimental Example 9. Activity Evaluation in Db/Db Mice

Experimental Example 9-1. Method for Evaluating Activities in Db/Db Mice

The db/db mice, characterized as having hyperglycemia, insulin resistance, hyperphagia, fatty liver and obesity due to a genetic deficiency for the leptin receptor and exhibiting more serious hyperglycemia and obesity than ob/ob mice, are widely used for the study of type 2 diabetes. Male db/db mice (Harlan, USA) were purchased from Raonbio (Korea). These mice were 5 to 6 weeks old at the time of arrival, and 8 to 9 weeks old at the time of drug treatment, after 3 weeks of adaptation. The mice were partitioned into groups (n=6/group) in order to have a similar mean value of body weight and caudal blood glucose levels one day before the drug treatment (Day 0), and the samples were subcutaneously administered once according to each of their respective dosages. Dulbecco's phosphate buffered saline (DPBS, Gibco, USA) was administered as the vehicle treatment, and the glucose concentration in the blood was measured using a glucose meter, GLUCODR™ (All Medicus, Korea). The non-fasting glucose levels and body weights were measured every day until the $14^{th}$ day after administration. Glycated hemoglobin levels were also measured in each group before the administration and after the test. The glycated hemoglobin levels were calculated using a DCA™ 2000 HbA1c kit (Siemens, 5035C).

Experimental Example 9-2. Evaluation of Activity in Db/Db Mice

The changes in non-fasting blood glucose levels and body weights in male db/db mice were observed after single subcutaneous injection of 10 or 30 nmol/kg of dual function protein DFD114, single subcutaneous injection of 30 nmol/kg of long-acting GLP-1-Fc single function protein DFD59, and combined administration of 30 nmol/kg of DFD59 and DFD74 (which are GLP-1-Fc and Fc-FGF21 single function proteins, respectively) to compare the effect of the dual function protein DFD114 with combined administration of Fc-FGF21 and GLP-1-Fc single function proteins.

Figure 16:
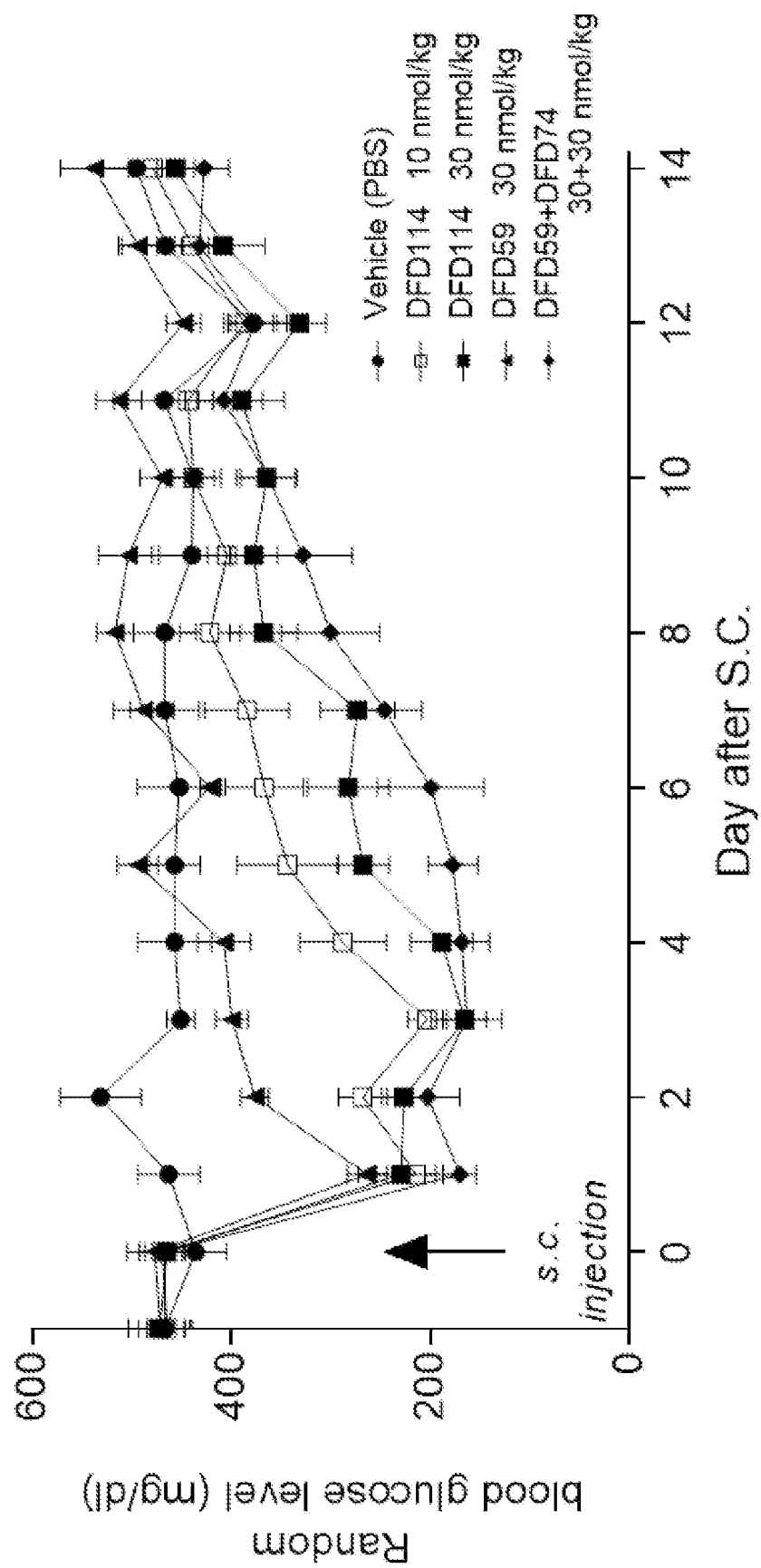
FIG. 16 shows the blood glucose levels in a db/db mouse model after single subcutaneous injection of DFD114 or DFD59 and single subcutaneous injection of combination of DFD59 and DFD74. The groups treated with dual function proteins showed stronger effects on lowering blood glucose levels than those treated with single function proteins. Data are indicated as mean values and standard error of the mean (S.E.M.).

The long-acting GLP-1-Fc protein DFD59 caused a sharp reduction in blood glucose levels by the $1^{st}$ day after administration, but the reduction in blood glucose decreased after the $2^{nd}$ day and the blood glucose level was similar to that of the vehicle-treated group after the $4^{th}$ day. Meanwhile, the group treated with DFD114 showed excellent effects on blood glucose reduction by the $3^{rd}$ day after administration, and the effects on lowering blood glucose level disappeared more rapidly after the $4^{th}$ day from the administration at the dose of 10 nmol/kg than for 30 nmol/kg, indicating dose-dependent differences in the duration of the blood glucose lowering effect. The groups treated with combined administration of each protein showed the most sustained effects for lowering blood glucose levels as compared with those of the other groups, indicating that the combination of GLP-1 and FGF21 had an excellent effect on controlling blood glucose level (FIG. 16).

Figure 17:
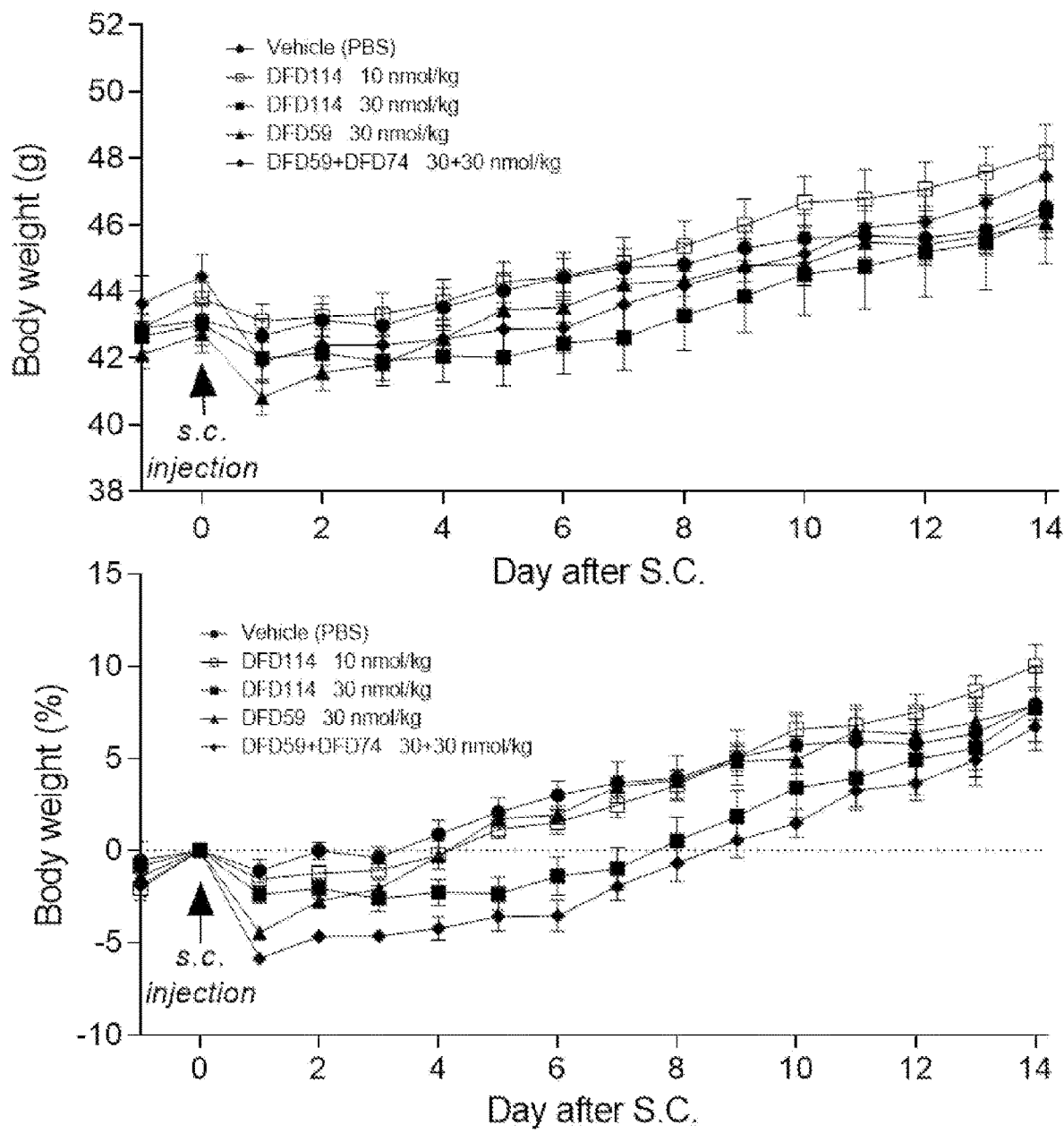
FIG. 17 shows graphs indicating the changes in body weights in db/db mouse model from the day of administration to the 14$^{th}$ day after single subcutaneous injection of DFD114 or DFD59 and single subcutaneous injection of combination of DFD59 and DFD74. The groups treated with dual function proteins showed stronger effects on reducing body weight than those treated with single function proteins. Data are indicated as mean values and standard error of the mean (S.E.M.).

As for the effect on body weight reduction, the groups treated with a combination of DFD59 and DFD74 showed the greatest effects on reducing body weight, and the group treated with 30 nmol/kg of DFD114 also showed an outstanding effect on reducing body weight (FIG. 17).

Figure 18:
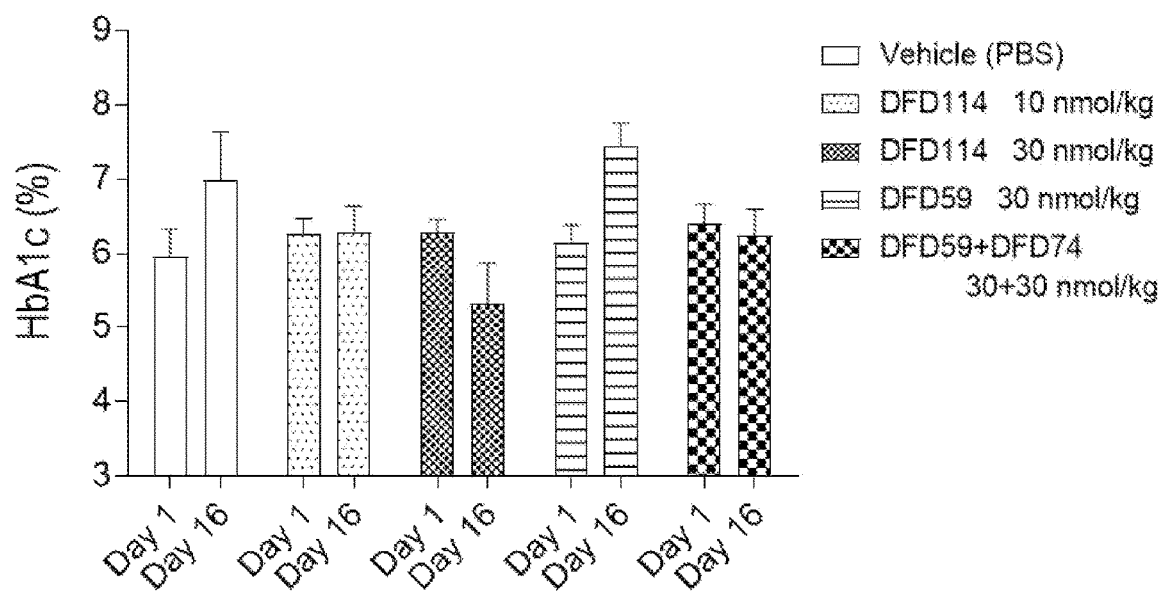
FIG. 18 shows graphs indicating the changes in glycated hemoglobin levels in a db/db mouse model at the day of administration (1$^{st}$ day) and the 16$^{th}$ day after single subcutaneous injection of DFD114 or DFD59 and single subcutaneous injection of a combination of DFD59 and DFD74. The groups treated with dual function proteins showed stronger effects on reducing glycated hemoglobin levels than those treated with single function proteins or a combination thereof. Data are indicated as mean values and standard error of the mean.
Figure 18:
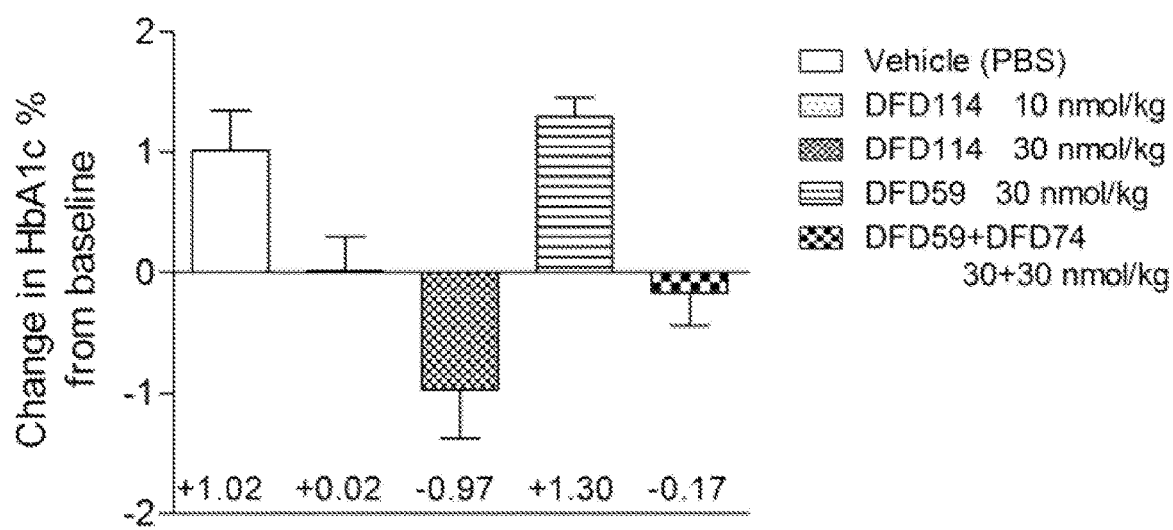

After the termination of the tests, the glycated hemoglobin levels indicative of the mean value of blood glucose were measured and the changes in mean blood glucose were analyzed in each test group. As shown in FIG. 18, the group treated with vehicle showed increased glycated hemoglobin levels after the termination of the tests as compared with the group before the administration, and the group treated with DFD59 showed a similar increase. The group treated with 30 nmol/kg of DFD114 showed the greatest decrease in glycated hemoglobin levels, and the group receiving combined administration showed the next highest effectiveness, followed by the group treated with 10 nmol/kg of DFD114. When evaluating the proteins by comparing them based on the decrease in glycated hemoglobin levels in each group treated, it was confirmed that the dual function protein DFD114 showed a stronger effect on lowering blood glucose level than GLP-1-Fc or Fc-FGF21 single function protein alone.

Experimental Example 10. Activity of Fusion Proteins in HFD/STZ Mice

Experimental Example 10-1. Experimental Method for Evaluating Activities in HFD/STZ Mice The effects of the dual function proteins on lowering blood glucose and body weight were compared and evaluated in another diabetic model, the HFD/STZ mouse model.

The conventional dietary-induced obesity mouse model (induced by feeding 60 kcal % high fat diet to C57BL/6 mice for eight weeks or longer) has weak hyperglycemic and diabetic features, although invokes insulin resistance. The HFD/STZ mice, which may compensate for the deficiencies of the conventional dietary-induced obesity mouse model, are capable of generating dysfunctional β cells of the pancreas and decreased secretion of insulin following a high fat diet (HFD) and administration of low level streptozotocin (STZ), and are used for pharmacological studies of type 2 diabetes. In order to induce the HFD/STZ mouse model, C57BL/6 mice were fed on a 60 kcal % high fat diet for four weeks, and then 50 mg/kg of STZ (Sigma, 85882) was administered intraperitoneally every day for 3 days to induce dysfunction of the β cells of the pancreas. After feeding on the high fat diet for an additional 2 weeks, the mice with non-fasting blood glucose levels of 200 mg/dL or higher were selected for the test. The mice were partitioned into groups (n=6/group) in order to have a similar mean value of body weight and caudal blood glucose levels one day before the drug treatment (Day 0), and the samples were subcutaneously administered once according to each of their respective dosages. Dulbecco's phosphate buffered saline (DPBS, Gibco, USA) was administered as the vehicle treatment, and the glucose concentration in the blood was measured using a glucose meter, GLUCODR™ (All Medicus, Korea). The non-fasting glucose levels and body weights were measured every day until the $14^{th}$ day after administration. Glycated hemoglobin levels were also measured in each group before the administration and after the test. The glycated hemoglobin levels were calculated using a DCA™ 2000 HbA1c kit (Siemens, 5035C).

Experimental Example 10-2. Activity in HFD/STZ Mice

The changes in non-fasting blood glucose levels and body weights over time in male HFD/STZ mice were observed after single subcutaneous injection of 3 nmol/kg or 10 nmol/kg of dual function protein DFD114, 10 nmol/kg of Fc-fused GLP-1 mutant DFD59, or 10 nmol/kg of each of the Fc-fused FGF21 mutants DFD72 and DFD74. DFD59 and DFD74 were also subcutaneously injected once at 10 nmol/kg each in order to compare the effect of combined administration of the single function proteins with that of the dual function protein.

Figure 19:
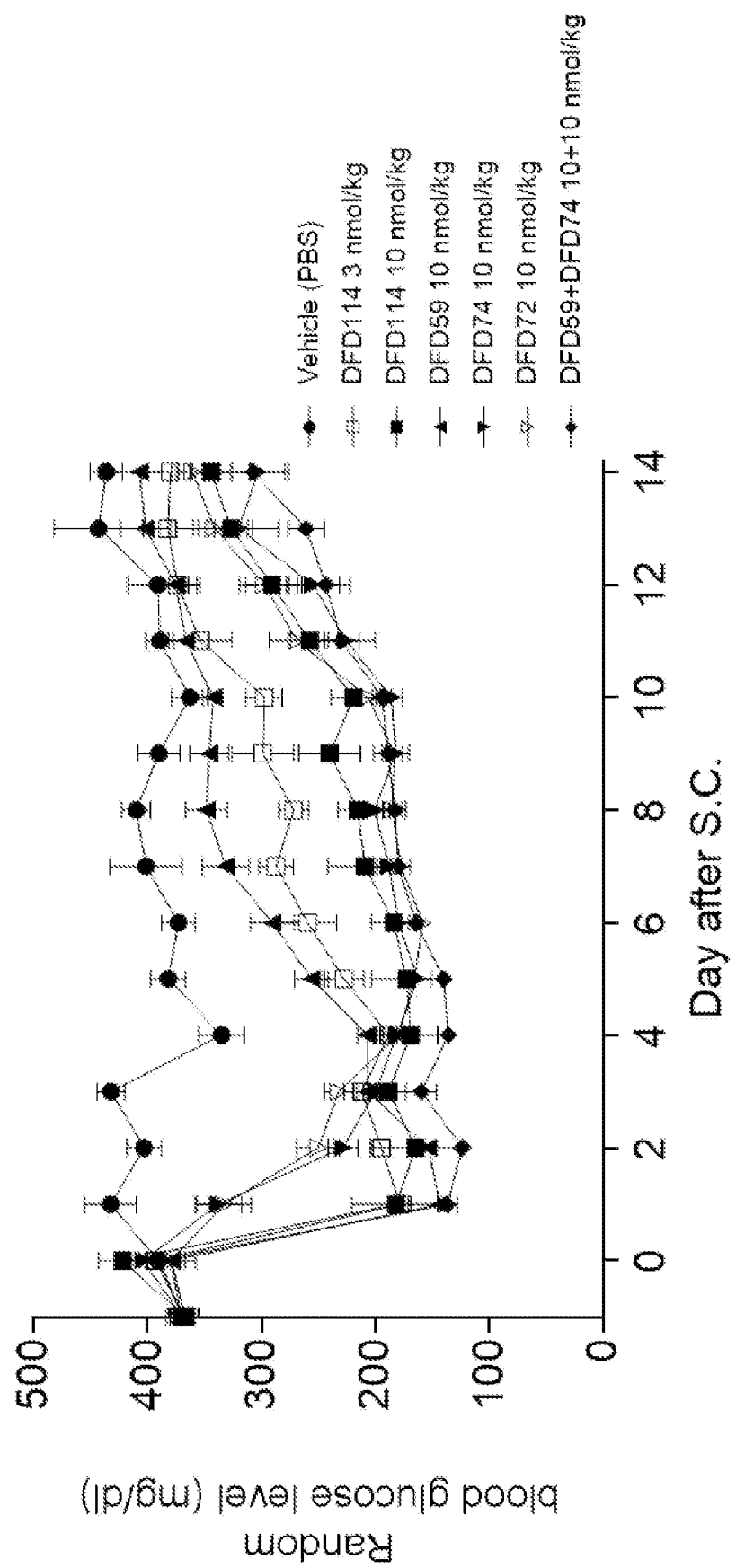
FIG. 19 shows the blood glucose levels in an HFD/STZ mouse model after single subcutaneous injection of DFD114, DFD59, DFD74 or DFD72 and single subcutaneous injection of combination of DFD59 and DFD74. The groups treated with dual function proteins showed stronger effects on lowering blood glucose levels than those treated with single function proteins. Data are indicated as mean values and standard error of the mean (S.E.M.).

As shown in FIG. 19, regarding the changes in blood glucose levels until the 4 day, DFD72 and DFD74 (long-acting FGF21 single function proteins) administration resulted in slower reductions of blood glucose, while DFD114 (long-acting protein including GLP-1), DFD59 and combined administration of DFD59 and DFD74 showed a more rapid reduction of blood glucose from the $1^{st}$ day of administration. Similar to the results in db/db mice, DFD59 showed a sharp reduction in blood glucose at an early stage, but the reduction of blood glucose disappeared slowly after the $4^{th}$ day. DFD114 showed a similar pattern at the low dose of 3 nmol/kg. In the groups treated with 10 nmol/kg of DFD114, DFD72, DFD74 and combined administration, similar non-fasting blood glucose profiles were observed.

Figure 20:
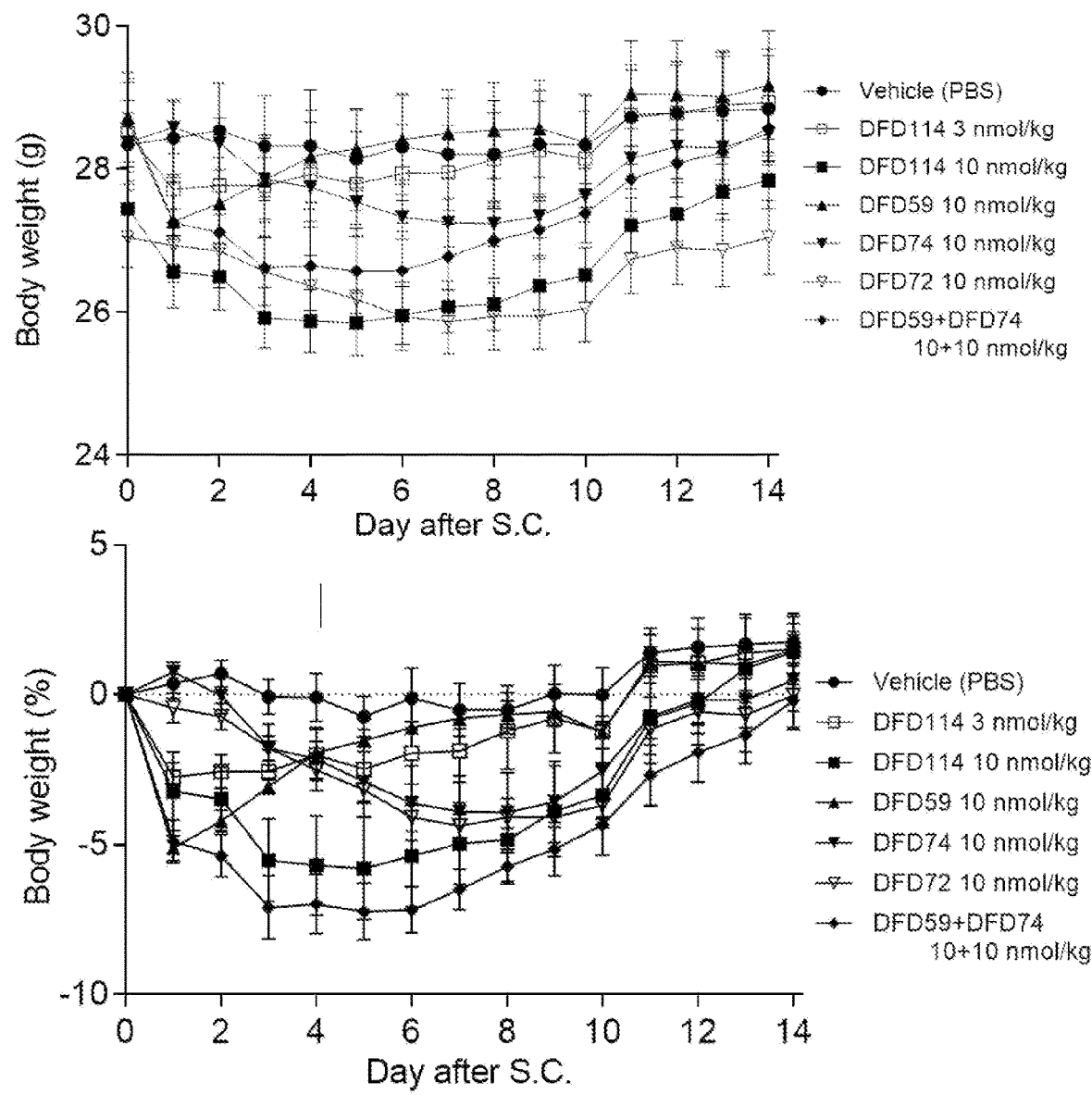
FIG. 20 shows the changes in body weights in the HFD/STZ mouse model from the day of administration to the 14$^{th}$ day after single subcutaneous injection of DFD59, DFD72, DFD74 or DFD114 and single subcutaneous injection of combination of DFD59 and DFD74. The groups treated with dual function proteins showed stronger effects on reducing body weight than those treated with single function proteins. Data are indicated as mean values and standard error of the mean (S.E.M.).

As for the effect on body weight reduction, the group treated with combined administration of DFD59 and DFD74 showed the greatest effect on body weight reduction (7 to 8%), and the group treated with 10 nmol/kg of DFD114 also showed an outstanding effect on reducing body weight (approximately 6%) (FIG. 20). The group treated with DFD59 exhibited a reduction in body weight by 5% at the $1^{st}$ day after administration, but the effect disappeared after the $2^{nd}$ day and became similar to that of the vehicle group after the $7^{th}$ day. The group treated with each of the long-acting FGF21 single function proteins DFD72 and DFD74 showed a slower reduction in body weight by 4 to 5% until the $7^{th}$ day after the administration, and the effect disappeared after the $10^{th}$ day.

Figure 21:
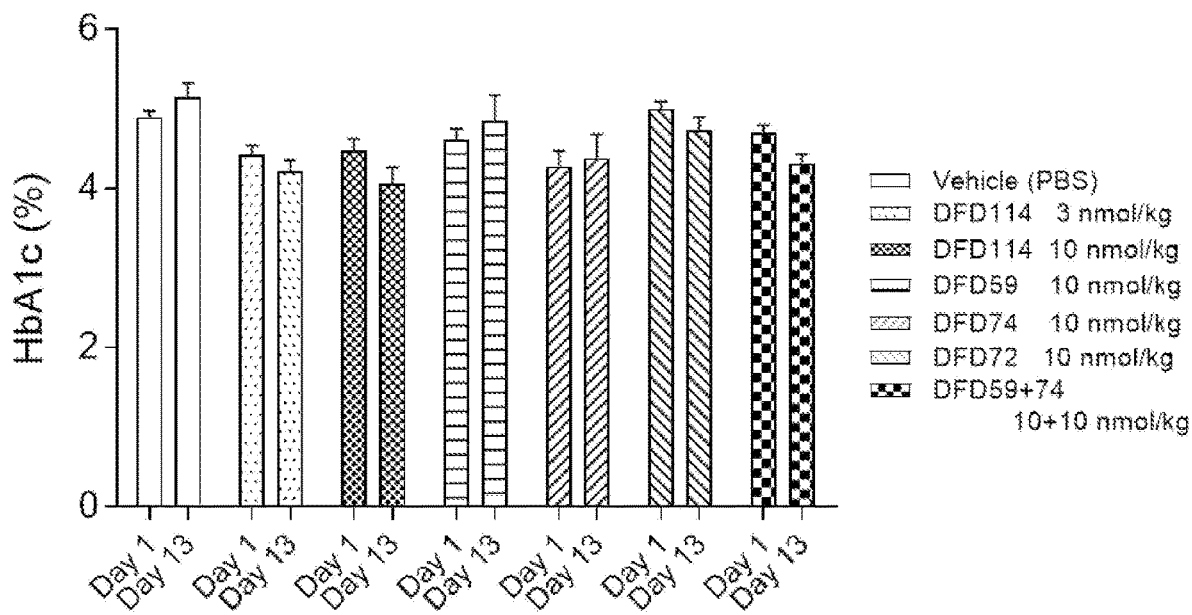
FIG. 21 shows the changes in glycated hemoglobin levels in the HFD/STZ mouse model at the day of administration (1$^{st}$ day) and the 16$^{th}$ day after single subcutaneous injection of DFD59, DFD72, DFD74 or DFD114 and single subcutaneous injection of combination of DFD59 and DFD74. The groups treated with dual function proteins showed stronger effects on reducing glycated hemoglobin levels than those treated with single function proteins or a combination thereof. Data are indicated as mean values and standard error of the mean.
Figure 21:
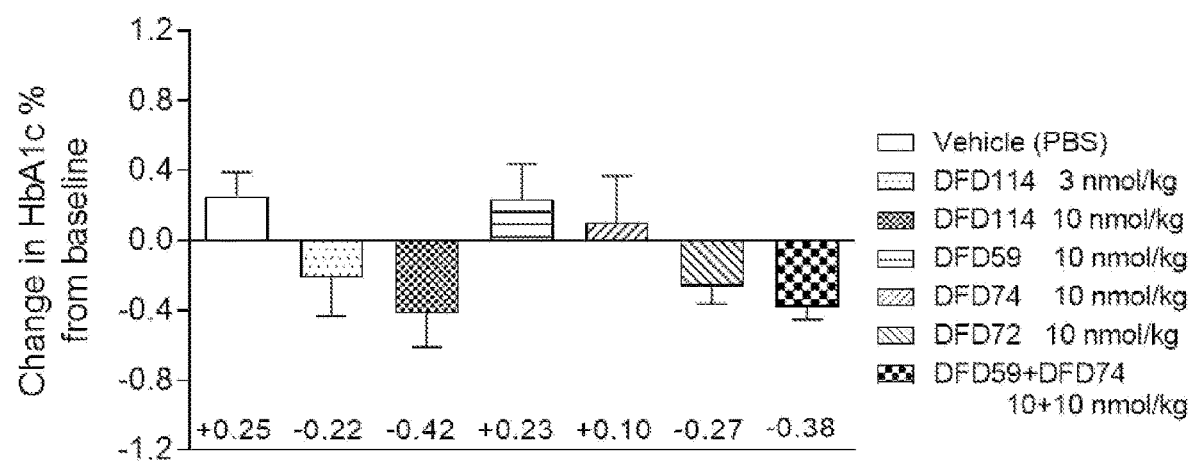

After the termination of the tests, the glycated hemoglobin levels indicative of the mean value of blood glucose were measured and the changes in mean blood glucose were analyzed in each test group (FIG. 21). The vehicle group had an increase in glycated hemoglobin levels after the termination of the test as compared with before administration, and the group treated with DFD59 showed a similar increase. In contrast, the group treated with DFD114 showed reductions in glycated hemoglobin levels in a dose-dependent manner, and the group treated with 10 nmol/kg of DFD114 had the greatest effect in terms of reduced glycated hemoglobin levels (−0.42%). The group treated with combined administration of DFD59 and DFD74 showed reduced glycated hemoglobin levels (−0.38%) similar to that of DFD114. For the long-acting FGF21 single function proteins, it was observed that DFD72 was superior to DFD74. Comparing the proteins based on the reduced levels of glycated hemoglobin in each group, it was confirmed that the dual function protein DFD114 was superior to both GLP-1-Fc and Fc-FGF21 single function proteins.

Experimental Example 11. Prediction and Evaluation of Immunogenicity

Experimental Example 11-1. Prediction Method for Immunogenicity and Results

In order to predict the potential immunogenicity of dual function proteins, in silico analysis of immunogenicity was performed for each protein.

Specifically, the potential immunogenicity of dual function proteins was rapidly screened by using ITOPE™ and TCED™ methods (Prediction of immunogenicity of therapeutic proteins: validity of computational tools, BioDrugs, 2010). According to the two methods, the T-cell epitope may be more accurately predicted as compared with the in silico analytical method which depends on MHC class 11 binding analysis only.

Experimental Example 11-2. Ex Vivo Evaluation Method for Immunogenicity and Results In order to evaluate the potential immunogenicity of dual function proteins, EPISCREEN™ analysis (Increased brain bio-distribution and chemical stability and decreased immunogenicity of an engineered variant of GDNF, Exp Neurol, 2015) was performed. When immunogenicity is detected, the amino acid sequences inducing immunogenicity may be identified through T-cell epitope mapping, and deaminized mutants with minimized immunogenicity may be designed and prepared via in silico prediction to reevaluate immunogenicity.

The invention claimed is:

1. A dual function protein comprising a fibroblast growth factor 21 (FGF21) mutant protein; a biologically active protein, or a biologically active mutant or biologically active fragment thereof, and an Fc region of an immunoglobulin, wherein the FGF21 mutant protein comprises one mutation selected from the group consisting of the following mutations (a), (b), (c), (d), and (e):

(a) a substitution of the amino acids at positions 98 to 101 from the N-terminus of a wild-type FGF21 protein with the amino acid sequence of EIRP (SEQ ID NO: 68);

(b) a substitution of the amino acids at positions 170 to 174 from the N-terminus of a wild-type FGF21 protein with the amino acid sequence of TGLEAV (SEQ ID NO: 69);

(c) a substitution of the amino acids at positions 170 to 174 from the N-terminus of a wild-type FGF21 protein with the amino acid sequence of TGLEAN (SEQ ID NO: 70);

(d) a substitution of the amino acid at position 174 from the N-terminus of a wild-type FGF21 protein with the amino acid N; and (e) a combination of the (a) and (b), a combination of the (a) and (c), or a combination of the (a) and (d), and wherein the wild-type FGF21 protein in (a), (b), (c), and (d) comprises the amino acid sequence of SEQ ID NO: 1.

2. The dual function protein of claim 1, wherein the amino acid residue N of the FGF21 mutant protein introduced by a mutation (c) or (d) is glycosylated.

3. The dual function protein of claim 1, wherein the biologically active protein is one selected from the group consisting of insulin, C-peptide, leptin, glucagon, gastrin, gastric inhibitory polypeptide (GIP), amylin, calcitonin, cholecystokinin, peptide YY, neuropeptide Y, bone morphogenetic protein-6 (BMP-6), bone morphogenetic protein-9 (BMP-9), oxyntomodulin, oxytocin, glucagon-like peptide-1 (GLP-1), glucagon-like peptide-2 (GLP-2), irisin, fibronectin type III domain-containing protein 5 (FNDC5), apelin, adiponectin, C1q and tumor necrosis factor related protein (CTRP family), resistin, visfatin, omentin, retinol binding protein-4 (RBP-4), glicentin, angiopoietin, interleukin-22 (IL-22), exendin-4, and growth hormone.

4. The dual function protein of claim 3, wherein the biologically active protein is one selected from GLP-1, a biologically active mutant thereof, and exendin-4.

5. The dual function protein of claim 4, wherein the mutant of GLP-1 comprises any one of the amino acid sequences of SEQ ID NO: 43 to 46.

6. The dual function protein of claim 1, wherein the FGF21 mutant protein has any one of the amino acid sequences of SEQ ID NO: 6, 7, 8, 10, 11, 12, 13, 14, 15, 16, 17, 19, 20, 21, 22, or 23.

7. The dual function protein of claim 1, wherein the dual function protein further comprises a linker.

8. The dual function protein of claim 7, wherein the linker connects the FGF21 mutant protein to the Fc region of the immunoglobulin.

9. The dual function protein of claim 8, wherein the linker is connected to the C-terminus of the Fc region of the immunoglobulin and the N-terminus of the FGF21 mutant protein.

10. The dual function protein of claim 8, wherein the linker is a peptide consisting of 10 to 30 amino acid residues.

11. The dual function protein of claim 10, wherein the linker comprises any one of the amino acid sequences of SEQ ID NO: 2 to 5.

12. The dual function protein of claim 1, wherein the Fc region of the immunoglobulin is any one of the Fc region of IgG1, IgG2, IgG3, IgG4 and IgD, or a hybrid Fc containing a combination thereof.

13. The dual function protein of claim 12, wherein the hybrid Fc comprises an IgG4 region and an IgD region.

14. The dual function protein of claim 1, wherein the dual function protein comprises, in the order from the N-terminus to the C-terminus, the biologically active protein, the Fc region of the immunoglobulin, and the FGF21 mutant protein.

15. The dual function protein of claim 14, wherein a linker is additionally connected between the Fc region of the immunoglobulin and the FGF21 mutant protein.

16. The dual function protein of claim 15, wherein the linker is a peptide consisting of 10 to 30 amino acid residues.

17. The dual function protein of claim 15, wherein the linker has any one of the amino acid sequences of SEQ ID NO: 2 to 5.

18. The dual function protein of claim 1, wherein the dual function protein comprises the amino acid sequence of SEQ ID NO: 65.

19. The dual function protein of claim 1, wherein the dual function protein comprises the amino acid sequence of SEQ ID NO: 66.

20. The dual function protein of claim 1, wherein the dual function protein comprises the amino acid sequence of SEQ ID NO: 67.

21. A pharmaceutical composition comprising the dual function protein according to claim 1 and a pharmaceutically acceptable formulating material.

22. A method selected from the group consisting of:
reducing blood glucose level in a subject;
reducing body weight in a subject;
reducing triglyceride or low-density lipoprotein levels in a subject; and
improving insulin sensitivity in a subject,
wherein the method comprises administering a therapeutically effective amount of the pharmaceutical composition of claim 21 to the subject, and
wherein the subject has diabetes, obesity, dyslipidemia, metabolic syndrome, non-alcoholic fatty liver disease, or non-alcoholic steatohepatitis.

23. The method of claim 22, wherein the subject is obese.

24. The method of claim 22, wherein the subject has diabetes.

25. The dual function protein of claim 1, wherein the mutation is (a) or (d) and the FGF21 mutant protein further comprises one or more mutations selected from the group consisting of the following mutations (f) and (g):
(f) a substitution of the amino acid at position 170 from the N-terminus of the wild-type FGF21 protein with the amino acid N; and
(g) a substitution of the amino acid at position 180 from the N-terminus of the wild-type FGF21 protein with the amino acid E.

* * * * *

SEQUENCE LISTING

```
<160> NUMBER OF SEQ ID NOS: 83

<210> SEQ ID NO 1
<211> LENGTH: 181
<212> TYPE: PRT
<213> ORGANISM: Homo sapiens
<220> FEATURE:
<223> OTHER INFORMATION: human FGF21

<400> SEQUENCE: 1

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180
```

```
<210> SEQ ID NO 2
<211> LENGTH: 30
<212> TYPE: PRT
<213> ORGANISM: Artificial Sequence
<220> FEATURE:
<223> OTHER INFORMATION: linker

<400> SEQUENCE: 2

Ala Lys Ala Thr Thr Ala Pro Ala Thr Thr Arg Asn Thr Gly Arg Gly
1               5                   10                  15

Gly Glu Glu Lys Lys Lys Glu Lys Glu Lys Glu Glu Gln Glu
            20                  25                  30

<210> SEQ ID NO 3
<211> LENGTH: 17
<212> TYPE: PRT
<213> ORGANISM: Artificial Sequence
<220> FEATURE:
<223> OTHER INFORMATION: linker

<400> SEQUENCE: 3

Ala Lys Ala Thr Thr Ala Pro Ala Thr Thr Arg Asn Thr Gly Arg Gly
1               5                   10                  15

Gly

<210> SEQ ID NO 4
<211> LENGTH: 15
<212> TYPE: PRT
<213> ORGANISM: Artificial Sequence
<220> FEATURE:
<223> OTHER INFORMATION: linker

<400> SEQUENCE: 4

Gly Gly Gly Gly Ser Gly Gly Gly Gly Ser Gly Gly Gly Gly Ser
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: linker

<400> SEQUENCE: 5

Gly Gly Gly Gly Ser Gly Gly Gly Gly Ser Gly Gly Gly Gly Ser Ala
1               5                   10                  15

<210> SEQ ID NO 6
<211> LENGTH: 181
<212> TYPE: PRT
<213> ORGANISM: Artificial Sequence
<220> FEATURE:
<223> OTHER INFORMATION: FGF21 variant

<400> SEQUENCE: 6

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
                35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
```

```
                65                  70                  75                  80
Ala Leu Tyr Gly Ser Leu His Phe Asp Pro Glu Ala Cys Ser Phe Arg
                    85                  90                  95

Glu Glu Ile Arg Pro Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 7
<211> LENGTH: 182
<212> TYPE: PRT
<213> ORGANISM: Artificial Sequence
<220> FEATURE:
<223> OTHER INFORMATION: FGF21 variant

<400> SEQUENCE: 7

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                    85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Thr Gly Leu Glu Ala Val Arg
                165                 170                 175

Ser Pro Ser Tyr Ala Ser
            180

<210> SEQ ID NO 8
<211> LENGTH: 182
<212> TYPE: PRT
<213> ORGANISM: Artificial Sequence
<220> FEATURE:
<223> OTHER INFORMATION: FGF21 variant

<400> SEQUENCE: 8
```

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Thr Gly Leu Glu Ala Asn Arg
                165                 170                 175

Ser Pro Ser Tyr Ala Ser
            180

<210> SEQ ID NO 9
<211> LENGTH: 181
<212> TYPE: PRT
<213> ORGANISM: Artificial Sequence
<220> FEATURE:
<223> OTHER INFORMATION: FGF21 variant

<400> SEQUENCE: 9

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Asn Pro Ser Gln Gly Arg Ser
                165                 170                 175

Pro Ser Tyr Ala Ser
            180

<210> SEQ ID NO 10
<211> LENGTH: 181
<212> TYPE: PRT
<213> ORGANISM: Artificial Sequence
<220> FEATURE:
<223> OTHER INFORMATION: FGF21 variant

<400> SEQUENCE: 10

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Asn Arg Ser
                165                 170                 175

Pro Ser Tyr Ala Ser
            180

<210> SEQ ID NO 11
<211> LENGTH: 182
<212> TYPE: PRT
<213> ORGANISM: Artificial Sequence
<220> FEATURE:
<223> OTHER INFORMATION: FGF21 variant

<400> SEQUENCE: 11

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Glu Ile Arg Pro Asp Gly Tyr Asn Val Tyr Gln Ser Glu Ala His
            100                 105                 110

```
Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Thr Gly Leu Glu Ala Val Arg
                165                 170                 175

Ser Pro Ser Tyr Ala Ser
                180

<210> SEQ ID NO 12
<211> LENGTH: 182
<212> TYPE: PRT
<213> ORGANISM: Artificial Sequence
<220> FEATURE:
<223> OTHER INFORMATION: FGF21 variant

<400> SEQUENCE: 12

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Glu Ile Arg Pro Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Thr Gly Leu Glu Ala Asn Arg
                165                 170                 175

Ser Pro Ser Tyr Ala Ser
                180

<210> SEQ ID NO 13
<211> LENGTH: 181
<212> TYPE: PRT
<213> ORGANISM: Artificial Sequence
<220> FEATURE:
<223> OTHER INFORMATION: FGF21 variant

<400> SEQUENCE: 13

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
```

```
                35                  40                  45
Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                85                  90                  95

Glu Glu Ile Arg Pro Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Asn Pro Ser Gln Gly Arg Ser
                165                 170                 175

Pro Ser Tyr Ala Ser
            180

<210> SEQ ID NO 14
<211> LENGTH: 181
<212> TYPE: PRT
<213> ORGANISM: Artificial Sequence
<220> FEATURE:
<223> OTHER INFORMATION: FGF21 variant

<400> SEQUENCE: 14

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                85                  90                  95

Glu Glu Ile Arg Pro Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Asn Arg Ser
                165                 170                 175

Pro Ser Tyr Ala Ser
            180

<210> SEQ ID NO 15
<211> LENGTH: 181
<212> TYPE: PRT
```

<213> ORGANISM: Artificial Sequence
<220> FEATURE:
<223> OTHER INFORMATION: FGF21 variant

<400> SEQUENCE: 15

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Glu Ile Arg Pro Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Glu Ser
            180
```

<210> SEQ ID NO 16
<211> LENGTH: 182
<212> TYPE: PRT
<213> ORGANISM: Artificial Sequence
<220> FEATURE:
<223> OTHER INFORMATION: FGF21 variant

<400> SEQUENCE: 16

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140
```

```
Ala Leu Pro Glu Pro Pro Gly Ile Leu Ala Pro Gln Pro Pro Asp Val
145                 150                 155                 160

Gly Ser Ser Asp Pro Leu Ser Met Val Thr Gly Leu Glu Ala Val Arg
                165                 170                 175

Ser Pro Ser Tyr Glu Ser
            180

<210> SEQ ID NO 17
<211> LENGTH: 182
<212> TYPE: PRT
<213> ORGANISM: Artificial Sequence
<220> FEATURE:
<223> OTHER INFORMATION: FGF21 variant

<400> SEQUENCE: 17

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Thr Gly Leu Glu Ala Asn Arg
                165                 170                 175

Ser Pro Ser Tyr Glu Ser
            180

<210> SEQ ID NO 18
<211> LENGTH: 181
<212> TYPE: PRT
<213> ORGANISM: Artificial Sequence
<220> FEATURE:
<223> OTHER INFORMATION: FGF21 variant

<400> SEQUENCE: 18

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80
```

Ala Leu Tyr Gly Ser Leu His Phe Asp Pro Glu Ala Cys Ser Phe Arg
            85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Asn Pro Ser Gln Gly Arg Ser
                165                 170                 175

Pro Ser Tyr Glu Ser
            180

<210> SEQ ID NO 19
<211> LENGTH: 181
<212> TYPE: PRT
<213> ORGANISM: Artificial Sequence
<220> FEATURE:
<223> OTHER INFORMATION: FGF21 variant

<400> SEQUENCE: 19

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
            85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Asn Arg Ser
                165                 170                 175

Pro Ser Tyr Glu Ser
            180

<210> SEQ ID NO 20
<211> LENGTH: 182
<212> TYPE: PRT
<213> ORGANISM: Artificial Sequence
<220> FEATURE:
<223> OTHER INFORMATION: FGF21 variant

<400> SEQUENCE: 20

His Pro Ile Pro Asp Ser Ser Pro Leu Leu Gln Phe Gly Gly Gln Val

```
            1               5                  10                 15
          Arg Gln Arg Tyr Leu Tyr Thr Asp Asp Ala Gln Gln Thr Glu Ala His
                          20                 25                 30

Leu Glu Ile Arg Glu Asp Gly Thr Val Gly Gly Ala Ala Asp Gln Ser
                          35                 40             45

Pro Glu Ser Leu Leu Gln Leu Lys Ala Leu Lys Pro Gly Val Ile Gln
                  50              55                 60

Ile Leu Gly Val Lys Thr Ser Arg Phe Leu Cys Gln Arg Pro Asp Gly
          65              70                 75                 80

Ala Leu Tyr Gly Ser Leu His Phe Asp Pro Glu Ala Cys Ser Phe Arg
                          85                 90                 95

Glu Glu Ile Arg Pro Asp Gly Tyr Asn Val Tyr Gln Ser Glu Ala His
                          100                105                110

Gly Leu Pro Leu His Leu Pro Gly Asn Lys Ser Pro His Arg Asp Pro
                          115                120                125

Ala Pro Arg Gly Pro Ala Arg Phe Leu Pro Leu Pro Gly Leu Pro Pro
                          130                135            140

Ala Leu Pro Glu Pro Pro Gly Ile Leu Ala Pro Gln Pro Pro Asp Val
          145                 150                155                160

Gly Ser Ser Asp Pro Leu Ser Met Val Thr Gly Leu Glu Ala Val Arg
                          165                170                175

Ser Pro Ser Tyr Glu Ser
                          180

<210> SEQ ID NO 21
<211> LENGTH: 182
<212> TYPE: PRT
<213> ORGANISM: Artificial Sequence
<220> FEATURE:
<223> OTHER INFORMATION: FGF21 variant

<400> SEQUENCE: 21

His Pro Ile Pro Asp Ser Ser Pro Leu Leu Gln Phe Gly Gly Gln Val
          1               5                  10                 15

Arg Gln Arg Tyr Leu Tyr Thr Asp Asp Ala Gln Gln Thr Glu Ala His
                          20                 25                 30

Leu Glu Ile Arg Glu Asp Gly Thr Val Gly Gly Ala Ala Asp Gln Ser
                          35                 40             45

Pro Glu Ser Leu Leu Gln Leu Lys Ala Leu Lys Pro Gly Val Ile Gln
                  50              55                 60

Ile Leu Gly Val Lys Thr Ser Arg Phe Leu Cys Gln Arg Pro Asp Gly
          65              70                 75                 80

Ala Leu Tyr Gly Ser Leu His Phe Asp Pro Glu Ala Cys Ser Phe Arg
                          85                 90                 95

Glu Glu Ile Arg Pro Asp Gly Tyr Asn Val Tyr Gln Ser Glu Ala His
                          100                105                110

Gly Leu Pro Leu His Leu Pro Gly Asn Lys Ser Pro His Arg Asp Pro
                          115                120                125

Ala Pro Arg Gly Pro Ala Arg Phe Leu Pro Leu Pro Gly Leu Pro Pro
                          130                135            140

Ala Leu Pro Glu Pro Pro Gly Ile Leu Ala Pro Gln Pro Pro Asp Val
          145                 150                155                160

Gly Ser Ser Asp Pro Leu Ser Met Val Thr Gly Leu Glu Ala Asn Arg
                          165                170                175

Ser Pro Ser Tyr Glu Ser
```

180

<210> SEQ ID NO 22
<211> LENGTH: 181
<212> TYPE: PRT
<213> ORGANISM: Artificial Sequence
<220> FEATURE:
<223> OTHER INFORMATION: FGF21 variant

<400> SEQUENCE: 22

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Glu Ile Arg Pro Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Asn Pro Ser Gln Gly Arg Ser
                165                 170                 175

Pro Ser Tyr Glu Ser
            180
```

<210> SEQ ID NO 23
<211> LENGTH: 181
<212> TYPE: PRT
<213> ORGANISM: Artificial Sequence
<220> FEATURE:
<223> OTHER INFORMATION: FGF21 variant

<400> SEQUENCE: 23

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Glu Ile Arg Pro Asp Gly Tyr Asn Val Tyr Gln Ser Glu Ala His
            100                 105                 110
```

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Asn Arg Ser
                165                 170                 175

Pro Ser Tyr Glu Ser
            180

<210> SEQ ID NO 24
<211> LENGTH: 229
<212> TYPE: PRT
<213> ORGANISM: Artificial Sequence
<220> FEATURE:
<223> OTHER INFORMATION: Human IgG4 Fc

<400> SEQUENCE: 24

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 25
<211> LENGTH: 228
<212> TYPE: PRT
<213> ORGANISM: Artificial Sequence
<220> FEATURE:
<223> OTHER INFORMATION: Human IgG4 Fc variant

<400> SEQUENCE: 25

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225

<210> SEQ ID NO 26
<211> LENGTH: 223
<212> TYPE: PRT
<213> ORGANISM: Artificial Sequence
<220> FEATURE:
<223> OTHER INFORMATION: Hybrid Fc variant

<400> SEQUENCE: 26

Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser Gln Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
            100                 105                 110

Ser Lys Ala Lys Gly Gln Pro Arg Glu Pro Gln Val Tyr Thr Leu Pro
        115                 120                 125

```
Pro Ser Gln Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
        195                 200                 205

His Asn His Tyr Thr Gln Lys Ser Leu Ser Leu Ser Leu Gly Lys
    210                 215                 220

<210> SEQ ID NO 27
<211> LENGTH: 435
<212> TYPE: PRT
<213> ORGANISM: Artificial Sequence
<220> FEATURE:
<223> OTHER INFORMATION: modified FGF21 variant connected to hybrid Fc

<400> SEQUENCE: 27

Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser Gln Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Gln Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
        195                 200                 205

His Asn His Tyr Thr Gln Lys Ser Leu Ser Leu Ser Leu Gly Lys Ala
    210                 215                 220

Lys Ala Thr Thr Ala Pro Ala Thr Thr Arg Asn Thr Gly Arg Gly Gly
225                 230                 235                 240

Glu Glu Lys Lys Lys Glu Lys Glu Lys Glu Glu Gln Glu His Pro Ile
                245                 250                 255

Pro Asp Ser Ser Pro Leu Leu Gln Phe Gly Gly Gln Val Arg Gln Arg
            260                 265                 270
```

```
Tyr Leu Tyr Thr Asp Asp Ala Gln Gln Thr Glu Ala His Leu Glu Ile
        275                 280                 285

Arg Glu Asp Gly Thr Val Gly Ala Ala Asp Gln Ser Pro Glu Ser
    290                 295                 300

Leu Leu Gln Leu Lys Ala Leu Lys Pro Gly Val Ile Gln Ile Leu Gly
305                 310                 315                 320

Val Lys Thr Ser Arg Phe Leu Cys Gln Arg Pro Asp Gly Ala Leu Tyr
                325                 330                 335

Gly Ser Leu His Phe Asp Pro Glu Ala Cys Ser Phe Arg Glu Glu Ile
            340                 345                 350

Arg Pro Asp Gly Tyr Asn Val Tyr Gln Ser Glu Ala His Gly Leu Pro
        355                 360                 365

Leu His Leu Pro Gly Asn Lys Ser Pro His Arg Asp Pro Ala Pro Arg
    370                 375                 380

Gly Pro Ala Arg Phe Leu Pro Leu Pro Gly Leu Pro Pro Ala Leu Pro
385                 390                 395                 400

Glu Pro Pro Gly Ile Leu Ala Pro Gln Pro Pro Asp Val Gly Ser Ser
                405                 410                 415

Asp Pro Leu Ser Met Val Thr Gly Leu Glu Ala Val Arg Ser Pro Ser
            420                 425                 430

Tyr Ala Ser
        435

<210> SEQ ID NO 28
<211> LENGTH: 422
<212> TYPE: PRT
<213> ORGANISM: Artificial Sequence
<220> FEATURE:
<223> OTHER INFORMATION: modified FGF21 variant connected to hybrid Fc

<400> SEQUENCE: 28

Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
                20                  25                  30

Pro Glu Val Thr Cys Val Val Asp Val Ser Gln Glu Asp Pro Glu
            35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
                100                 105                 110

Ser Lys Ala Lys Gly Gln Pro Arg Glu Pro Gln Val Tyr Thr Leu Pro
            115                 120                 125

Pro Ser Gln Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190
```

Trp Gln Glu Gly Asn Val Phe Ser Cys Ser Val Met His Glu Ala Leu
            195                 200                 205

His Asn His Tyr Thr Gln Lys Ser Leu Ser Leu Ser Leu Gly Lys Ala
        210                 215                 220

Lys Ala Thr Thr Ala Pro Ala Thr Thr Arg Asn Thr Gly Arg Gly Gly
225                 230                 235                 240

His Pro Ile Pro Asp Ser Ser Pro Leu Leu Gln Phe Gly Gly Gln Val
            245                 250                 255

Arg Gln Arg Tyr Leu Tyr Thr Asp Asp Ala Gln Gln Thr Glu Ala His
        260                 265                 270

Leu Glu Ile Arg Glu Asp Gly Thr Val Gly Gly Ala Ala Asp Gln Ser
        275                 280                 285

Pro Glu Ser Leu Leu Gln Leu Lys Ala Leu Lys Pro Gly Val Ile Gln
        290                 295                 300

Ile Leu Gly Val Lys Thr Ser Arg Phe Leu Cys Gln Arg Pro Asp Gly
305                 310                 315                 320

Ala Leu Tyr Gly Ser Leu His Phe Asp Pro Glu Ala Cys Ser Phe Arg
            325                 330                 335

Glu Leu Leu Leu Glu Asp Gly Tyr Asn Val Tyr Gln Ser Glu Ala His
        340                 345                 350

Gly Leu Pro Leu His Leu Pro Gly Asn Lys Ser Pro His Arg Asp Pro
        355                 360                 365

Ala Pro Arg Gly Pro Ala Arg Phe Leu Pro Leu Pro Gly Leu Pro Pro
        370                 375                 380

Ala Leu Pro Glu Pro Pro Gly Ile Leu Ala Pro Gln Pro Pro Asp Val
385                 390                 395                 400

Gly Ser Ser Asp Pro Leu Ser Met Val Thr Gly Leu Glu Ala Val Arg
            405                 410                 415

Ser Pro Ser Tyr Ala Ser
            420

<210> SEQ ID NO 29
<211> LENGTH: 420
<212> TYPE: PRT
<213> ORGANISM: Artificial Sequence
<220> FEATURE:
<223> OTHER INFORMATION: modified FGF21 variant connected to hybrid Fc

<400> SEQUENCE: 29

Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser Gln Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
            85                  90                  95

Cys Lys Val Ser Asn Lys Gly Leu Pro Ser Ser Ile Glu Lys Thr Ile
        100                 105                 110

Ser Lys Ala Lys Gly Gln Pro Arg Glu Pro Gln Val Tyr Thr Leu Pro
    115                 120                 125

-continued

```
Pro Ser Gln Glu Glu Met Thr Lys Asn Gln Val Ser Leu Thr Cys Leu
            130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
        195                 200                 205

His Asn His Tyr Thr Gln Lys Ser Leu Ser Leu Ser Leu Gly Lys Gly
    210                 215                 220

Gly Gly Gly Ser Gly Gly Gly Ser Gly Gly Gly Ser His Pro
225                 230                 235                 240

Ile Pro Asp Ser Ser Pro Leu Leu Gln Phe Gly Gly Gln Val Arg Gln
                245                 250                 255

Arg Tyr Leu Tyr Thr Asp Asp Ala Gln Gln Thr Glu Ala His Leu Glu
            260                 265                 270

Ile Arg Glu Asp Gly Thr Val Gly Gly Ala Ala Asp Gln Ser Pro Glu
        275                 280                 285

Ser Leu Leu Gln Leu Lys Ala Leu Lys Pro Gly Val Ile Gln Ile Leu
    290                 295                 300

Gly Val Lys Thr Ser Arg Phe Leu Cys Gln Arg Pro Asp Gly Ala Leu
305                 310                 315                 320

Tyr Gly Ser Leu His Phe Asp Pro Glu Ala Cys Ser Phe Arg Glu Leu
                325                 330                 335

Leu Leu Glu Asp Gly Tyr Asn Val Tyr Gln Ser Glu Ala His Gly Leu
            340                 345                 350

Pro Leu His Leu Pro Gly Asn Lys Ser Pro His Arg Asp Pro Ala Pro
        355                 360                 365

Arg Gly Pro Ala Arg Phe Leu Pro Leu Pro Gly Leu Pro Pro Ala Leu
    370                 375                 380

Pro Glu Pro Pro Gly Ile Leu Ala Pro Gln Pro Pro Asp Val Gly Ser
385                 390                 395                 400

Ser Asp Pro Leu Ser Met Val Thr Gly Leu Glu Ala Val Arg Ser Pro
                405                 410                 415

Ser Tyr Ala Ser
            420

<210> SEQ ID NO 30
<211> LENGTH: 420
<212> TYPE: PRT
<213> ORGANISM: Artificial Sequence
<220> FEATURE:
<223> OTHER INFORMATION: modified FGF21 variant connected to hybrid Fc

<400> SEQUENCE: 30

Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser Gln Glu Asp Pro Glu
        35                  40                  45

Val Gln Phe Asn Trp Tyr Val Asp Gly Val Glu Val His Asn Ala Lys
    50                  55                  60
```

Thr Lys Pro Arg Glu Glu Gln Phe Asn Ser Thr Tyr Arg Val Val Ser
 65                  70                  75                  80

Val Leu Thr Val Leu His Gln Asp Trp Leu Asn Gly Lys Glu Tyr Lys
                 85                  90                  95

Cys Lys Val Ser Asn Lys Gly Leu Pro Ser Ser Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Gln Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
        195                 200                 205

His Asn His Tyr Thr Gln Lys Ser Leu Ser Leu Ser Leu Gly Lys Gly
210                 215                 220

Gly Gly Gly Ser Gly Gly Gly Ser Gly Gly Gly Ser His Pro
225                 230                 235                 240

Ile Pro Asp Ser Ser Pro Leu Leu Gln Phe Gly Gly Gln Val Arg Gln
                245                 250                 255

Arg Tyr Leu Tyr Thr Asp Asp Ala Gln Gln Thr Glu Ala His Leu Glu
            260                 265                 270

Ile Arg Glu Asp Gly Thr Val Gly Gly Ala Ala Asp Gln Ser Pro Glu
        275                 280                 285

Ser Leu Leu Gln Leu Lys Ala Leu Lys Pro Gly Val Ile Gln Ile Leu
290                 295                 300

Gly Val Lys Thr Ser Arg Phe Leu Cys Gln Arg Pro Asp Gly Ala Leu
305                 310                 315                 320

Tyr Gly Ser Leu His Phe Asp Pro Glu Ala Cys Ser Phe Arg Glu Leu
                325                 330                 335

Leu Leu Glu Asp Gly Tyr Asn Val Tyr Gln Ser Glu Ala His Gly Leu
            340                 345                 350

Pro Leu His Leu Pro Gly Asn Lys Ser Pro His Arg Asp Pro Ala Pro
        355                 360                 365

Arg Gly Pro Ala Arg Phe Leu Pro Leu Pro Gly Leu Pro Pro Ala Leu
370                 375                 380

Pro Glu Pro Pro Gly Ile Leu Ala Pro Gln Pro Pro Asp Val Gly Ser
385                 390                 395                 400

Ser Asp Pro Leu Ser Met Val Thr Gly Leu Glu Ala Asn Arg Ser Pro
                405                 410                 415

Ser Tyr Ala Ser
            420

<210> SEQ ID NO 31
<211> LENGTH: 419
<212> TYPE: PRT
<213> ORGANISM: Artificial Sequence
<220> FEATURE:
<223> OTHER INFORMATION: modified FGF21 variant connected to hybrid Fc

<400> SEQUENCE: 31

```
Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser Gln Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
                100                 105                 110

Ser Lys Ala Lys Gly Gln Pro Arg Glu Pro Gln Val Tyr Thr Leu Pro
            115                 120                 125

Pro Ser Gln Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
            195                 200                 205

His Asn His Tyr Thr Gln Lys Ser Leu Ser Leu Ser Leu Gly Lys Gly
            210                 215                 220

Gly Gly Gly Ser Gly Gly Gly Ser Gly Gly Gly Ser His Pro
225                 230                 235                 240

Ile Pro Asp Ser Ser Pro Leu Leu Gln Phe Gly Gly Gln Val Arg Gln
                245                 250                 255

Arg Tyr Leu Tyr Thr Asp Asp Ala Gln Gln Thr Glu Ala His Leu Glu
            260                 265                 270

Ile Arg Glu Asp Gly Thr Val Gly Gly Ala Ala Asp Gln Ser Pro Glu
            275                 280                 285

Ser Leu Leu Gln Leu Lys Ala Leu Lys Pro Gly Val Ile Gln Ile Leu
            290                 295                 300

Gly Val Lys Thr Ser Arg Phe Leu Cys Gln Arg Pro Asp Gly Ala Leu
305                 310                 315                 320

Tyr Gly Ser Leu His Phe Asp Pro Glu Ala Cys Ser Phe Arg Glu Leu
                325                 330                 335

Leu Leu Glu Asp Gly Tyr Asn Val Tyr Gln Ser Glu Ala His Gly Leu
            340                 345                 350

Pro Leu His Leu Pro Gly Asn Lys Ser Pro His Arg Asp Pro Ala Pro
            355                 360                 365

Arg Gly Pro Ala Arg Phe Leu Pro Leu Pro Gly Leu Pro Pro Ala Leu
370                 375                 380

Pro Glu Pro Pro Gly Ile Leu Ala Pro Gln Pro Pro Asp Val Gly Ser
385                 390                 395                 400

Ser Asp Pro Leu Ser Met Val Asn Pro Ser Gln Gly Arg Ser Pro Ser
                405                 410                 415
```

Tyr Ala Ser

<210> SEQ ID NO 32
<211> LENGTH: 419
<212> TYPE: PRT
<213> ORGANISM: Artificial Sequence
<220> FEATURE:
<223> OTHER INFORMATION: modified FGF21 variant connected to hybrid Fc

<400> SEQUENCE: 32

Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser Gln Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Gln Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
        195                 200                 205

His Asn His Tyr Thr Gln Lys Ser Leu Ser Leu Ser Leu Gly Lys Gly
    210                 215                 220

Gly Gly Gly Ser Gly Gly Gly Gly Ser Gly Gly Gly Gly Ser His Pro
225                 230                 235                 240

Ile Pro Asp Ser Ser Pro Leu Leu Gln Phe Gly Gly Gln Val Arg Gln
                245                 250                 255

Arg Tyr Leu Tyr Thr Asp Asp Ala Gln Gln Thr Glu Ala His Leu Glu
            260                 265                 270

Ile Arg Glu Asp Gly Thr Val Gly Gly Ala Ala Asp Gln Ser Pro Glu
        275                 280                 285

Ser Leu Leu Gln Leu Lys Ala Leu Lys Pro Gly Val Ile Gln Ile Leu
    290                 295                 300

Gly Val Lys Thr Ser Arg Phe Leu Cys Gln Arg Pro Asp Gly Ala Leu
305                 310                 315                 320

Tyr Gly Ser Leu His Phe Asp Pro Glu Ala Cys Ser Phe Arg Glu Leu
                325                 330                 335

Leu Leu Glu Asp Gly Tyr Asn Val Tyr Gln Ser Glu Ala His Gly Leu
            340                 345                 350

Pro Leu His Leu Pro Gly Asn Lys Ser Pro His Arg Asp Pro Ala Pro

```
            355                 360                 365
Arg Gly Pro Ala Arg Phe Leu Pro Leu Pro Gly Leu Pro Pro Ala Leu
            370                 375                 380

Pro Glu Pro Pro Gly Ile Leu Ala Pro Gln Pro Pro Asp Val Gly Ser
385                 390                 395                 400

Ser Asp Pro Leu Ser Met Val Asn Pro Ser Gln Gly Arg Ser Pro Ser
                    405                 410                 415

Tyr Ala Ser

<210> SEQ ID NO 33
<211> LENGTH: 419
<212> TYPE: PRT
<213> ORGANISM: Artificial Sequence
<220> FEATURE:
<223> OTHER INFORMATION: modified FGF21 variant connected to hybrid Fc

<400> SEQUENCE: 33

Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser Gln Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Gln Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
        195                 200                 205

His Asn His Tyr Thr Gln Lys Ser Leu Ser Leu Ser Leu Gly Lys Gly
    210                 215                 220

Gly Gly Gly Ser Gly Gly Gly Gly Ser Gly Gly Gly Ser His Pro
225                 230                 235                 240

Ile Pro Asp Ser Ser Pro Leu Leu Gln Phe Gly Gly Gln Val Arg Gln
                245                 250                 255

Arg Tyr Leu Tyr Thr Asp Asp Ala Gln Gln Thr Glu Ala His Leu Glu
            260                 265                 270

Ile Arg Glu Asp Gly Thr Val Gly Gly Ala Ala Asp Gln Ser Pro Glu
        275                 280                 285

Ser Leu Leu Gln Leu Lys Ala Leu Lys Pro Gly Val Ile Gln Ile Leu
    290                 295                 300
```

```
Gly Val Lys Thr Ser Arg Phe Leu Cys Gln Arg Pro Asp Gly Ala Leu
305                 310                 315                 320

Tyr Gly Ser Leu His Phe Asp Pro Glu Ala Cys Ser Phe Arg Glu Leu
                325                 330                 335

Leu Leu Glu Asp Gly Tyr Asn Val Tyr Gln Ser Glu Ala His Gly Leu
            340                 345                 350

Pro Leu His Leu Pro Gly Asn Lys Ser Pro His Arg Asp Pro Ala Pro
        355                 360                 365

Arg Gly Pro Ala Arg Phe Leu Pro Leu Pro Gly Leu Pro Pro Ala Leu
    370                 375                 380

Pro Glu Pro Pro Gly Ile Leu Ala Pro Gln Pro Pro Asp Val Gly Ser
385                 390                 395                 400

Ser Asp Pro Leu Ser Met Val Gly Pro Ser Gln Asn Arg Ser Pro Ser
                405                 410                 415

Tyr Ala Ser
```

<210> SEQ ID NO 34
<211> LENGTH: 419
<212> TYPE: PRT
<213> ORGANISM: Artificial Sequence
<220> FEATURE:
<223> OTHER INFORMATION: modified FGF21 variant connected to hybrid Fc

<400> SEQUENCE: 34

```
Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser Gln Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Gln Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
        195                 200                 205

His Asn His Tyr Thr Gln Lys Ser Leu Ser Leu Ser Leu Gly Lys Gly
    210                 215                 220

Gly Gly Gly Ser Gly Gly Gly Gly Ser Gly Gly Gly Gly Ser His Pro
225                 230                 235                 240
```

```
Ile Pro Asp Ser Ser Pro Leu Leu Gln Phe Gly Gly Gln Val Arg Gln
                245                 250                 255

Arg Tyr Leu Tyr Thr Asp Asp Ala Gln Gln Thr Glu Ala His Leu Glu
        260                 265                 270

Ile Arg Glu Asp Gly Thr Val Gly Gly Ala Ala Asp Gln Ser Pro Glu
            275                 280                 285

Ser Leu Leu Gln Leu Lys Ala Leu Lys Pro Gly Val Ile Gln Ile Leu
        290                 295                 300

Gly Val Lys Thr Ser Arg Phe Leu Cys Gln Arg Pro Asp Gly Ala Leu
305                 310                 315                 320

Tyr Gly Ser Leu His Phe Asp Pro Glu Ala Cys Ser Phe Arg Glu Leu
                325                 330                 335

Leu Leu Glu Asp Gly Tyr Asn Val Tyr Gln Ser Glu Ala His Gly Leu
            340                 345                 350

Pro Leu His Leu Pro Gly Asn Lys Ser Pro His Arg Asp Pro Ala Pro
        355                 360                 365

Arg Gly Pro Ala Arg Phe Leu Pro Leu Pro Gly Leu Pro Pro Ala Leu
            370                 375                 380

Pro Glu Pro Pro Gly Ile Leu Ala Pro Gln Pro Pro Asp Val Gly Ser
385                 390                 395                 400

Ser Asp Pro Leu Ser Met Val Gly Pro Ser Gln Gly Arg Ser Pro Ser
                405                 410                 415

Tyr Ala Ser

<210> SEQ ID NO 35
<211> LENGTH: 420
<212> TYPE: PRT
<213> ORGANISM: Artificial Sequence
<220> FEATURE:
<223> OTHER INFORMATION: modified FGF21 variant connected to hybrid Fc

<400> SEQUENCE: 35

Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser Gln Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Gln Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
```

```
                180             185             190
Trp Gln Glu Gly Asn Val Phe Ser Cys Ser Val Met His Glu Ala Leu
            195                 200                 205

His Asn His Tyr Thr Gln Lys Ser Leu Ser Leu Ser Leu Gly Lys Gly
        210                 215                 220

Gly Gly Gly Ser Gly Gly Gly Ser Gly Gly Gly Ser His Pro
225                 230                 235                 240

Ile Pro Asp Ser Ser Pro Leu Leu Gln Phe Gly Gly Gln Val Arg Gln
                245                 250                 255

Arg Tyr Leu Tyr Thr Asp Asp Ala Gln Gln Thr Glu Ala His Leu Glu
            260                 265                 270

Ile Arg Glu Asp Gly Thr Val Gly Gly Ala Ala Asp Gln Ser Pro Glu
        275                 280                 285

Ser Leu Leu Gln Leu Lys Ala Leu Lys Pro Gly Val Ile Gln Ile Leu
    290                 295                 300

Gly Val Lys Thr Ser Arg Phe Leu Cys Gln Arg Pro Asp Gly Ala Leu
305                 310                 315                 320

Tyr Gly Ser Leu His Phe Asp Pro Glu Ala Cys Ser Phe Arg Glu Glu
                325                 330                 335

Ile Arg Pro Asp Gly Tyr Asn Val Tyr Gln Ser Glu Ala His Gly Leu
            340                 345                 350

Pro Leu His Leu Pro Gly Asn Lys Ser Pro His Arg Asp Pro Ala Pro
        355                 360                 365

Arg Gly Pro Ala Arg Phe Leu Pro Leu Pro Gly Leu Pro Pro Ala Leu
    370                 375                 380

Pro Glu Pro Pro Gly Ile Leu Ala Pro Gln Pro Pro Asp Val Gly Ser
385                 390                 395                 400

Ser Asp Pro Leu Ser Met Val Thr Gly Leu Glu Ala Val Arg Ser Pro
                405                 410                 415

Ser Tyr Ala Ser
            420

<210> SEQ ID NO 36
<211> LENGTH: 420
<212> TYPE: PRT
<213> ORGANISM: Artificial Sequence
<220> FEATURE:
<223> OTHER INFORMATION: modified FGF21 variant connected to hybrid Fc

<400> SEQUENCE: 36

Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser Gln Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
            100                 105                 110

Ser Lys Ala Lys Gly Gln Pro Arg Glu Pro Gln Val Tyr Thr Leu Pro
```

```
            115                 120                 125
Pro Ser Gln Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
        195                 200                 205

His Asn His Tyr Thr Gln Lys Ser Leu Ser Leu Ser Leu Gly Lys Gly
    210                 215                 220

Gly Gly Gly Ser Gly Gly Gly Ser Gly Gly Gly Ser His Pro
225                 230                 235                 240

Ile Pro Asp Ser Ser Pro Leu Leu Gln Phe Gly Gly Gln Val Arg Gln
                245                 250                 255

Arg Tyr Leu Tyr Thr Asp Asp Ala Gln Gln Thr Glu Ala His Leu Glu
            260                 265                 270

Ile Arg Glu Asp Gly Thr Val Gly Gly Ala Ala Asp Gln Ser Pro Glu
        275                 280                 285

Ser Leu Leu Gln Leu Lys Ala Leu Lys Pro Gly Val Ile Gln Ile Leu
    290                 295                 300

Gly Val Lys Thr Ser Arg Phe Leu Cys Gln Arg Pro Asp Gly Ala Leu
305                 310                 315                 320

Tyr Gly Ser Leu His Phe Asp Pro Glu Ala Cys Ser Phe Arg Glu Glu
                325                 330                 335

Ile Arg Pro Asp Gly Tyr Asn Val Tyr Gln Ser Glu Ala His Gly Leu
            340                 345                 350

Pro Leu His Leu Pro Gly Asn Lys Ser Pro His Arg Asp Pro Ala Pro
        355                 360                 365

Arg Gly Pro Ala Arg Phe Leu Pro Leu Pro Gly Leu Pro Pro Ala Leu
    370                 375                 380

Pro Glu Pro Pro Gly Ile Leu Ala Pro Gln Pro Pro Asp Val Gly Ser
385                 390                 395                 400

Ser Asp Pro Leu Ser Met Val Thr Gly Leu Glu Ala Val Arg Ser Pro
                405                 410                 415

Ser Tyr Glu Ser
            420

<210> SEQ ID NO 37
<211> LENGTH: 420
<212> TYPE: PRT
<213> ORGANISM: Artificial Sequence
<220> FEATURE:
<223> OTHER INFORMATION: modified FGF21 variant connected to hybrid Fc

<400> SEQUENCE: 37

Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser Gln Glu Asp Pro Glu
        35                  40                  45

Val Gln Phe Asn Trp Tyr Val Asp Gly Val Glu Val His Asn Ala Lys
```

```
            50                  55                  60
Thr Lys Pro Arg Glu Glu Gln Phe Asn Ser Thr Tyr Arg Val Val Ser
 65                  70                  75                  80

Val Leu Thr Val Leu His Gln Asp Trp Leu Asn Gly Lys Glu Tyr Lys
                 85                  90                  95

Cys Lys Val Ser Asn Lys Gly Leu Pro Ser Ser Ile Glu Lys Thr Ile
                100                 105                 110

Ser Lys Ala Lys Gly Gln Pro Arg Glu Pro Gln Val Tyr Thr Leu Pro
                115                 120                 125

Pro Ser Gln Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
                180                 185                 190

Trp Gln Glu Gly Asn Val Phe Ser Cys Ser Val Met His Glu Ala Leu
                195                 200                 205

His Asn His Tyr Thr Gln Lys Ser Leu Ser Leu Ser Leu Gly Lys Gly
210                 215                 220

Gly Gly Gly Ser Gly Gly Gly Ser Gly Gly Gly Gly Ser His Pro
225                 230                 235                 240

Ile Pro Asp Ser Ser Pro Leu Leu Gln Phe Gly Gly Gln Val Arg Gln
                245                 250                 255

Arg Tyr Leu Tyr Thr Asp Asp Ala Gln Gln Thr Glu Ala His Leu Glu
                260                 265                 270

Ile Arg Glu Asp Gly Thr Val Gly Gly Ala Ala Asp Gln Ser Pro Glu
                275                 280                 285

Ser Leu Leu Gln Leu Lys Ala Leu Lys Pro Gly Val Ile Gln Ile Leu
                290                 295                 300

Gly Val Lys Thr Ser Arg Phe Leu Cys Gln Arg Pro Asp Gly Ala Leu
305                 310                 315                 320

Tyr Gly Ser Leu His Phe Asp Pro Glu Ala Cys Ser Phe Arg Glu Glu
                325                 330                 335

Ile Arg Pro Asp Gly Tyr Asn Val Tyr Gln Ser Glu Ala His Gly Leu
                340                 345                 350

Pro Leu His Leu Pro Gly Asn Lys Ser Pro His Arg Asp Pro Ala Pro
                355                 360                 365

Arg Gly Pro Ala Arg Phe Leu Pro Leu Pro Gly Leu Pro Pro Ala Leu
                370                 375                 380

Pro Glu Pro Pro Gly Ile Leu Ala Pro Gln Pro Pro Asp Val Gly Ser
385                 390                 395                 400

Ser Asp Pro Leu Ser Met Val Thr Gly Leu Glu Ala Asn Arg Ser Pro
                405                 410                 415

Ser Tyr Glu Ser
            420

<210> SEQ ID NO 38
<211> LENGTH: 419
<212> TYPE: PRT
<213> ORGANISM: Artificial Sequence
<220> FEATURE:
<223> OTHER INFORMATION: modified FGF21 variant connected to hybrid Fc
```

-continued

<400> SEQUENCE: 38

Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser Gln Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Gln Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
        195                 200                 205

His Asn His Tyr Thr Gln Lys Ser Leu Ser Leu Ser Leu Gly Lys Gly
    210                 215                 220

Gly Gly Gly Ser Gly Gly Gly Ser Gly Gly Gly Ser His Pro
225                 230                 235                 240

Ile Pro Asp Ser Ser Pro Leu Leu Gln Phe Gly Gly Gln Val Arg Gln
                245                 250                 255

Arg Tyr Leu Tyr Thr Asp Asp Ala Gln Gln Thr Glu Ala His Leu Glu
            260                 265                 270

Ile Arg Glu Asp Gly Thr Val Gly Gly Ala Ala Asp Gln Ser Pro Glu
        275                 280                 285

Ser Leu Leu Gln Leu Lys Ala Leu Lys Pro Gly Val Ile Gln Ile Leu
    290                 295                 300

Gly Val Lys Thr Ser Arg Phe Leu Cys Gln Arg Pro Asp Gly Ala Leu
305                 310                 315                 320

Tyr Gly Ser Leu His Phe Asp Pro Glu Ala Cys Ser Phe Arg Glu Glu
                325                 330                 335

Ile Arg Pro Asp Gly Tyr Asn Val Tyr Gln Ser Glu Ala His Gly Leu
            340                 345                 350

Pro Leu His Leu Pro Gly Asn Lys Ser Pro His Arg Asp Pro Ala Pro
        355                 360                 365

Arg Gly Pro Ala Arg Phe Leu Pro Leu Pro Gly Leu Pro Pro Ala Leu
    370                 375                 380

Pro Glu Pro Pro Gly Ile Leu Ala Pro Gln Pro Pro Asp Val Gly Ser
385                 390                 395                 400

Ser Asp Pro Leu Ser Met Val Asn Pro Ser Gln Gly Arg Ser Pro Ser
                405                 410                 415

Tyr Ala Ser

<210> SEQ ID NO 39
<211> LENGTH: 419
<212> TYPE: PRT
<213> ORGANISM: Artificial Sequence
<220> FEATURE:
<223> OTHER INFORMATION: modified FGF21 variant connected to hybrid Fc

<400> SEQUENCE: 39

```
Glu Thr Lys Thr Pro Glu Cys Pro Ser His Thr Gln Pro Leu Gly Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser Gln Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Gln Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
        195                 200                 205

His Asn His Tyr Thr Gln Lys Ser Leu Ser Leu Ser Leu Gly Lys Gly
    210                 215                 220

Gly Gly Gly Ser Gly Gly Gly Ser Gly Gly Gly Ser His Pro
225                 230                 235                 240

Ile Pro Asp Ser Ser Pro Leu Leu Gln Phe Gly Gly Gln Val Arg Gln
                245                 250                 255

Arg Tyr Leu Tyr Thr Asp Asp Ala Gln Gln Thr Glu Ala His Leu Glu
            260                 265                 270

Ile Arg Glu Asp Gly Thr Val Gly Gly Ala Ala Asp Gln Ser Pro Glu
        275                 280                 285

Ser Leu Leu Gln Leu Lys Ala Leu Lys Pro Gly Val Ile Gln Ile Leu
    290                 295                 300

Gly Val Lys Thr Ser Arg Phe Leu Cys Gln Arg Pro Asp Gly Ala Leu
305                 310                 315                 320

Tyr Gly Ser Leu His Phe Asp Pro Glu Ala Cys Ser Phe Arg Glu Glu
                325                 330                 335

Ile Arg Pro Asp Gly Tyr Asn Val Tyr Gln Ser Glu Ala His Gly Leu
            340                 345                 350
```

-continued

```
Pro Leu His Leu Pro Gly Asn Lys Ser Pro His Arg Asp Pro Ala Pro
            355                 360                 365

Arg Gly Pro Ala Arg Phe Leu Pro Leu Pro Gly Leu Pro Pro Ala Leu
370                 375                 380

Pro Glu Pro Pro Gly Ile Leu Ala Pro Gln Pro Pro Asp Val Gly Ser
385                 390                 395                 400

Ser Asp Pro Leu Ser Met Val Asn Pro Ser Gln Gly Arg Ser Pro Ser
                405                 410                 415

Tyr Glu Ser

<210> SEQ ID NO 40
<211> LENGTH: 423
<212> TYPE: PRT
<213> ORGANISM: Artificial Sequence
<220> FEATURE:
<223> OTHER INFORMATION: REG(Amgen)

<400> SEQUENCE: 40

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys Gly Gly Gly Ser Gly Gly Gly Gly Ser Gly Gly Gly Gly
225                 230                 235                 240

Gly Ser His Pro Ile Pro Asp Ser Ser Pro Leu Leu Gln Phe Gly Gly
                245                 250                 255

Gln Val Arg Gln Arg Tyr Leu Tyr Thr Asp Asp Ala Gln Gln Thr Glu
            260                 265                 270

Ala His Leu Glu Ile Arg Glu Asp Gly Thr Val Gly Gly Ala Ala Asp
        275                 280                 285

Gln Ser Pro Glu Ser Leu Leu Gln Leu Lys Ala Leu Lys Pro Gly Val
```

```
                    290                 295                 300

Ile Gln Ile Leu Gly Val Lys Thr Ser Arg Phe Leu Cys Gln Arg Pro
305                 310                 315                 320

Asp Gly Ala Leu Tyr Gly Ser Leu His Phe Asp Pro Glu Ala Cys Ser
                325                 330                 335

Phe Arg Glu Arg Leu Leu Glu Asp Gly Tyr Asn Val Tyr Gln Ser Glu
                340                 345                 350

Ala His Gly Leu Pro Leu His Leu Pro Gly Asn Lys Ser Pro His Arg
                355                 360                 365

Asp Pro Ala Pro Arg Gly Pro Ala Arg Phe Leu Pro Leu Pro Gly Leu
                370                 375                 380

Pro Pro Ala Leu Pro Glu Pro Pro Gly Ile Leu Ala Pro Gln Pro Pro
385                 390                 395                 400

Asp Val Gly Ser Ser Asp Pro Leu Ser Met Val Gly Gly Ser Gln Gly
                405                 410                 415

Arg Ser Pro Ser Tyr Glu Ser
                420

<210> SEQ ID NO 41
<211> LENGTH: 424
<212> TYPE: PRT
<213> ORGANISM: Artificial Sequence
<220> FEATURE:
<223> OTHER INFORMATION: FGF21 connected to Fc(lilly)

<400> SEQUENCE: 41

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
                35                  40                  45

Ser Gln Glu Asp Pro Glu Val Gln Phe Asn Trp Tyr Val Asp Gly Val
            50                  55                  60

Glu Val His Asn Ala Lys Thr Lys Pro Arg Glu Glu Gln Phe Asn Ser
65              70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
                115                 120                 125

Gln Val Tyr Thr Leu Pro Pro Ser Gln Glu Glu Met Thr Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
                210                 215                 220

Leu Ser Leu Gly Gly Gly Gly Gly Ser Gly Gly Gly Gly Ser Gly Gly
```

```
                225                 230                 235                 240
Gly Gly Ser Ala His Pro Ile Pro Asp Ser Ser Pro Leu Leu Gln Phe
                245                 250                 255
Gly Gly Gln Val Arg Gln Arg Tyr Leu Tyr Thr Asp Ala Gln Gln
                260                 265                 270
Thr Glu Cys His Leu Glu Ile Arg Glu Asp Gly Thr Val Gly Cys Ala
                275                 280                 285
Ala Asp Gln Ser Pro Glu Ser Leu Leu Gln Leu Lys Ala Leu Lys Pro
                290                 295                 300
Gly Val Ile Gln Ile Leu Gly Val Lys Thr Ser Arg Phe Leu Cys Gln
305                 310                 315                 320
Arg Pro Asp Gly Ala Leu Tyr Gly Ser Leu His Phe Asp Pro Glu Ala
                325                 330                 335
Cys Ser Phe Arg Glu Asp Leu Lys Glu Asp Gly Tyr Asn Val Tyr Gln
                340                 345                 350
Ser Glu Ala His Gly Leu Pro Leu His Leu Pro Gly Asp Lys Ser Pro
                355                 360                 365
His Arg Lys Pro Ala Pro Arg Gly Pro Ala Arg Phe Leu Pro Leu Pro
370                 375                 380
Gly Leu Pro Pro Ala Leu Pro Glu Pro Pro Gly Ile Leu Ala Pro Gln
385                 390                 395                 400
Pro Pro Asp Val Gly Ser Ser Asp Pro Leu Arg Leu Val Glu Pro Ser
                405                 410                 415
Gln Leu Arg Ser Pro Ser Phe Glu
                420

<210> SEQ ID NO 42
<211> LENGTH: 31
<212> TYPE: PRT
<213> ORGANISM: Artificial Sequence
<220> FEATURE:
<223> OTHER INFORMATION: GLP-1

<400> SEQUENCE: 42

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
                20                  25                  30

<210> SEQ ID NO 43
<211> LENGTH: 31
<212> TYPE: PRT
<213> ORGANISM: Artificial Sequence
<220> FEATURE:
<223> OTHER INFORMATION: GLP-1 variant

<400> SEQUENCE: 43

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
                20                  25                  30

<210> SEQ ID NO 44
<211> LENGTH: 31
<212> TYPE: PRT
<213> ORGANISM: Artificial Sequence
<220> FEATURE:
<223> OTHER INFORMATION: GLP-1 variant

<400> SEQUENCE: 44
```

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly
            20                  25                  30

<210> SEQ ID NO 45
<211> LENGTH: 31
<212> TYPE: PRT
<213> ORGANISM: Artificial Sequence
<220> FEATURE:
<223> OTHER INFORMATION: GLP-1 variant

<400> SEQUENCE: 45

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly
            20                  25                  30

<210> SEQ ID NO 46
<211> LENGTH: 31
<212> TYPE: PRT
<213> ORGANISM: Artificial Sequence
<220> FEATURE:
<223> OTHER INFORMATION: GLP-1 variant

<400> SEQUENCE: 46

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30

<210> SEQ ID NO 47
<211> LENGTH: 245
<212> TYPE: PRT
<213> ORGANISM: Artificial Sequence
<220> FEATURE:
<223> OTHER INFORMATION: hybrid Fc5

<400> SEQUENCE: 47

Arg Asn Thr Gly Arg Gly Gly Glu Glu Lys Lys Lys Glu Lys Glu Lys
1               5                   10                  15

Glu Glu Gln Glu Glu Arg Glu Thr Lys Thr Pro Glu Cys Pro Ser His
            20                  25                  30

Thr Gln Pro Leu Gly Val Phe Leu Phe Pro Pro Lys Pro Lys Asp Thr
        35                  40                  45

Leu Met Ile Ser Arg Thr Pro Glu Val Thr Cys Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
        115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
            165                 170                 175

Val Glu Trp Glu Ser Asn Gly Gln Pro Glu Asn Asn Tyr Lys Thr Thr
        180                 185                 190

Pro Pro Val Leu Asp Ser Asp Gly Ser Phe Phe Leu Tyr Ser Arg Leu
            195                 200                 205

Thr Val Asp Lys Ser Arg Trp Gln Glu Gly Asn Val Phe Ser Cys Ser
        210                 215                 220

Val Met His Glu Ala Leu His Asn His Tyr Thr Gln Lys Ser Leu Ser
225                 230                 235                 240

Leu Ser Leu Gly Lys
            245

<210> SEQ ID NO 48
<211> LENGTH: 233
<212> TYPE: PRT
<213> ORGANISM: Artificial Sequence
<220> FEATURE:
<223> OTHER INFORMATION: hybrid Fc40

<400> SEQUENCE: 48

Glu Lys Glu Lys Glu Glu Gln Glu Glu Arg Glu Thr Lys Thr Pro Glu
1               5                   10                  15

Cys Pro Ser His Thr Gln Pro Leu Gly Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser Gln Glu Asp Pro Glu Val Gln Phe Asn Trp Tyr
    50                  55                  60

Val Asp Gly Val Glu Val His Asn Ala Lys Thr Lys Pro Arg Glu Glu
65                  70                  75                  80

Gln Phe Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Gly Leu Pro Ser Ser Ile Glu Lys Thr Ile Ser Lys Ala Lys Gly Gln
        115                 120                 125

Pro Arg Glu Pro Gln Val Tyr Thr Leu Pro Pro Ser Gln Glu Glu Met
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Arg Leu Thr Val Asp Lys Ser Arg Trp Gln Glu Gly Asn Val
        195                 200                 205

Phe Ser Cys Ser Val Met His Glu Ala Leu His Asn His Tyr Thr Gln
    210                 215                 220

Lys Ser Leu Ser Leu Ser Leu Gly Lys
225                 230

<210> SEQ ID NO 49
<211> LENGTH: 276
<212> TYPE: PRT
<213> ORGANISM: Artificial Sequence
<220> FEATURE:

-continued

<223> OTHER INFORMATION: GLP-1 variant connected to hybrid Fc5

<400> SEQUENCE: 49

```
His Gly Glu Gly Thr Phe Thr Ser Asp Val Ser Ser Tyr Leu Glu Gly
 1               5                  10                  15
Gln Ala Ala Lys Glu Phe Ile Ala Trp Leu Val Lys Gly Arg Gly Arg
            20                  25                  30
Asn Thr Gly Arg Gly Gly Glu Glu Lys Lys Lys Glu Lys Glu Lys Glu
        35                  40                  45
Glu Gln Glu Glu Arg Glu Thr Lys Thr Pro Glu Cys Pro Ser His Thr
    50                  55                  60
Gln Pro Leu Gly Val Phe Leu Phe Pro Pro Lys Pro Lys Asp Thr Leu
65                  70                  75                  80
Met Ile Ser Arg Thr Pro Glu Val Thr Cys Val Val Val Asp Val Ser
                85                  90                  95
Gln Glu Asp Pro Glu Val Gln Phe Asn Trp Tyr Val Asp Gly Val Glu
            100                 105                 110
Val His Asn Ala Lys Thr Lys Pro Arg Glu Glu Gln Phe Asn Ser Thr
        115                 120                 125
Tyr Arg Val Val Ser Val Leu Thr Val Leu His Gln Asp Trp Leu Asn
    130                 135                 140
Gly Lys Glu Tyr Lys Cys Lys Val Ser Asn Lys Gly Leu Pro Ser Ser
145                 150                 155                 160
Ile Glu Lys Thr Ile Ser Lys Ala Lys Gly Gln Pro Arg Glu Pro Gln
                165                 170                 175
Val Tyr Thr Leu Pro Pro Ser Gln Glu Met Thr Lys Asn Gln Val
            180                 185                 190
Ser Leu Thr Cys Leu Val Lys Gly Phe Tyr Pro Ser Asp Ile Ala Val
    195                 200                 205
Glu Trp Glu Ser Asn Gly Gln Pro Glu Asn Asn Tyr Lys Thr Thr Pro
    210                 215                 220
Pro Val Leu Asp Ser Asp Gly Ser Phe Phe Leu Tyr Ser Arg Leu Thr
225                 230                 235                 240
Val Asp Lys Ser Arg Trp Gln Glu Gly Asn Val Phe Ser Cys Ser Val
                245                 250                 255
Met His Glu Ala Leu His Asn His Tyr Thr Gln Lys Ser Leu Ser Leu
            260                 265                 270
Ser Leu Gly Lys
        275
```

<210> SEQ ID NO 50
<211> LENGTH: 264
<212> TYPE: PRT
<213> ORGANISM: Artificial Sequence
<220> FEATURE:
<223> OTHER INFORMATION: GLP-1 variant connected to hybrid Fc40

<400> SEQUENCE: 50

```
His Gly Glu Gly Thr Phe Thr Ser Asp Val Ser Ser Tyr Leu Glu Gly
 1               5                  10                  15
Gln Ala Ala Lys Glu Phe Ile Ala Trp Leu Val Lys Gly Arg Gly Glu
            20                  25                  30
Lys Glu Lys Glu Glu Gln Glu Glu Arg Glu Thr Lys Thr Pro Glu Cys
        35                  40                  45
Pro Ser His Thr Gln Pro Leu Gly Val Phe Leu Phe Pro Pro Lys Pro
    50                  55                  60
```

-continued

```
Lys Asp Thr Leu Met Ile Ser Arg Thr Pro Glu Val Thr Cys Val Val
 65                  70                  75                  80

Val Asp Val Ser Gln Glu Asp Pro Glu Val Gln Phe Asn Trp Tyr Val
                 85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Gly
130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Leu Gly Lys
            260

<210> SEQ ID NO 51
<211> LENGTH: 276
<212> TYPE: PRT
<213> ORGANISM: Artificial Sequence
<220> FEATURE:
<223> OTHER INFORMATION: GLP-1 variant connected to hybrid Fc5

<400> SEQUENCE: 51

His Gly Glu Gly Thr Phe Thr Ser Asp Val Ser Ser Tyr Leu Glu Glu
 1                   5                  10                  15

Gln Ala Ala Lys Glu Phe Ile Ala Trp Leu Val Lys Gly Arg Gly Arg
                 20                  25                  30

Asn Thr Gly Arg Gly Gly Glu Glu Lys Lys Lys Glu Lys Glu Lys Glu
            35                  40                  45

Glu Gln Glu Glu Arg Glu Thr Lys Thr Pro Glu Cys Pro Ser His Thr
 50                  55                  60

Gln Pro Leu Gly Val Phe Leu Phe Pro Pro Lys Pro Lys Asp Thr Leu
 65                  70                  75                  80

Met Ile Ser Arg Thr Pro Glu Val Thr Cys Val Val Val Asp Val Ser
                 85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160
```

```
Ile Glu Lys Thr Ile Ser Lys Ala Lys Gly Gln Pro Arg Glu Pro Gln
            165                 170                 175

Val Tyr Thr Leu Pro Pro Ser Gln Glu Met Thr Lys Asn Gln Val
        180                 185                 190

Ser Leu Thr Cys Leu Val Lys Gly Phe Tyr Pro Ser Asp Ile Ala Val
            195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Lys
        275

<210> SEQ ID NO 52
<211> LENGTH: 264
<212> TYPE: PRT
<213> ORGANISM: Artificial Sequence
<220> FEATURE:
<223> OTHER INFORMATION: GLP-1 variant connected to hybrid Fc40

<400> SEQUENCE: 52

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Glu
            20                  25                  30

Lys Glu Lys Glu Glu Gln Glu Arg Glu Thr Lys Thr Pro Glu Cys
        35                  40                  45

Pro Ser His Thr Gln Pro Leu Gly Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Gly
    130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Arg Leu Thr Val Asp Lys Ser Arg Trp Gln Glu Gly Asn Val Phe
225                 230                 235                 240
```

```
Ser Cys Ser Val Met His Glu Ala Leu His Asn His Tyr Thr Gln Lys
            245                 250                 255

Ser Leu Ser Leu Ser Leu Gly Lys
            260
```

<210> SEQ ID NO 53
<211> LENGTH: 276
<212> TYPE: PRT
<213> ORGANISM: Artificial Sequence
<220> FEATURE:
<223> OTHER INFORMATION: GLP-1 variant connected to hybrid Fc5

<400> SEQUENCE: 53

```
His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Arg
            20                  25                  30

Asn Thr Gly Arg Gly Gly Glu Glu Lys Lys Lys Glu Lys Glu Lys Glu
        35                  40                  45

Glu Gln Glu Glu Arg Glu Thr Lys Thr Pro Glu Cys Pro Ser His Thr
    50                  55                  60

Gln Pro Leu Gly Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Lys
        275
```

<210> SEQ ID NO 54
<211> LENGTH: 264
<212> TYPE: PRT
<213> ORGANISM: Artificial Sequence
<220> FEATURE:
<223> OTHER INFORMATION: GLP-1 variant connected to hybrid Fc40

<400> SEQUENCE: 54

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Glu
            20                  25                  30

Lys Glu Lys Glu Glu Gln Glu Arg Glu Thr Lys Thr Pro Glu Cys
        35                  40                  45

Pro Ser His Thr Gln Pro Leu Gly Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
            115                 120                 125

Asp Trp Leu Asn Gly Lys Glu Tyr Lys Cys Lys Val Ser Asn Lys Gly
    130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Leu Gly Lys
            260

<210> SEQ ID NO 55
<211> LENGTH: 276
<212> TYPE: PRT
<213> ORGANISM: Artificial Sequence
<220> FEATURE:
<223> OTHER INFORMATION: GLP-1 variant connected to hybrid Fc5

<400> SEQUENCE: 55

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Arg
            20                  25                  30

Asn Thr Gly Arg Gly Gly Glu Glu Lys Lys Glu Lys Glu Lys Glu
        35                  40                  45

Glu Gln Glu Glu Arg Glu Thr Lys Thr Pro Glu Cys Pro Ser His Thr
    50                  55                  60

Gln Pro Leu Gly Val Phe Leu Phe Pro Pro Lys Pro Lys Asp Thr Leu
65                  70                  75                  80

Met Ile Ser Arg Thr Pro Glu Val Thr Cys Val Val Val Asp Val Ser

```
                85                  90                  95
Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
            115                 120                 125

Tyr Arg Val Val Ser Val Leu Thr Val Leu His Gln Asp Trp Leu Asn
            130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
            165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
            195                 200                 205

Glu Trp Glu Ser Asn Gly Gln Pro Glu Asn Asn Tyr Lys Thr Thr Pro
            210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
            245                 250                 255

Met His Glu Ala Leu His Asn His Tyr Thr Gln Lys Ser Leu Ser Leu
            260                 265                 270

Ser Leu Gly Lys
        275

<210> SEQ ID NO 56
<211> LENGTH: 264
<212> TYPE: PRT
<213> ORGANISM: Artificial Sequence
<220> FEATURE:
<223> OTHER INFORMATION: GLP-1 variant connected to hybrid Fc40

<400> SEQUENCE: 56

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Glu
            20                  25                  30

Lys Glu Lys Glu Glu Gln Glu Glu Arg Glu Thr Lys Thr Pro Glu Cys
            35                  40                  45

Pro Ser His Thr Gln Pro Leu Gly Val Phe Leu Phe Pro Pro Lys Pro
        50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
            85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
            115                 120                 125

Asp Trp Leu Asn Gly Lys Glu Tyr Lys Cys Lys Val Ser Asn Lys Gly
            130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
```

|     |     |     |     | 165 |     |     |     | 170 |     |     |     | 175 |     |     |
| --- | --- | --- | --- | --- | --- | --- | --- | --- | --- | --- | --- | --- | --- | --- |

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
            195                 200                 205

Lys Thr Thr Pro Pro Val Leu Asp Ser Asp Gly Ser Phe Phe Leu Tyr
            210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
            245                 250                 255

Ser Leu Ser Leu Ser Leu Gly Lys
            260

<210> SEQ ID NO 57
<211> LENGTH: 275
<212> TYPE: PRT
<213> ORGANISM: Artificial Sequence
<220> FEATURE:
<223> OTHER INFORMATION: Dulaglutide

<400> SEQUENCE: 57

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Gly Ser Ala Glu
            35                  40                  45

Ser Lys Tyr Gly Pro Pro Cys Pro Pro Cys Pro Ala Pro Glu Ala Ala
50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
            85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
            115                 120                 125

Tyr Arg Val Val Ser Val Leu Thr Val Leu His Gln Asp Trp Leu Asn
            130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
            165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
            195                 200                 205

Glu Trp Glu Ser Asn Gly Gln Pro Glu Asn Asn Tyr Lys Thr Thr Pro
            210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
            245                 250                 255

Met His Glu Ala Leu His Asn His Tyr Thr Gln Lys Ser Leu Ser Leu

Ser Leu Gly
   275

<210> SEQ ID NO 58
<211> LENGTH: 461
<212> TYPE: PRT
<213> ORGANISM: Artificial Sequence
<220> FEATURE:
<223> OTHER INFORMATION: GLP1(A2G)-HyFc40-GS3-FGF21(EIRP, TGLEAV)

<400> SEQUENCE: 58

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Glu
            20                  25                  30

Lys Glu Lys Glu Glu Gln Glu Glu Arg Glu Thr Lys Thr Pro Glu Cys
        35                  40                  45

Pro Ser His Thr Gln Pro Leu Gly Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Gly
    130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Leu Gly Lys Gly Gly Gly Gly Ser Gly Gly Gly
            260                 265                 270

Gly Ser Gly Gly Gly Ser His Pro Ile Pro Asp Ser Ser Pro Leu
        275                 280                 285

Leu Gln Phe Gly Gly Gln Val Arg Gln Arg Tyr Leu Tyr Thr Asp Asp
    290                 295                 300

Ala Gln Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335

Leu Lys Pro Gly Val Ile Gln Ile Leu Gly Val Lys Thr Ser Arg Phe

```
                340                 345                 350
Leu Cys Gln Arg Pro Asp Gly Ala Leu Tyr Gly Ser Leu His Phe Asp
            355                 360                 365

Pro Glu Ala Cys Ser Phe Arg Glu Glu Ile Arg Pro Asp Gly Tyr Asn
        370                 375                 380

Val Tyr Gln Ser Glu Ala His Gly Leu Pro Leu His Leu Pro Gly Asn
385                 390                 395                 400

Lys Ser Pro His Arg Asp Pro Ala Pro Arg Gly Pro Ala Arg Phe Leu
                405                 410                 415

Pro Leu Pro Gly Leu Pro Pro Ala Leu Pro Glu Pro Pro Gly Ile Leu
            420                 425                 430

Ala Pro Gln Pro Pro Asp Val Gly Ser Ser Asp Pro Leu Ser Met Val
        435                 440                 445

Thr Gly Leu Glu Ala Val Arg Ser Pro Ser Tyr Ala Ser
450                 455                 460

<210> SEQ ID NO 59
<211> LENGTH: 473
<212> TYPE: PRT
<213> ORGANISM: Artificial Sequence
<220> FEATURE:
<223> OTHER INFORMATION: GLP1(GE)-HyFc5-GS3-FGF21(EIRP, TGLEAV)

<400> SEQUENCE: 59

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Arg
            20                  25                  30

Asn Thr Gly Arg Gly Gly Glu Glu Lys Lys Lys Glu Lys Glu Lys Glu
        35                  40                  45

Glu Gln Glu Glu Arg Glu Thr Lys Thr Pro Glu Cys Pro Ser His Thr
    50                  55                  60

Gln Pro Leu Gly Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
```

```
                    245                 250                 255
Met His Glu Ala Leu His Asn His Tyr Thr Gln Lys Ser Leu Ser Leu
                260                 265                 270

Ser Leu Gly Lys Gly Gly Gly Ser Gly Gly Gly Ser Gly Gly
            275                 280                 285

Gly Gly Ser His Pro Ile Pro Asp Ser Ser Pro Leu Leu Gln Phe Gly
            290                 295                 300

Gly Gln Val Arg Gln Arg Tyr Leu Tyr Thr Asp Asp Ala Gln Gln Thr
305                 310                 315                 320

Glu Ala His Leu Glu Ile Arg Glu Asp Gly Thr Val Gly Gly Ala Ala
                325                 330                 335

Asp Gln Ser Pro Glu Ser Leu Leu Gln Leu Lys Ala Leu Lys Pro Gly
                340                 345                 350

Val Ile Gln Ile Leu Gly Val Lys Thr Ser Arg Phe Leu Cys Gln Arg
                355                 360                 365

Pro Asp Gly Ala Leu Tyr Gly Ser Leu His Phe Asp Pro Glu Ala Cys
            370                 375                 380

Ser Phe Arg Glu Glu Ile Arg Pro Asp Gly Tyr Asn Val Tyr Gln Ser
385                 390                 395                 400

Glu Ala His Gly Leu Pro Leu His Leu Pro Gly Asn Lys Ser Pro His
                405                 410                 415

Arg Asp Pro Ala Pro Arg Gly Pro Ala Arg Phe Leu Pro Leu Pro Gly
            420                 425                 430

Leu Pro Pro Ala Leu Pro Glu Pro Pro Gly Ile Leu Ala Pro Gln Pro
            435                 440                 445

Pro Asp Val Gly Ser Ser Asp Pro Leu Ser Met Val Thr Gly Leu Glu
        450                 455                 460

Ala Val Arg Ser Pro Ser Tyr Ala Ser
465                 470

<210> SEQ ID NO 60
<211> LENGTH: 461
<212> TYPE: PRT
<213> ORGANISM: Artificial Sequence
<220> FEATURE:
<223> OTHER INFORMATION: GLP1(GE)-HyFc40-GS3-FGF21(EIRP, TGLEAV)

<400> SEQUENCE: 60

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Glu
            20                  25                  30

Lys Glu Lys Glu Glu Gln Glu Glu Arg Glu Thr Lys Thr Pro Glu Cys
        35                  40                  45

Pro Ser His Thr Gln Pro Leu Gly Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Gly
```

```
            130                 135                 140
Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Leu Gly Lys Gly Gly Gly Gly Ser Gly Gly Gly
            260                 265                 270

Gly Ser Gly Gly Gly Gly Ser His Pro Ile Pro Asp Ser Ser Pro Leu
        275                 280                 285

Leu Gln Phe Gly Gly Gln Val Arg Gln Arg Tyr Leu Tyr Thr Asp Asp
290                 295                 300

Ala Gln Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335

Leu Lys Pro Gly Val Ile Gln Ile Leu Gly Val Lys Thr Ser Arg Phe
            340                 345                 350

Leu Cys Gln Arg Pro Asp Gly Ala Leu Tyr Gly Ser Leu His Phe Asp
        355                 360                 365

Pro Glu Ala Cys Ser Phe Arg Glu Glu Ile Arg Pro Asp Gly Tyr Asn
370                 375                 380

Val Tyr Gln Ser Glu Ala His Gly Leu Pro Leu His Leu Pro Gly Asn
385                 390                 395                 400

Lys Ser Pro His Arg Asp Pro Ala Pro Arg Gly Pro Ala Arg Phe Leu
                405                 410                 415

Pro Leu Pro Gly Leu Pro Pro Ala Leu Pro Glu Pro Pro Gly Ile Leu
            420                 425                 430

Ala Pro Gln Pro Pro Asp Val Gly Ser Ser Asp Pro Leu Ser Met Val
        435                 440                 445

Thr Gly Leu Glu Ala Val Arg Ser Pro Ser Tyr Ala Ser
450                 455                 460

<210> SEQ ID NO 61
<211> LENGTH: 473
<212> TYPE: PRT
<213> ORGANISM: Artificial Sequence
<220> FEATURE:
<223> OTHER INFORMATION: GLP1(GG)-HyFc5-GS3-FGF21(EIRP, TGLEAV)

<400> SEQUENCE: 61

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Arg
            20                  25                  30

Asn Thr Gly Arg Gly Gly Glu Glu Lys Lys Lys Glu Lys Glu Lys Glu
```

```
                35                  40                  45
Glu Gln Glu Glu Arg Glu Thr Lys Thr Pro Glu Cys Pro Ser His Thr
 50                  55                  60

Gln Pro Leu Gly Val Phe Leu Phe Pro Pro Lys Pro Lys Asp Thr Leu
 65                  70                  75                  80

Met Ile Ser Arg Thr Pro Glu Val Thr Cys Val Val Val Asp Val Ser
                 85                  90                  95

Gln Glu Asp Pro Glu Val Gln Phe Asn Trp Tyr Val Asp Gly Val Glu
                100                 105                 110

Val His Asn Ala Lys Thr Lys Pro Arg Glu Glu Gln Phe Asn Ser Thr
            115                 120                 125

Tyr Arg Val Val Ser Val Leu Thr Val Leu His Gln Asp Trp Leu Asn
        130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Lys Gly Gly Gly Ser Gly Gly Gly Ser Gly Gly Gly
        275                 280                 285

Gly Gly Ser His Pro Ile Pro Asp Ser Ser Pro Leu Leu Gln Phe Gly
    290                 295                 300

Gly Gln Val Arg Gln Arg Tyr Leu Tyr Thr Asp Asp Ala Gln Gln Thr
305                 310                 315                 320

Glu Ala His Leu Glu Ile Arg Glu Asp Gly Thr Val Gly Gly Ala Ala
                325                 330                 335

Asp Gln Ser Pro Glu Ser Leu Leu Gln Leu Lys Ala Leu Lys Pro Gly
            340                 345                 350

Val Ile Gln Ile Leu Gly Val Lys Thr Ser Arg Phe Leu Cys Gln Arg
        355                 360                 365

Pro Asp Gly Ala Leu Tyr Gly Ser Leu His Phe Asp Pro Glu Ala Cys
    370                 375                 380

Ser Phe Arg Glu Glu Ile Arg Pro Asp Gly Tyr Asn Val Tyr Gln Ser
385                 390                 395                 400

Glu Ala His Gly Leu Pro Leu His Leu Pro Gly Asn Lys Ser Pro His
                405                 410                 415

Arg Asp Pro Ala Pro Arg Gly Pro Ala Arg Phe Leu Pro Leu Pro Gly
            420                 425                 430

Leu Pro Pro Ala Leu Pro Glu Pro Pro Gly Ile Leu Ala Pro Gln Pro
        435                 440                 445

Pro Asp Val Gly Ser Ser Asp Pro Leu Ser Met Val Thr Gly Leu Glu
    450                 455                 460
```

Ala Val Arg Ser Pro Ser Tyr Ala Ser
465                 470

<210> SEQ ID NO 62
<211> LENGTH: 461
<212> TYPE: PRT
<213> ORGANISM: Artificial Sequence
<220> FEATURE:
<223> OTHER INFORMATION: GLP1(GG)-HyFc40-GS3-FGF21(EIRP, TGLEAV)

<400> SEQUENCE: 62

```
His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Glu
            20                  25                  30

Lys Glu Lys Glu Glu Gln Glu Glu Arg Glu Thr Lys Thr Pro Glu Cys
        35                  40                  45

Pro Ser His Thr Gln Pro Leu Gly Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Gly
    130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Leu Gly Lys Gly Gly Gly Gly Ser Gly Gly Gly
            260                 265                 270

Gly Ser Gly Gly Gly Gly Ser His Pro Ile Pro Asp Ser Ser Pro Leu
        275                 280                 285

Leu Gln Phe Gly Gly Gln Val Arg Gln Arg Tyr Leu Tyr Thr Asp Asp
    290                 295                 300

Ala Gln Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335

Leu Lys Pro Gly Val Ile Gln Ile Leu Gly Val Lys Thr Ser Arg Phe
            340                 345                 350
```

-continued

```
Leu Cys Gln Arg Pro Asp Gly Ala Leu Tyr Gly Ser Leu His Phe Asp
            355                 360                 365

Pro Glu Ala Cys Ser Phe Arg Glu Glu Ile Arg Pro Asp Gly Tyr Asn
        370                 375                 380

Val Tyr Gln Ser Glu Ala His Gly Leu Pro Leu His Leu Pro Gly Asn
385                 390                 395                 400

Lys Ser Pro His Arg Asp Pro Ala Pro Arg Gly Pro Ala Arg Phe Leu
                405                 410                 415

Pro Leu Pro Gly Leu Pro Pro Ala Leu Pro Glu Pro Pro Gly Ile Leu
            420                 425                 430

Ala Pro Gln Pro Pro Asp Val Gly Ser Ser Asp Pro Leu Ser Met Val
        435                 440                 445

Thr Gly Leu Glu Ala Val Arg Ser Pro Ser Tyr Ala Ser
    450                 455                 460

<210> SEQ ID NO 63
<211> LENGTH: 473
<212> TYPE: PRT
<213> ORGANISM: Artificial Sequence
<220> FEATURE:
<223> OTHER INFORMATION: GLP1(GEG)-HyFc5-GS3-FGF21(EIRP, TGLEAV)

<400> SEQUENCE: 63

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Arg
            20                  25                  30

Asn Thr Gly Arg Gly Gly Glu Glu Lys Lys Lys Glu Lys Glu Lys Glu
        35                  40                  45

Glu Gln Glu Glu Arg Glu Thr Lys Thr Pro Glu Cys Pro Ser His Thr
    50                  55                  60

Gln Pro Leu Gly Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255
```

Met His Glu Ala Leu His Asn His Tyr Thr Gln Lys Ser Leu Ser Leu
            260                 265                 270

Ser Leu Gly Lys Gly Gly Gly Ser Gly Gly Gly Ser Gly Gly
        275                 280                 285

Gly Gly Ser His Pro Ile Pro Asp Ser Ser Pro Leu Leu Gln Phe Gly
        290                 295                 300

Gly Gln Val Arg Gln Arg Tyr Leu Tyr Thr Asp Asp Ala Gln Thr
305                 310                 315                 320

Glu Ala His Leu Glu Ile Arg Glu Asp Gly Thr Val Gly Gly Ala Ala
                325                 330                 335

Asp Gln Ser Pro Glu Ser Leu Leu Gln Leu Lys Ala Leu Lys Pro Gly
            340                 345                 350

Val Ile Gln Ile Leu Gly Val Lys Thr Ser Arg Phe Leu Cys Gln Arg
            355                 360                 365

Pro Asp Gly Ala Leu Tyr Gly Ser Leu His Phe Asp Pro Glu Ala Cys
        370                 375                 380

Ser Phe Arg Glu Glu Ile Arg Pro Asp Gly Tyr Asn Val Tyr Gln Ser
385                 390                 395                 400

Glu Ala His Gly Leu Pro Leu His Leu Pro Gly Asn Lys Ser Pro His
                405                 410                 415

Arg Asp Pro Ala Pro Arg Gly Pro Ala Arg Phe Leu Pro Leu Pro Gly
            420                 425                 430

Leu Pro Pro Ala Leu Pro Glu Pro Pro Gly Ile Leu Ala Pro Gln Pro
            435                 440                 445

Pro Asp Val Gly Ser Ser Asp Pro Leu Ser Met Val Thr Gly Leu Glu
        450                 455                 460

Ala Val Arg Ser Pro Ser Tyr Ala Ser
465                 470

<210> SEQ ID NO 64
<211> LENGTH: 461
<212> TYPE: PRT
<213> ORGANISM: Artificial Sequence
<220> FEATURE:
<223> OTHER INFORMATION: GLP1(GEG)-HyFc40-GS3-FGF21(EIRP, TGLEAV)

<400> SEQUENCE: 64

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Glu
            20                  25                  30

Lys Glu Lys Glu Glu Gln Glu Glu Arg Glu Thr Lys Thr Pro Glu Cys
        35                  40                  45

Pro Ser His Thr Gln Pro Leu Gly Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Gly
    130                 135                 140

```
Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Leu Gly Lys Gly Gly Gly Gly Ser Gly Gly Gly
            260                 265                 270

Gly Ser Gly Gly Gly Gly Ser His Pro Ile Pro Asp Ser Ser Pro Leu
        275                 280                 285

Leu Gln Phe Gly Gly Gln Val Arg Gln Arg Tyr Leu Tyr Thr Asp Asp
290                 295                 300

Ala Gln Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335

Leu Lys Pro Gly Val Ile Gln Ile Leu Gly Val Lys Thr Ser Arg Phe
            340                 345                 350

Leu Cys Gln Arg Pro Asp Gly Ala Leu Tyr Gly Ser Leu His Phe Asp
        355                 360                 365

Pro Glu Ala Cys Ser Phe Arg Glu Glu Ile Arg Pro Asp Gly Tyr Asn
370                 375                 380

Val Tyr Gln Ser Glu Ala His Gly Leu Pro Leu His Leu Pro Gly Asn
385                 390                 395                 400

Lys Ser Pro His Arg Asp Pro Ala Pro Arg Gly Pro Ala Arg Phe Leu
                405                 410                 415

Pro Leu Pro Gly Leu Pro Pro Ala Leu Pro Glu Pro Pro Gly Ile Leu
            420                 425                 430

Ala Pro Gln Pro Pro Asp Val Gly Ser Ser Asp Pro Leu Ser Met Val
        435                 440                 445

Thr Gly Leu Glu Ala Val Arg Ser Pro Ser Tyr Ala Ser
    450                 455                 460

<210> SEQ ID NO 65
<211> LENGTH: 461
<212> TYPE: PRT
<213> ORGANISM: Artificial Sequence
<220> FEATURE:
<223> OTHER INFORMATION: GLP1(GEG)-HyFc40-GS3-FGF21(EIRP, TGLEAV, A180E)

<400> SEQUENCE: 65

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Glu
            20                  25                  30

Lys Glu Lys Glu Glu Gln Glu Glu Arg Glu Thr Lys Thr Pro Glu Cys
        35                  40                  45
```

-continued

Pro Ser His Thr Gln Pro Leu Gly Val Phe Leu Pro Pro Lys Pro
        50                  55                  60

Lys Asp Thr Leu Met Ile Ser Arg Thr Pro Glu Val Thr Cys Val Val
 65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Gly
    130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Arg Leu Thr Val Asp Lys Ser Arg Trp Gln Gln Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Leu Gly Lys Gly Gly Gly Gly Ser Gly Gly Gly
            260                 265                 270

Gly Ser Gly Gly Gly Gly Ser His Pro Ile Pro Asp Ser Ser Pro Leu
        275                 280                 285

Leu Gln Phe Gly Gly Gln Val Arg Gln Arg Tyr Leu Tyr Thr Asp Asp
    290                 295                 300

Ala Gln Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335

Leu Lys Pro Gly Val Ile Gln Ile Leu Gly Val Lys Thr Ser Arg Phe
            340                 345                 350

Leu Cys Gln Arg Pro Asp Gly Ala Leu Tyr Gly Ser Leu His Phe Asp
        355                 360                 365

Pro Glu Ala Cys Ser Phe Arg Glu Leu Ile Arg Pro Asp Gly Tyr Asn
    370                 375                 380

Val Tyr Gln Ser Glu Ala His Gly Leu Pro Leu His Leu Pro Gly Asn
385                 390                 395                 400

Lys Ser Pro His Arg Asp Pro Ala Pro Arg Gly Pro Ala Arg Phe Leu
                405                 410                 415

Pro Leu Pro Gly Leu Pro Pro Ala Leu Pro Glu Pro Pro Gly Ile Leu
            420                 425                 430

Ala Pro Gln Pro Pro Asp Val Gly Ser Ser Asp Pro Leu Ser Met Val
        435                 440                 445

Thr Gly Leu Glu Ala Val Arg Ser Pro Ser Tyr Glu Ser
    450                 455                 460

<210> SEQ ID NO 66
<211> LENGTH: 461
<212> TYPE: PRT
<213> ORGANISM: Artificial Sequence
<220> FEATURE:
<223> OTHER INFORMATION: GLP1(GEG)-HyFc40-GS3-FGF21(EIRP, TGLEAN, A180E)

<400> SEQUENCE: 66

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Glu
            20                  25                  30

Lys Glu Lys Glu Glu Gln Glu Arg Glu Thr Lys Thr Pro Glu Cys
        35                  40                  45

Pro Ser His Thr Gln Pro Leu Gly Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Gly
    130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Leu Gly Lys Gly Gly Gly Ser Gly Gly Gly
            260                 265                 270

Gly Ser Gly Gly Gly Ser His Pro Ile Pro Asp Ser Ser Pro Leu
        275                 280                 285

Leu Gln Phe Gly Gly Gln Val Arg Gln Arg Tyr Leu Tyr Thr Asp Asp
    290                 295                 300

Ala Gln Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335

Leu Lys Pro Gly Val Ile Gln Ile Leu Gly Val Lys Thr Ser Arg Phe
            340                 345                 350

Leu Cys Gln Arg Pro Asp Gly Ala Leu Tyr Gly Ser Leu His Phe Asp
        355                 360                 365
```

```
Pro Glu Ala Cys Ser Phe Arg Glu Glu Ile Arg Pro Asp Gly Tyr Asn
    370                 375                 380

Val Tyr Gln Ser Glu Ala His Gly Leu Pro Leu His Leu Pro Gly Asn
385                 390                 395                 400

Lys Ser Pro His Arg Asp Pro Ala Pro Arg Gly Pro Ala Arg Phe Leu
                405                 410                 415

Pro Leu Pro Gly Leu Pro Pro Ala Leu Pro Glu Pro Pro Gly Ile Leu
                420                 425                 430

Ala Pro Gln Pro Pro Asp Val Gly Ser Ser Asp Pro Leu Ser Met Val
        435                 440                 445

Thr Gly Leu Glu Ala Asn Arg Ser Pro Ser Tyr Glu Ser
450                 455                 460

<210> SEQ ID NO 67
<211> LENGTH: 460
<212> TYPE: PRT
<213> ORGANISM: Artificial Sequence
<220> FEATURE:
<223> OTHER INFORMATION: GLP1(GEG)-HyFc40-GS3-FGF21(EIRP, G170N, A180E)

<400> SEQUENCE: 67

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Glu
            20                  25                  30

Lys Glu Lys Glu Glu Gln Glu Glu Arg Glu Thr Lys Thr Pro Glu Cys
        35                  40                  45

Pro Ser His Thr Gln Pro Leu Gly Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Gly
    130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Leu Gly Lys Gly Gly Gly Gly Ser Gly Gly Gly
            260                 265                 270
```

-continued

```
Gly Ser Gly Gly Gly Ser His Pro Ile Pro Asp Ser Ser Pro Leu
            275                 280                 285

Leu Gln Phe Gly Gly Gln Val Arg Gln Arg Tyr Leu Tyr Thr Asp Asp
        290                 295                 300

Ala Gln Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335

Leu Lys Pro Gly Val Ile Gln Ile Leu Gly Val Lys Thr Ser Arg Phe
            340                 345                 350

Leu Cys Gln Arg Pro Asp Gly Ala Leu Tyr Gly Ser Leu His Phe Asp
        355                 360                 365

Pro Glu Ala Cys Ser Phe Arg Glu Glu Ile Arg Pro Asp Gly Tyr Asn
    370                 375                 380

Val Tyr Gln Ser Glu Ala His Gly Leu Pro Leu His Leu Pro Gly Asn
385                 390                 395                 400

Lys Ser Pro His Arg Asp Pro Ala Pro Arg Gly Pro Ala Arg Phe Leu
                405                 410                 415

Pro Leu Pro Gly Leu Pro Pro Ala Leu Pro Glu Pro Pro Gly Ile Leu
            420                 425                 430

Ala Pro Gln Pro Pro Asp Val Gly Ser Ser Asp Pro Leu Ser Met Val
        435                 440                 445

Asn Pro Ser Gln Gly Arg Ser Pro Ser Tyr Glu Ser
    450                 455                 460

<210> SEQ ID NO 68
<211> LENGTH: 4
<212> TYPE: PRT
<213> ORGANISM: Artificial Sequence
<220> FEATURE:
<223> OTHER INFORMATION: FGF21 variant

<400> SEQUENCE: 68

Glu Ile Arg Pro
1

<210> SEQ ID NO 69
<211> LENGTH: 6
<212> TYPE: PRT
<213> ORGANISM: Artificial Sequence
<220> FEATURE:
<223> OTHER INFORMATION: FGF21 variant

<400> SEQUENCE: 69

Thr Gly Leu Glu Ala Val
1               5

<210> SEQ ID NO 70
<211> LENGTH: 6
<212> TYPE: PRT
<213> ORGANISM: Artificial Sequence
<220> FEATURE:
<223> OTHER INFORMATION: FGF21 variant

<400> SEQUENCE: 70

Thr Gly Leu Glu Ala Asn
1               5

<210> SEQ ID NO 71
<211> LENGTH: 1383
<212> TYPE: DNA
```

<213> ORGANISM: Artificial Sequence
<220> FEATURE:
<223> OTHER INFORMATION: nucleic acid molecule coding for DFD23

<400> SEQUENCE: 71

```
cacggcgagg ggaccttcac aagcgacgtg tcctcttatc tggaaggaca ggccgctaag      60
gagtttatcg catggctcgt caaaggcaga ggcgaaaagg agaaggaaga gcaggaggag     120
agagaaacca aaacacccga gtgtcccagt cacactcagc ctctgggagt gtttctcttc     180
ccacctaagc ccaaggatac ccttatgatt tctaggacac ctgaggtgac ctgcgtcgtt     240
gtggacgtga gtcaagagga cccagaggtc cagtttaact ggtatgttga cggcgtggaa     300
gtgcataatg caaaaactaa accccgcgag gaacaattca attcaaccta ccgggtcgtt     360
tctgtgttga cagtgctgca tcaagattgg ctgaacggga aggagtataa gtgtaaagtc     420
agtaataagg gactcccctc tagtatcgaa aaaactattt caaaggccaa aggccagcct     480
agagagccac aggtgtacac ccttcctcca tcccaagagg agatgacaaa gaaccaggtg     540
tctctgactt gtcgtgaa gggttctac cctagtgaca tcgctgtcga atgggagtca     600
aacggacagc cagagaataa ttataagaca actcctcccg ttctggattc tgacggcagc     660
ttctttctgt actctaggct tactgtggac aaaagtcgct ggcaagaagg gaacgtcttt     720
tcatgttctg ttatgcacga ggccttgcac aatcattata cacagaagtc tctgagtctc     780
tcactgggca aaggcggggg aggcagcggg ggaggcgggt ccgaggcgg gggatctcat     840
cccatccctg actccagtcc tctcctgcaa ttcgggggcc aagtccggca gcggtacctc     900
tacacagatg atgctcagca gacagaagcc cacctggaga tcagggagga tgggaccgtg     960
gggggcgctg ctgaccagag ccccgaaagt ctcctgcagc tgaaagcctt gaagcctgga    1020
gttattcaaa tcttgggagt caagactagt aggttcctgt gccagcggcc agatggggcc    1080
ctgtatggat ctctccattt tgaccctgag gcctgcagct tccgggagga gatcagaccc    1140
gacggataca atgtttacca gtccgaagcc cacgcctcc ctctgcatct gcccgggaac    1200
aagtctcctc accgggaccc tgcccccaga ggacctgctc gcttcctgcc actcccaggc    1260
ctgcccccg cattgcctga gccacccgga atcctggccc ccagccccc tgatgtggga    1320
tcctctgacc ctctgagcat ggtgacaggc ctggaggccg tgagaagccc cagctacgct    1380
tcc                                                                   1383
```

<210> SEQ ID NO 72
<211> LENGTH: 1419
<212> TYPE: DNA
<213> ORGANISM: Artificial Sequence
<220> FEATURE:
<223> OTHER INFORMATION: nucleic acid molecule coding for DFD24

<400> SEQUENCE: 72

```
cacggcgagg ggaccttcac aagcgacgtg tcctcttacc tggaagagca ggccgctaag      60
gaatttatcg catggctcgt caaaggaaga gggaggaaca ccggacgggg cggggaagag     120
aagaagaaag aaaaggagaa ggaagagcag gaggagagag aaaccaaaac acccgagtgt     180
cccagtcaca ctcagcctct gggagtgttt ctcttcccac taagcccaa ggataccctt     240
atgatttcta ggacacctga ggtgacctgc gtcgttgtgg acgtgagtca agaggaccca     300
gaggtccagt ttaactggta tgttgacggc gtggaagtgc ataatgcaaa aactaaaccc     360
cgcgaggaac aattcaattc aacctaccgg gtcgttctg tgttgacagt gctgcatcaa     420
gattggctga acgggaagga gtataagtgt aaagtcagta ataagggact cccctctagt     480
```

```
atcgaaaaaa ctatttcaaa ggccaaaggc cagcctagag agccacaggt gtacacccttt    540 cctccatccc aagaggagat gacaaagaac caggtgtctc tgacttgtct cgtgaagggg    600
ttctacccta gtgacatcgc tgtcgaatgg gagtcaaacg gacagccaga gaataattat    660
aagacaactc ctcccgttct ggattctgac ggcagcttct ttctgtactc taggcttact    720
gtggacaaaa gtcgctggca agaagggaac gtcttttcat gttctgttat gcacgaggcc    780
ttgcacaatc attatacaca gaagtctctg agtctctcac tgggcaaagg cgggggaggc    840
agcgggggag gcgggtccgg aggcggggga tctcatccca tccctgactc cagtcctctc    900
ctgcaattcg gggccaagt ccggcagcgg tacctctaca cagatgatgc tcagcagaca    960
gaagcccacc tggagatcag ggaggatggg accgtggggg gcgctgctga ccagagcccc   1020
gaaagtctcc tgcagctgaa agccttgaag cctggagtta ttcaaatctt gggagtcaag   1080
actagtaggt tcctgtgcca gcggccagat ggggccctgt atggatctct ccatttgac    1140 cctgaggcct gcagcttccg ggaggagatc agacccgacg gatacaatgt ttaccagtcc   1200
gaagcccacg cctccctct gcatctgccc gggaacaagt ctcctcaccg ggaccctgcc    1260
cccagaggac ctgctcgctt cctgccactc ccaggcctgc cccccgcatt gcctgagcca   1320
cccggaatcc tggccccccca gcccctgat gtgggatcct ctgaccctct gagcatggtg   1380
acaggcctgg aggccgtgag aagccccagc tacgcttcc                          1419
```

<210> SEQ ID NO 73
<211> LENGTH: 1383
<212> TYPE: DNA
<213> ORGANISM: Artificial Sequence
<220> FEATURE:
<223> OTHER INFORMATION: nucleic acid molecule coding for DFD25

<400> SEQUENCE: 73

```
cacggcgagg ggaccttcac aagcgacgtg tcctcttacc tggaagagca ggccgctaag     60
gaatttatcg catggctcgt caaaggaaga ggggaaaagg agaaggaaga gcaggaggag    120
agagaaacca aaacacccga gtgtcccagt cacactcagc ctctgggagt gtttctcttc    180
ccacctaagc ccaaggatac ccttatgatt tctaggacac tgaggtgac ctgcgtcgtt     240 gtggacgtga gtcaagagga cccagaggtc cagtttaact ggtatgttga cggcgtggaa    300
gtgcataatg caaaaactaa accccgcgag gaacaattca attcaaccta ccgggtcgtt    360
tctgtgttga cagtgctgca tcaagattgg ctgaacggga aggagtataa gtgtaaagtc    420
agtaataagg gactcccctc tagtatcgaa aaaactattt caaggccaa aggccagcct    480 agagagccac aggtgtacac ccttcctcca tcccaagagg agatgacaaa gaaccaggtg    540
tctctgactt gtctcgtgaa ggggttctac cctagtgaca tcgctgtcga atgggagtca    600
aacggacagc cagagaataa ttataagaca actcctcccg ttctggattc tgacggcagc    660
ttctttctgt actctaggct tactgtggac aaaagtcgct ggcaagaagg gaacgtcttt    720
tcatgttctg ttatgcacga ggccttgcac aatcattata cacagaagtc tctgagtctc    780
tcactgggca aaggcggggg aggcagcggg ggaggcgggt ccggaggcgg ggatctcat    840 cccatccctg actccagtcc tctcctgcaa ttcggggcc aagtccggca gcggtacctc    900
tacacagatg atgctcagca gacagaagcc cacctggaga tcagggagga tgggaccgtg    960 ggggcgctg ctgaccagag ccccgaaagt ctcctgcagc tgaaagcctt gaagcctgga   1020
gttattcaaa tctgggagt caagactagt aggttcctgt gccagcggcc agatggggcc   1080
```

```
ctgtatggat ctctccattt tgaccctgag gcctgcagct tccgggagga gatcagaccc    1140
gacggataca atgtttacca gtccgaagcc cacggcctcc ctctgcatct gcccgggaac    1200
aagtctcctc accgggaccc tgccccaga ggacctgctc gcttcctgcc actcccaggc     1260 ctgcccccg cattgcctga gccaccggga atcctggccc ccagccccc tgatgtggga      1320 tcctctgacc ctctgagcat ggtgacaggc ctggaggccg tgagaagccc cagctacgct    1380
tcc                                                                   1383
```

<210> SEQ ID NO 74
<211> LENGTH: 1419
<212> TYPE: DNA
<213> ORGANISM: Artificial Sequence
<220> FEATURE:
<223> OTHER INFORMATION: nucleic acid molecule coding for DFD26

<400> SEQUENCE: 74

```
cacggcgagg ggaccttcac aagcgacgtg tcctcttatc tggaaggaca ggccgctaag      60
gagtttatcg catggctcgt caaaggcggc ggcaggaaca ccggacgggg cggggaagag    120
aagaagaaag aaaaggagaa ggaagagcag gaggagagag aaaccaaaac acccgagtgt    180
cccagtcaca ctcagcctct gggagtgttt ctcttcccac ctaagcccaa ggataccctt    240
atgatttcta ggacacctga ggtgacctgc gtcgttgtgg acgtgagtca agaggaccca    300
gaggtccagt ttaactggta tgttgacggc gtggaagtgc ataatgcaaa actaaaccc     360 cgcgaggaac aattcaattc aacctaccgg gtcgtttctg tgttgacagt gctgcatcaa    420
gattggctga acgggaagga gtataagtgt aaagtcagta ataagggact ccctctagt     480 atcgaaaaaa ctatttcaaa ggccaaaggc cagcctagag agccacaggt gtacacctt     540 cctccatccc aagaggagat gacaaagaac caggtgtctc tgacttgtct cgtgaagggg    600
ttctacccta gtgacatcgc tgtcgaatgg gagtcaaacg gacagccaga gaataattat    660 aagcaactc ctcccgttct ggattctgac ggcagcttct ttctgtactc taggcttact     720
gtggacaaaa gtcgctggca agaagggaac gtcttttcat gttctgttat gcacgaggcc    780
ttgcacaatc attatacaca gaagtctctg agtctctcac tgggcaaagg cggggaggc    840 agcggggag gcgggtccgg aggcggggga tctcatccca tccctgactc cagtcctctc     900
ctgcaattcg ggcccaagt ccggcagcgg tacctctaca cagatgatgc tcagcagaca     960
gaagcccacc tggagatcag ggaggatggg accgtggggg gcgctgctga ccagagcccc    1020
gaaagtctcc tgcagctgaa agccttgaag cctggagtta ttcaaatctt gggagtcaag    1080
actagtaggt tcctgtgcca gcggccagat ggggccctgt atggatctct ccattttgac    1140
cctgaggcct gcagcttccg ggaggagatc agacccgacg gatacaatgt ttaccagtcc    1200
gaagcccacg gcctccctct gcatctgccc gggaacaagt ctcctcaccg ggaccctgcc    1260
cccagaggac ctgctcgctt cctgccactc ccaggcctgc ccccgcatt gcctgagcca     1320 cccggaatcc tggccccca gccccctgat gtgggatcct ctgaccctct gagcatggtg    1380
acaggcctgg aggccgtgag aagccccagc tacgcttcc                           1419
```

<210> SEQ ID NO 75
<211> LENGTH: 1383
<212> TYPE: DNA
<213> ORGANISM: Artificial Sequence
<220> FEATURE:
<223> OTHER INFORMATION: nucleic acid molecule coding for DFD27

<400> SEQUENCE: 75

```
cacggcgagg ggaccttcac aagcgacgtg tcctcttatc tggaaggaca ggccgctaag      60
gagtttatcg catggctcgt caaaggcggc ggcgaaaagg agaaggaaga gcaggaggag     120
agagaaacca aaacacccga gtgtcccagt cacactcagc ctctgggagt gtttctcttc     180
ccacctaagc ccaaggatac ccttatgatt tctaggacac tgaggtgac ctgcgtcgtt      240
gtggacgtga gtcaagagga cccagaggtc cagtttaact ggtatgttga cggcgtggaa     300
gtgcataatg caaaaactaa accccgcgag gaacaattca attcaaccta ccgggtcgtt     360
tctgtgttga cagtgctgca tcaagattgg ctgaacggga aggagtataa gtgtaaagtc     420
agtaataagg gactcccctc tagtatcgaa aaaactattt caaaggccaa aggccagcct     480
agagagccac aggtgtacac ccttcctcca tcccaagagg agatgacaaa gaaccaggtg     540
tctctgactt gtctcgtgaa ggggttctac cctagtgaca tcgctgtcga atgggagtca     600
aacggacagc cagagaataa ttataagaca actcctcccg ttctggattc tgacggcagc     660
ttctttctgt actctaggct tactgtggac aaaagtcgct ggcaagaagg gaacgtcttt     720
tcatgttctg ttatgcacga ggccttgcac aatcattata cacagaagtc tctgagtctc     780
tcactgggca aggcggggg aggcagcggg ggaggcgggt ccggaggcgg gggatctcat      840
cccatccctg actccagtcc tctcctgcaa ttcgggggcc aagtccggca gcggtacctc     900
tacacagatg atgctcagca gacagaagcc cacctggaga tcaggaggga tgggaccgtg     960
gggggcgctg ctgaccagag ccccgaaagt ctcctgcagc tgaaagcctt gaagcctgga    1020
gttattcaaa tcttgggagt caagactagt aggttcctgt gccagcggcc agatggggcc    1080
ctgtatggat ctctccattt tgaccctgag gcctgcagct ccgggagga gatcagaccc    1140
gacggataca tgtttaccaa gtccgaagcc cacggcctcc ctctgcatct gcccgggaac    1200
aagtctcctc accgggaccc tgcccccaga ggacctgctc gcttcctgcc actcccaggc    1260
ctgccccccg cattgcctga gccacccgga atcctggccc ccagccccc tgatgtggga    1320
tcctctgacc ctctgagcat ggtgacaggc ctggaggccg tgagaagccc cagctacgct    1380
tcc                                                                  1383
```

<210> SEQ ID NO 76
<211> LENGTH: 1419
<212> TYPE: DNA
<213> ORGANISM: Artificial Sequence
<220> FEATURE:
<223> OTHER INFORMATION: nucleic acid molecule coding for DFD28

<400> SEQUENCE: 76

```
cacggcgagg ggaccttcac aagcgacgtg tcctcttacc tggaagagca ggccgctaag      60
gaatttatcg catggctcgt caaaggaggc gggaggaaca ccggacgggg cggggaagag     120
aagaagaaag aaaaggagaa ggaagagcag gaggagagag aaaccaaaac acccgagtgt     180
cccagtcaca ctcagcctct gggagtgttt ctcttcccac taagcccaa ggatacccttt     240
atgatttcta ggacacctga ggtgacctgc gtcgttgtgg acgtgagtca agaggaccca     300
gaggtccagt ttaactggta tgttgacggc gtggaagtgc ataatgcaaa actaaacccc    360
cgcgaggaac aattcaattc aacctaccgg gtcgtttctg tgttgacagt gctgcatcaa     420
gattggctga acgggaagga gtataagtgt aaagtcagta ataagggact cccctctagt    480
atcgaaaaaa ctatttcaaa ggccaaaggc cagcctagag agccacaggt gtacacccctt    540
cctccatccc aagaggagat gacaaagaac caggtgtctc tgacttgtct cgtgaagggg    600
```

```
ttctacccta gtgacatcgc tgtcgaatgg gagtcaaacg dacagccaga gaataattat    660
aagacaactc ctcccgttct ggattctgac ggcagcttct ttctgtactc taggcttact    720
gtggacaaaa gtcgctggca agaagggaac gtctttcat gttctgttat gcacgaggcc    780
ttgcacaatc attatacaca gaagtctctg agtctctcac tgggcaaagg cgggggaggc    840
agcgggggag gcgggtccgg aggcggggga tctcatccca tccctgactc cagtcctctc    900
ctgcaattcg ggggccaagt ccggcagcgg tacctctaca cagatgatgc tcagcagaca    960
gaagcccacc tggagatcag ggaggatggg accgtggggg gcgctgctga ccagagcccc   1020
gaaagtctcc tgcagctgaa agccttgaag cctggagtta ttcaaatctt gggagtcaag   1080
actagtaggt tcctgtgcca gcggccagat ggggccctgt atggatctct ccattttgac   1140
cctgaggcct gcagcttccg ggaggagatc agacccgacg gatacaatgt ttaccagtcc   1200
gaagcccacg gcctccctct gcatctgccc gggaacaagt ctcctcaccg ggaccctgcc   1260
cccagaggac ctgctcgctt cctgccactc caggcctgc ccccgcatt gcctgagcca    1320 cccggaatcc tggccccca gcccctgat gtgggatcct ctgaccctct gagcatggtg   1380
acaggcctgg aggccgtgag aagccccagc tacgcttcc                         1419
```

<210> SEQ ID NO 77
<211> LENGTH: 1383
<212> TYPE: DNA
<213> ORGANISM: Artificial Sequence
<220> FEATURE:
<223> OTHER INFORMATION: nucleic acid molecule coding for DFD29

<400> SEQUENCE: 77

```
cacggcgagg ggaccttcac aagcgacgtg tcctcttacc tggaagagca ggccgctaag     60
gaatttatcg catggctcgt caaggaggc ggggaaaagg agaaggaaga gcaggaggag    120
agagaaacca aaacacccga gtgtcccagt cacactcagc ctctgggagt gtttctcttc    180
ccacctaagc ccaaggatac ccttatgatt tctaggacac tgaggtgac ctgcgtcgtt     240 gtggacgtga gtcaagagga cccagaggtc cagtttaact ggtatgttga cggcgtggaa    300
gtgcataatg caaaaactaa accccgcgag gaacaattca attcaaccta ccgggtcgtt    360
tctgtgttga cagtgctgca tcaagattgg ctgaacggga aggagtataa gtgtaaagtc    420
agtaataagg gactccccte tagtatcgaa aaaactattt caaggccaa aggccagcct    480 agagagccac aggtgtacac ccttcctcca tcccaagagg agatgacaaa gaaccaggtg    540
tctctgactt gtctcgtgaa ggggttctac cctagtgaca tcgctgtcga atgggagtca    600
aacggacagc cagagaataa ttataagaca actcctcccg ttctggattc tgacggcagc    660
ttctttctgt actctaggct tactgtggac aaaagtcgct ggcaagaagg gaacgtcttt    720
tcatgttctg ttatgcacga ggccttgcac aatcattata cacagaagtc tctgagtctc    780
tcactgggca aaggcgggg aggcagcggg ggaggcgggt ccggaggcgg gggatctcat    840
cccatccctg actccagtcc tctcctgcaa ttcgggggcc aagtccggca gcggtacctc    900
tacacagatg atgctcagca gacagaagcc cacctggaga tcagggagga tgggaccgtg    960
ggggcgctgc tgaccagag ccccgaaagt ctcctgcagc tgaaagcctt gaagcctgga   1020
gttattcaaa tctgggagt caagactagt aggttcctgt gccagcggcc agatggggcc   1080
ctgtatggat ctctccattt tgaccctgag gcctgcagct tccggaggag gatcagaccc    1140
gacggataca atgtttacca gtccgaagcc cacggcctcc ctctgcatct gcccgggaac   1200
aagtctcctc accggaccc tgcccccaga ggacctgctc gcttcctgcc actcccaggc   1260
```

```
ctgcccccg cattgcctga gccacccgga atcctggccc ccagccccc tgatgtggga    1320 tcctctgacc ctctgagcat ggtgacaggc ctggaggccg tgagaagccc cagctacgct   1380
tcc                                                                 1383
```

<210> SEQ ID NO 78
<211> LENGTH: 1383
<212> TYPE: DNA
<213> ORGANISM: Artificial Sequence
<220> FEATURE:
<223> OTHER INFORMATION: nucleic acid molecule coding for DFD69

<400> SEQUENCE: 78

```
cacggcgagg ggaccttcac aagcgacgtg tcctcttacc tggaagagca ggccgctaag     60
gaatttatcg catggctcgt caaggaggc ggggaaaagg agaaggaaga gcaggaggag    120
agagaaacca aaacacccga gtgtcccagt cacactcagc ctctgggagt gtttctcttc    180
ccacctaagc ccaaggatac ccttatgatt tctaggacac tgaggtgac ctgcgtcgtt    240 gtggacgtga gtcaagagga cccagaggtc cagtttaact ggtatgttga cggcgtggaa    300
gtgcataatg caaaaactaa accccgcgag gaacaattca attcaaccta ccgggtcgtt    360
tctgtgttga cagtgctgca tcaagattgg ctgaacggga aggagtataa gtgtaaagtc    420
agtaataagg gactcccctc tagtatcgaa aaaactattt caaggccaa aggccagcct    480 agagagccac aggtgtacac ccttcctcca tcccaagagg agatgacaaa gaaccaggtg    540
tctctgactt gtctcgtgaa ggggttctac cctagtgaca tcgctgtcga atgggagtca    600
aacggacagc cagagaataa ttataagaca actcctcccg ttctggattc tgacggcagc    660
ttctttctgt actctaggct tactgtggac aaaagtcgct ggcaagaagg gaacgtcttt    720
tcatgttctg ttatgcacga ggccttgcac aatcattata cacagaagtc tctgagtctc    780
tcactgggca aggcgggg aggcagcggg ggaggcgggt ccggaggcgg gggatctcat    840
cccatccctg actccagtcc tctcctgcaa ttcggggcc aagtccggca gcggtacctc    900
tacacagatg atgctcagca gacagaagcc cacctggaga tcaggaggga tgggaccgtg    960
gggggcgctg ctgaccagag ccccgaaagt ctcctgcagc tgaaagcctt gaagcctgga   1020
gttattcaaa tcttgggagt caagactagt aggttcctgt gccagcggcc agatgggcc    1080 ctgtatggat ctctccattt tgaccctgag gcctgcagct ccggaggga gatcagaccc    1140 gacggataca atgtttacca gtccgaagcc cacggcctcc ctctgcatct gcccgggaac    1200
aagtctcctc accgggaccc tgcccccaga ggacctgctc gcttcctgcc actcccaggc    1260 ctgcccccg cattgcctga gccacccgga atcctggccc ccagccccc tgatgtggga    1320 tcctctgacc ctctgagcat ggtgacaggc ctggaggccg tgagaagccc cagctacgag   1380
tcc                                                                 1383
```

<210> SEQ ID NO 79
<211> LENGTH: 1383
<212> TYPE: DNA
<213> ORGANISM: Artificial Sequence
<220> FEATURE:
<223> OTHER INFORMATION: nucleic acid molecule coding for DFD112

<400> SEQUENCE: 79

```
cacggcgagg ggaccttcac aagcgacgtg tcctcttacc tggaagagca ggccgctaag     60
gaatttatcg catggctcgt caaggaggc ggggaaaagg agaaggaaga gcaggaggag    120
```

| | |
|---|---:|
| agagaaacca aaacacccga gtgtcccagt cacactcagc ctctgggagt gtttctcttc | 180 |
| ccacctaagc ccaaggatac ccttatgatt tctaggacac ctgaggtgac ctgcgtcgtt | 240 |
| gtggacgtga gtcaagagga cccagaggtc cagtttaact ggtatgttga cggcgtggaa | 300 |
| gtgcataatg caaaaactaa accccgcgag gaacaattca attcaaccta ccgggtcgtt | 360 |
| tctgtgttga cagtgctgca tcaagattgg ctgaacggga aggagtataa gtgtaaagtc | 420 |
| agtaataagg gactcccctc tagtatcgaa aaaactattt caaaggccaa aggccagcct | 480 |
| agagagccac aggtgtacac ccttcctcca tcccaagagg agatgacaaa gaaccaggtg | 540 |
| tctctgactt gtctcgtgaa ggggttctac cctagtgaca tcgctgtcga atgggagtca | 600 |
| aacggacagc cagagaataa ttataagaca actcctcccg ttctggattc tgacggcagc | 660 |
| ttctttctgt actctaggct tactgtggac aaaagtcgct ggcaagaagg gaacgtcttt | 720 |
| tcatgttctg ttatgcacga ggccttgcac aatcattata cacagaagtc tctgagtctc | 780 |
| tcactgggca aaggcggggg aggcagcggg ggaggcgggt ccggaggcgg gggatctcat | 840 |
| cccatccctg actccagtcc tctcctgcaa ttcgggggcc aagtccggca gcggtaccto | 900 |
| tacacagatg atgctcagca gacagaagcc cacctggaga tcaggaggga tgggaccgtg | 960 |
| gggggcgctg ctgaccagag ccccgaaagt ctcctgcagc tgaaagcctt gaagcctgga | 1020 |
| gttattcaaa tcttgggagt caagactagt aggttcctgt gccagcggcc agatggggcc | 1080 |
| ctgtatggat ctctccattt tgaccctgag gcctgcagct ccggaggga gatcagaccc | 1140 |
| gacggataca atgtttacca gtccgaagcc cacggcctcc ctctgcatct gcccgggaac | 1200 |
| aagtctcctc accgggaccc tgcccccaga ggacctgctc gcttcctgcc actcccaggc | 1260 |
| ctgccccccg cattgcctga gccacccgga atcctggccc ccagcccccc tgatgtggga | 1320 |
| tcctctgacc ctctgagcat ggtgacaggc ctggaggcca acagaagccc cagctacgag | 1380 |
| tcc | 1383 |

<210> SEQ ID NO 80
<211> LENGTH: 1380
<212> TYPE: DNA
<213> ORGANISM: Artificial Sequence
<220> FEATURE:
<223> OTHER INFORMATION: nucleic acid molecule coding for DFD114

<400> SEQUENCE: 80

| | |
|---|---:|
| cacggcgagg ggaccttcac aagcgacgtg tcctcttacc tggaagagca ggccgctaag | 60 |
| gaatttatcg catggctcgt caaaggaggc ggggaaaagg agaaggaaga gcaggaggag | 120 |
| agagaaacca aaacacccga gtgtcccagt cacactcagc ctctgggagt gtttctcttc | 180 |
| ccacctaagc ccaaggatac ccttatgatt tctaggacac ctgaggtgac ctgcgtcgtt | 240 |
| gtggacgtga gtcaagagga cccagaggtc cagtttaact ggtatgttga cggcgtggaa | 300 |
| gtgcataatg caaaaactaa accccgcgag gaacaattca attcaaccta ccgggtcgtt | 360 |
| tctgtgttga cagtgctgca tcaagattgg ctgaacggga aggagtataa gtgtaaagtc | 420 |
| agtaataagg gactcccctc tagtatcgaa aaaactattt caaaggccaa aggccagcct | 480 |
| agagagccac aggtgtacac ccttcctcca tcccaagagg agatgacaaa gaaccaggtg | 540 |
| tctctgactt gtctcgtgaa ggggttctac cctagtgaca tcgctgtcga atgggagtca | 600 |
| aacggacagc cagagaataa ttataagaca actcctcccg ttctggattc tgacggcagc | 660 |
| ttctttctgt actctaggct tactgtggac aaaagtcgct ggcaagaagg gaacgtcttt | 720 |
| tcatgttctg ttatgcacga ggccttgcac aatcattata cacagaagtc tctgagtctc | 780 |

```
tcactgggca aaggcggggg aggcagcggg ggaggcgggt ccggaggcgg gggatctcat    840
cccatccctg actccagtcc tctcctgcaa ttcgggggcc aagtccggca gcggtacctc    900
tacacagatg atgctcagca gacagaagcc cacctggaga tcagggagga tgggaccgtg    960
gggggcgctg ctgaccagag ccccgaaagt ctcctgcagc tgaaagcctt gaagcctgga   1020
gttattcaaa tcttgggagt caagactagt aggttcctgt gccagcggcc agatggggcc   1080
ctgtatggat ctctccattt tgaccctgag gcctgcagct tccgggagga gatcagaccc   1140
gacggataca atgtttacca gtccgaagcc cacggcctcc ctctgcatct gcccgggaac   1200
aagtctcctc accgggaccc tgcccccaga ggacctgctc gcttcctgcc actcccaggc   1260 ctgcccccg cattgcctga gccacccgga atcctggccc cccagccccc tgatgtggga    1320
tcctctgacc ctctgagcat ggtgaaccct tcccagggca gaagcccag ctacgagtcc     1380

<210> SEQ ID NO 81
<211> LENGTH: 4
<212> TYPE: PRT
<213> ORGANISM: Artificial Sequence
<220> FEATURE:
<223> OTHER INFORMATION: Position 98-101 of FGF21

<400> SEQUENCE: 81

Leu Leu Leu Glu
1

<210> SEQ ID NO 82
<211> LENGTH: 5
<212> TYPE: PRT
<213> ORGANISM: Artificial Sequence
<220> FEATURE:
<223> OTHER INFORMATION: Position 170-174 of FGF21

<400> SEQUENCE: 82

Gly Pro Ser Gln Gly
1               5

<210> SEQ ID NO 83
<211> LENGTH: 25
<212> TYPE: PRT
<213> ORGANISM: Artificial Sequence
<220> FEATURE:
<223> OTHER INFORMATION: Leader sequence

<400> SEQUENCE: 83

Met Asp Ala Met Leu Arg Gly Leu Cys Cys Val Leu Leu Cys Gly
1               5                   10                  15

Ala Val Phe Val Ser Pro Ser His Ala
            20                  25
```